US010828356B1

(12) United States Patent
Bermudes

(10) Patent No.: US 10,828,356 B1
(45) Date of Patent: Nov. 10, 2020

(54) MODIFIED BACTERIA HAVING IMPROVED PHARMACOKINETICS AND TUMOR COLONIZATION ENHANCING ANTITUMOR ACTIVITY

(71) Applicant: David Gordon Bermudes, Woodland Hills, CA (US)

(72) Inventor: David Gordon Bermudes, Woodland Hills, CA (US)

( * ) Notice: Subject to any disclaimer, the term of this patent is extended or adjusted under 35 U.S.C. 154(b) by 0 days.

(21) Appl. No.: 16/410,627

(22) Filed: May 13, 2019

Related U.S. Application Data

(60) Division of application No. 15/679,874, filed on Aug. 17, 2017, now Pat. No. 10,449,237, which is a continuation of application No. 15/482,170, filed on Apr. 7, 2017, now Pat. No. 10,286,051, which is a division of application No. 14/858,810, filed on Sep. 18, 2015, now Pat. No. 9,616,114.

(60) Provisional application No. 62/052,252, filed on Sep. 18, 2014.

(51) Int. Cl.
*A61K 39/00* (2006.01)
*A61K 39/02* (2006.01)
*A61K 39/44* (2006.01)

(52) U.S. Cl.
CPC .......... *A61K 39/0011* (2013.01); *A61K 39/02* (2013.01); *A61K 2039/52* (2013.01); *A61K 2039/585* (2013.01)

(58) Field of Classification Search
CPC .......... A61K 2039/52; A61K 2039/585; A61K 35/74; A61K 39/0011; C11D 11/0082; C11D 3/0052; C11D 3/046; C11D 3/10; C12N 15/74
See application file for complete search history.

(56) References Cited

U.S. PATENT DOCUMENTS

| | | |
|---|---|---|
| 3,939,558 A | 2/1976 | Riley |
| 4,703,008 A | 10/1987 | Lin |
| 5,057,417 A | 10/1991 | Hammonds et al. |
| 5,098,833 A | 3/1992 | Lasky et al. |
| 5,116,964 A | 5/1992 | Capon et al. |
| 5,143,830 A | 9/1992 | Holland et al. |
| 5,202,422 A | 4/1993 | Hiatt et al. |
| 5,238,839 A | 8/1993 | Cantor et al. |
| 5,278,049 A | 1/1994 | Baker et al. |
| 5,316,933 A | 5/1994 | Yoshimatsu et al. |
| 5,328,985 A | 7/1994 | Sano et al. |
| 5,356,795 A | 10/1994 | Leonard et al. |
| 5,356,804 A | 10/1994 | Desnick et al. |
| 5,376,567 A | 12/1994 | McCormick et al. |
| 5,382,524 A | 1/1995 | Desnick et al. |
| 5,387,676 A | 2/1995 | Zavada et al. |
| 5,439,808 A | 8/1995 | Blake et al. |
| 5,455,165 A | 10/1995 | Capon et al. |
| 5,460,961 A | 10/1995 | Deby et al. |
| 5,470,719 A | 11/1995 | Meng et al. |
| 5,491,075 A | 2/1996 | Desnick et al. |
| 5,508,192 A | 4/1996 | Georgiou et al. |
| 5,514,582 A | 5/1996 | Capon et al. |
| 5,525,502 A | 6/1996 | Thireos et al. |
| 5,543,312 A | 8/1996 | Mellors et al. |
| 5,545,553 A | 8/1996 | Gotschlich |
| 5,583,010 A | 12/1996 | Baumbach et al. |
| 5,585,269 A | 12/1996 | Earp, III et al. |
| 5,591,641 A | 1/1997 | Thorner et al. |
| 5,593,882 A | 1/1997 | Erbe et al. |
| 5,604,115 A | 2/1997 | Sladek et al. |
| 5,624,832 A | 4/1997 | Fukuda et al. |
| 5,631,156 A | 5/1997 | Xiong et al. |
| 5,631,228 A | 5/1997 | Oppenheim et al. |
| 5,665,357 A | 9/1997 | Rose et al. |
| 5,726,037 A | 3/1998 | Bodary et al. |
| 5,747,287 A | 5/1998 | Blake et al. |
| 5,747,326 A | 5/1998 | Gerardy-Schahn et al. |
| 5,747,659 A | 5/1998 | Fioretti et al. |
| 5,767,241 A | 6/1998 | McEver |
| 5,770,420 A | 6/1998 | Lowe et al. |
| 5,776,755 A | 7/1998 | Alitalo et al. |
| 5,786,179 A | 7/1998 | Kousoulas et al. |
| 5,824,502 A | 10/1998 | Honjo et al. |
| 5,824,509 A | 10/1998 | Aggarwal et al. |
| 5,837,488 A | 11/1998 | Garfinkel et al. |
| 5,843,707 A | 12/1998 | Larsen et al. |
| 5,849,702 A | 12/1998 | Garfinkel et al. |
| 5,863,758 A | 1/1999 | Oppermann et al. |
| 5,877,159 A | 3/1999 | Powell et al. |
| 5,879,686 A | 3/1999 | Blake et al. |
| 5,902,742 A | 5/1999 | Petter et al. |
| 5,912,141 A | 6/1999 | Brojatsch et al. |
| 5,912,230 A | 6/1999 | Oppenheim et al. |

(Continued)

FOREIGN PATENT DOCUMENTS

| | | |
|---|---|---|
| EP | 0973911 | 1/2000 |
| EP | 1270730 A1 | 1/2003 |
| EP | 1655370 | 5/2006 |
| EP | 1402036 B1 | 2/2008 |
| EP | 1068339 B1 | 7/2008 |
| EP | 1407052 B1 | 12/2008 |
| EP | 2611823 | 7/2013 |
| WO | WO1996040238 | 12/1996 |
| WO | WO1997014782 | 4/1997 |
| WO | WO2000004919 | 2/2000 |
| WO | WO2000047222 | 8/2000 |
| WO | WO2001025397 | 4/2001 |
| WO | WO2002067983 | 9/2002 |

(Continued)

*Primary Examiner* — Padmavathi Baskar
(74) *Attorney, Agent, or Firm* — Hoiffberg & Associates; Steven M. Hoffberg

(57) ABSTRACT

Bacterial strains are provided having at least one of a reduced size, a sialic acid coat, inducibly altered surface antigens, and expression of PD-L1 or CTLA-4 antagonists and/or tryptophanase. The bacteria may have improved serum half-life, increased penetration into tumors, increased tumor targeting and increased antitumor activity. The bacteria are useful for delivery of therapeutic agents that treat of neoplastic diseases including solid tumors and lymphomas.

21 Claims, 4 Drawing Sheets

Specification includes a Sequence Listing.

(56) References Cited

U.S. PATENT DOCUMENTS

| | | |
|---|---|---|
| 5,925,521 A | 7/1999 | Bandman et al. |
| 5,928,892 A | 7/1999 | Hourcade et al. |
| 5,945,322 A | 8/1999 | Gotschlich |
| 5,955,347 A | 9/1999 | Lowe |
| 5,965,382 A | 10/1999 | Koths et al. |
| 5,965,385 A | 10/1999 | Read et al. |
| 5,976,852 A | 11/1999 | Cheng et al. |
| 5,977,304 A | 11/1999 | Read et al. |
| 5,989,868 A | 11/1999 | Harrison et al. |
| 5,993,827 A | 11/1999 | Sim et al. |
| 5,994,625 A | 11/1999 | Melchers et al. |
| 6,005,089 A | 12/1999 | Lanza et al. |
| 6,017,743 A | 1/2000 | Tsuji et al. |
| 6,018,022 A | 1/2000 | Read et al. |
| 6,022,729 A | 2/2000 | Steinbuchel et al. |
| 6,025,183 A | 2/2000 | Soreq et al. |
| 6,030,624 A | 2/2000 | Russell et al. |
| 6,033,663 A | 3/2000 | Ketcham et al. |
| 6,037,159 A | 3/2000 | Uchimura et al. |
| 6,040,156 A | 3/2000 | Kawasaki et al. |
| 6,054,309 A | 4/2000 | Hirabayashi et al. |
| 6,069,127 A | 5/2000 | Koths et al. |
| 6,074,840 A | 6/2000 | Bonadio et al. |
| 6,080,849 A | 6/2000 | Bermudes et al. |
| 6,083,688 A | 7/2000 | Lanza et al. |
| 6,090,582 A | 7/2000 | Kikly et al. |
| 6,093,539 A | 7/2000 | Maddon et al. |
| 6,096,529 A | 8/2000 | Gilbert et al. |
| 6,110,899 A | 8/2000 | Lonetto |
| 6,111,089 A | 8/2000 | Fukuda |
| 6,117,651 A | 9/2000 | Schultz et al. |
| 6,117,977 A | 9/2000 | Lasky et al. |
| 6,124,446 A | 9/2000 | Hillman et al. |
| 6,146,845 A | 11/2000 | Kikly et al. |
| 6,146,849 A | 11/2000 | Pierce et al. |
| 6,150,170 A | 11/2000 | Powell et al. |
| 6,166,290 A | 12/2000 | Rea et al. |
| 6,190,657 B1 | 2/2001 | Pawelek et al. |
| 6,200,779 B1 | 3/2001 | Lonetto |
| 6,207,417 B1 | 3/2001 | Zsebo et al. |
| 6,207,648 B1 | 3/2001 | Waxman et al. |
| 6,218,148 B1 | 4/2001 | Zsebo et al. |
| 6,238,914 B1 | 5/2001 | Boyce |
| 6,242,210 B1 | 6/2001 | Bjorck et al. |
| 6,261,800 B1 | 7/2001 | Nikolics et al. |
| 6,268,193 B1 | 7/2001 | Lowe |
| 6,271,011 B1 | 8/2001 | Lee et al. |
| 6,271,368 B1 | 8/2001 | Lentzen et al. |
| 6,274,339 B1 | 8/2001 | Moore et al. |
| 6,277,574 B1 | 8/2001 | Walker et al. |
| 6,280,989 B1 | 8/2001 | Kapitonov et al. |
| 6,284,493 B1 | 9/2001 | Roth |
| 6,302,685 B1 | 10/2001 | Lobel et al. |
| 6,303,571 B1 | 10/2001 | Lonetto |
| 6,310,046 B1 | 10/2001 | Duffy et al. |
| 6,312,907 B1 | 11/2001 | Guo et al. |
| 6,316,609 B1 | 11/2001 | Dillon et al. |
| 6,331,413 B1 | 12/2001 | Adler et al. |
| 6,333,182 B1 | 12/2001 | Coleman et al. |
| 6,338,953 B1 | 1/2002 | Boyce et al. |
| 6,338,955 B2 | 1/2002 | Oguri et al. |
| 6,342,382 B1 | 1/2002 | Gotschlich |
| 6,358,724 B1 | 3/2002 | Wong-Madden et al. |
| 6,375,947 B1 | 4/2002 | Bolen et al. |
| 6,379,913 B1 | 4/2002 | Bandman et al. |
| 6,387,702 B1 | 5/2002 | Stemmer |
| 6,399,326 B1 | 6/2002 | Chiang et al. |
| 6,399,336 B1 | 6/2002 | Paulson et al. |
| 6,416,988 B1 | 7/2002 | Conklin et al. |
| 6,420,135 B1 | 7/2002 | Kunsch et al. |
| 6,420,149 B1 | 7/2002 | Fukuda et al. |
| 6,420,527 B1 | 7/2002 | Bolen et al. |
| 6,423,525 B1 | 7/2002 | Landry |
| 6,428,999 B1 | 8/2002 | Ito et al. |
| 6,436,687 B1 | 8/2002 | Yu et al. |
| 6,447,784 B1 | 9/2002 | Bermudes et al. |
| 6,458,573 B1 | 10/2002 | Landry |
| 6,472,518 B1 | 10/2002 | Ribot et al. |
| 6,475,482 B1 | 11/2002 | Bermudes et al. |
| 6,482,647 B1 | 11/2002 | Stemmer |
| 6,492,152 B1 | 12/2002 | Canfield et al. |
| 6,500,419 B1 | 12/2002 | Hone et al. |
| 6,503,744 B1 | 1/2003 | Gilbert et al. |
| 6,506,550 B1 | 1/2003 | Fulton et al. |
| 6,514,724 B1 | 2/2003 | McMahon et al. |
| 6,521,439 B2 | 2/2003 | Folkman et al. |
| 6,524,792 B1 | 2/2003 | Renner et al. |
| 6,524,820 B1 | 2/2003 | Pierce et al. |
| 6,531,306 B1 | 3/2003 | Hockensmith et al. |
| 6,534,311 B2 | 3/2003 | Stewart et al. |
| 6,548,287 B1 | 4/2003 | Powell et al. |
| 6,555,343 B1 | 4/2003 | DeSauvage et al. |
| 6,558,953 B1 | 5/2003 | Gonsalves et al. |
| 6,570,000 B1 | 5/2003 | Maddon et al. |
| 6,573,082 B1 | 6/2003 | Choi et al. |
| 6,582,948 B1 | 6/2003 | Bolen et al. |
| 6,582,950 B1 | 6/2003 | Smith et al. |
| 6,605,592 B2 | 8/2003 | Ni et al. |
| 6,607,897 B2 | 8/2003 | Vogel et al. |
| 6,635,246 B1 | 10/2003 | Barrett et al. |
| 6,635,468 B2 | 10/2003 | Ashkenazi et al. |
| 6,642,041 B2 | 11/2003 | Chen et al. |
| 6,646,113 B1 | 11/2003 | Dreyfuss et al. |
| 6,673,915 B1 | 1/2004 | Luster et al. |
| 6,682,729 B1 | 1/2004 | Powell et al. |
| 6,682,910 B2 | 1/2004 | Powell |
| 6,685,935 B1 | 2/2004 | Pawelek et al. |
| 6,689,604 B1 | 2/2004 | Gilbert et al. |
| 6,693,183 B1 | 2/2004 | Natsuka et al. |
| 6,696,411 B1 | 2/2004 | MacLeod |
| 6,699,705 B2 | 3/2004 | Gilbert et al. |
| 6,709,656 B1 | 3/2004 | Boren et al. |
| 6,709,830 B2 | 3/2004 | Witte et al. |
| 6,709,834 B2 | 3/2004 | Gilbert et al. |
| 6,713,277 B1 | 3/2004 | Moore et al. |
| 6,720,410 B2 | 4/2004 | Cerny et al. |
| 6,753,164 B2 | 6/2004 | Ni et al. |
| 6,759,215 B1 | 7/2004 | Zsebo et al. |
| 6,759,230 B1 | 7/2004 | Bulla, Jr. et al. |
| 6,770,466 B2 | 8/2004 | Shi et al. |
| 6,770,632 B1 | 8/2004 | Aghi et al. |
| 6,780,624 B2 | 8/2004 | Gotschlich |
| 6,783,966 B1 | 8/2004 | Kojima et al. |
| 6,783,971 B2 | 8/2004 | Coleman et al. |
| 6,784,164 B2 | 8/2004 | Masure et al. |
| 6,787,643 B2 | 9/2004 | Dillon et al. |
| 6,803,192 B1 | 10/2004 | Chen |
| 6,818,449 B2 | 11/2004 | Fong et al. |
| 6,825,019 B2 | 11/2004 | Gilbert et al. |
| 6,828,121 B2 | 12/2004 | Chen |
| 6,828,146 B2 | 12/2004 | Desnoyers et al. |
| 6,828,419 B2 | 12/2004 | Adler et al. |
| 6,831,060 B2 | 12/2004 | DeSauvage et al. |
| 6,833,130 B1 | 12/2004 | Paton et al. |
| 6,833,253 B2 | 12/2004 | Choi |
| 6,833,255 B1 | 12/2004 | Stewart et al. |
| 6,841,718 B2 | 1/2005 | Alberte et al. |
| 6,844,178 B2 | 1/2005 | Bolen et al. |
| 6,846,667 B1 | 1/2005 | Crooke et al. |
| 6,858,407 B2 | 2/2005 | Feder et al. |
| 6,858,415 B2 | 2/2005 | Coleman et al. |
| 6,861,231 B2 | 3/2005 | Shao |
| 6,863,894 B2 | 3/2005 | Bermudes et al. |
| 6,872,526 B2 | 3/2005 | Short et al. |
| 6,887,663 B1 | 5/2005 | Choi et al. |
| 6,902,932 B2 | 6/2005 | Altman et al. |
| 6,905,867 B2 | 6/2005 | Gilbert et al. |
| 6,911,337 B2 | 6/2005 | Gilbert et al. |
| 6,913,906 B2 | 7/2005 | Bolen et al. |
| 6,913,919 B2 | 7/2005 | Botstein et al. |
| 6,916,648 B2 | 7/2005 | Goddard et al. |
| 6,916,918 B2 | 7/2005 | Yu et al. |
| 6,921,659 B2 | 7/2005 | Joly |
| 6,923,972 B2 | 8/2005 | Bermudes et al. |

(56) References Cited

U.S. PATENT DOCUMENTS

| | | |
|---|---|---|
| 6,929,930 B2 | 8/2005 | Choi et al. |
| 6,936,448 B2 | 8/2005 | Holmes et al. |
| 6,943,001 B2 | 9/2005 | Zhao et al. |
| 6,943,241 B2 | 9/2005 | Isogai et al. |
| 6,946,262 B2 | 9/2005 | Ferrara et al. |
| 6,949,372 B2 | 9/2005 | Betenbaugh et al. |
| 6,951,737 B2 | 10/2005 | Desnoyers et al. |
| 6,951,738 B2 | 10/2005 | Ni et al. |
| 6,962,696 B1 | 11/2005 | Bermudes et al. |
| 6,962,800 B2 | 11/2005 | Kiy et al. |
| 6,972,185 B2 | 12/2005 | Desnoyers et al. |
| 6,972,186 B2 | 12/2005 | Desnoyers et al. |
| 6,974,689 B1 | 12/2005 | Ashkenazi et al. |
| 6,974,696 B2 | 12/2005 | Botstein et al. |
| 6,974,893 B2 | 12/2005 | Shanklin et al. |
| 6,979,556 B2 | 12/2005 | Simmons et al. |
| 6,979,733 B2 | 12/2005 | Zhao et al. |
| 6,987,176 B1 | 1/2006 | Guerry et al. |
| 7,015,027 B1 | 3/2006 | Redshaw |
| 7,018,811 B2 | 3/2006 | Botstein et al. |
| 7,019,124 B2 | 3/2006 | Desnoyers et al. |
| 7,022,498 B2 | 4/2006 | Desnoyers et al. |
| 7,026,449 B2 | 4/2006 | Baker et al. |
| 7,029,875 B2 | 4/2006 | Desnoyers et al. |
| 7,033,785 B2 | 4/2006 | Desnoyers et al. |
| 7,033,786 B2 | 4/2006 | Baker et al. |
| 7,033,825 B2 | 4/2006 | Goddard et al. |
| 7,034,136 B2 | 4/2006 | Goddard et al. |
| 7,037,679 B2 | 5/2006 | Desnoyers et al. |
| 7,037,710 B2 | 5/2006 | Goddard et al. |
| 7,041,441 B1 | 5/2006 | Steven et al. |
| 7,041,814 B1 | 5/2006 | Weinstock et al. |
| 7,049,096 B2 | 5/2006 | Feder et al. |
| 7,052,889 B2 | 5/2006 | Jenuwein et al. |
| 7,056,510 B1 | 6/2006 | Choi et al. |
| 7,056,721 B2 | 6/2006 | Dunn-Coleman et al. |
| 7,056,736 B2 | 6/2006 | Ashkenazi et al. |
| 7,056,737 B2 | 6/2006 | Feder et al. |
| 7,060,479 B2 | 6/2006 | Dumas Milne Edwards et al. |
| 7,060,812 B2 | 6/2006 | Desnoyers et al. |
| 7,067,306 B2 | 6/2006 | Singhvi et al. |
| 7,070,979 B2 | 7/2006 | Botstein et al. |
| 7,074,589 B1 | 7/2006 | Ullrich et al. |
| 7,074,592 B2 | 7/2006 | Ashkenazi et al. |
| 7,078,185 B2 | 7/2006 | Farnet et al. |
| 7,078,186 B2 | 7/2006 | Ni et al. |
| 7,078,207 B2 | 7/2006 | Gilbert et al. |
| 7,083,791 B2 | 8/2006 | Sleeman et al. |
| 7,083,946 B2 | 8/2006 | Baker et al. |
| 7,083,978 B2 | 8/2006 | Desnoyers et al. |
| 7,084,105 B2 | 8/2006 | Chakrabarty et al. |
| 7,087,404 B2 | 8/2006 | Desnoyers et al. |
| 7,087,738 B2 | 8/2006 | Botstein et al. |
| 7,091,315 B1 | 8/2006 | Ruben et al. |
| 7,094,563 B2 | 8/2006 | Wong-Madden et al. |
| 7,094,567 B2 | 8/2006 | Ashkenazi et al. |
| 7,094,572 B2 | 8/2006 | Ramanathan et al. |
| 7,109,033 B2 | 9/2006 | Harper et al. |
| 7,109,315 B2 | 9/2006 | Bryan et al. |
| 7,115,402 B2 | 10/2006 | Feder et al. |
| 7,122,185 B2 | 10/2006 | Olson et al. |
| 7,122,358 B2 | 10/2006 | Feder et al. |
| 7,122,367 B2 | 10/2006 | Milcamps et al. |
| 7,122,375 B2 | 10/2006 | Goddard et al. |
| 7,125,548 B2 | 10/2006 | Smith |
| 7,125,718 B2 | 10/2006 | Powell et al. |
| 7,129,085 B2 | 10/2006 | Feder et al. |
| 7,132,283 B2 | 11/2006 | Fong et al. |
| 7,138,252 B2 | 11/2006 | Bachmann et al. |
| 7,138,258 B2 | 11/2006 | Gilbert et al. |
| 7,138,259 B2 | 11/2006 | Beavo et al. |
| 7,141,418 B2 | 11/2006 | Kunsch et al. |
| 7,153,678 B2 | 12/2006 | Jackson et al. |
| 7,163,797 B2 | 1/2007 | Ruben et al. |
| 7,169,565 B2 | 1/2007 | Ruben et al. |
| 7,169,912 B2 | 1/2007 | Desnoyers et al. |
| 7,183,379 B2 | 2/2007 | Feder et al. |
| 7,186,564 B2 | 3/2007 | Chen et al. |
| 7,189,529 B2 | 3/2007 | Ashkenazi et al. |
| 7,189,530 B2 | 3/2007 | Botstein et al. |
| 7,189,539 B2 | 3/2007 | Ramanathan et al. |
| 7,189,836 B2 | 3/2007 | Gilbert et al. |
| 7,192,933 B1 | 3/2007 | Boyce |
| 7,195,757 B2 | 3/2007 | Curtiss, III et al. |
| 7,198,912 B2 | 4/2007 | Ramanathan et al. |
| 7,202,056 B2 | 4/2007 | Lee et al. |
| 7,202,059 B2 | 4/2007 | Habermann et al. |
| 7,202,353 B2 | 4/2007 | Gilbert et al. |
| 7,208,304 B2 | 4/2007 | Gilbert et al. |
| 7,208,312 B1 | 4/2007 | Desnoyers et al. |
| 7,211,657 B2 | 5/2007 | Gilbert et al. |
| 7,214,792 B2 | 5/2007 | Bulla et al. |
| 7,217,548 B2 | 5/2007 | Yoshida et al. |
| 7,217,549 B2 | 5/2007 | Gilbert et al. |
| 7,217,809 B2 | 5/2007 | Schultz et al. |
| 7,220,555 B2 | 5/2007 | Paulson et al. |
| 7,220,848 B2 | 5/2007 | Gilbert et al. |
| 7,223,557 B2 | 5/2007 | Lee et al. |
| 7,223,586 B2 | 5/2007 | Ferrara et al. |
| 7,226,791 B2 | 6/2007 | Carman et al. |
| 7,232,672 B2 | 6/2007 | Weiner et al. |
| 7,238,509 B2 | 7/2007 | Gilbert et al. |
| 7,244,601 B2 | 7/2007 | Gilbert et al. |
| 7,244,833 B2 | 7/2007 | Yu et al. |
| 7,247,296 B2 | 7/2007 | Redshaw |
| 7,247,717 B2 | 7/2007 | Chen et al. |
| 7,256,267 B2 | 8/2007 | Chen et al. |
| 7,259,296 B2 | 8/2007 | Schmulling et al. |
| 7,262,039 B1 | 8/2007 | Narimatsu et al. |
| 7,262,040 B2 | 8/2007 | Schultz et al. |
| 7,270,815 B2 | 9/2007 | Sasisekharan et al. |
| 7,271,243 B2 | 9/2007 | Dumas Milne Edwards et al. |
| 7,273,706 B2 | 9/2007 | Feder et al. |
| 7,276,354 B2 | 10/2007 | Feder et al. |
| 7,279,310 B2 | 10/2007 | Narimatsu et al. |
| 7,291,491 B2 | 11/2007 | Fukuda et al. |
| 7,297,340 B2 | 11/2007 | Apicella |
| 7,303,905 B2 | 12/2007 | Breves et al. |
| 7,307,159 B2 | 12/2007 | DeAngelis |
| 7,309,600 B2 | 12/2007 | Apicella et al. |
| 7,320,887 B2 | 1/2008 | Kottwitz et al. |
| 7,332,310 B2 | 2/2008 | Nakagawa et al. |
| 7,332,316 B2 | 2/2008 | Schmulling et al. |
| 7,338,799 B2 | 3/2008 | Blakely et al. |
| 7,344,710 B2 | 3/2008 | Dang et al. |
| 7,344,882 B2 | 3/2008 | Lee et al. |
| 7,345,148 B2 | 3/2008 | Feder et al. |
| 7,348,161 B2 | 3/2008 | Gay et al. |
| 7,351,568 B2 | 4/2008 | Dunn-Coleman et al. |
| 7,354,592 B2 | 4/2008 | Bermudes et al. |
| 7,358,074 B2 | 4/2008 | Jackson et al. |
| 7,364,787 B2 | 4/2008 | Ito et al. |
| 7,365,159 B2 | 4/2008 | O'Reilly et al. |
| 7,368,108 B2 | 5/2008 | DeFrees et al. |
| 7,368,284 B2 | 5/2008 | Koike |
| 7,371,559 B2 | 5/2008 | Boone et al. |
| 7,371,838 B2 | 5/2008 | Gilbert et al. |
| 7,378,258 B2 | 5/2008 | Doucette-Stamm et al. |
| 7,378,514 B2 | 5/2008 | Doucette-Stamm et al. |
| 7,381,544 B2 | 6/2008 | Gilbert et al. |
| 7,390,633 B2 | 6/2008 | Liu et al. |
| 7,393,525 B2 | 7/2008 | Powell et al. |
| 7,396,824 B2 | 7/2008 | Sasisekharan et al. |
| 7,404,963 B2 | 7/2008 | Sotomayor et al. |
| 7,407,787 B2 | 8/2008 | Barrangou et al. |
| 7,410,791 B2 | 8/2008 | Singhvi et al. |
| 7,414,119 B2 | 8/2008 | Greenberg et al. |
| 7,429,474 B2 | 9/2008 | Sasisekharan et al. |
| 7,435,808 B2 | 10/2008 | Wu et al. |
| 7,442,523 B2 | 10/2008 | Doucette-Stamm et al. |
| 7,452,531 B2 | 11/2008 | Bermudes et al. |
| 7,459,309 B2 | 12/2008 | Dreyfuss et al. |
| 7,462,482 B2 | 12/2008 | Malik et al. |
| 7,470,667 B2 | 12/2008 | Luo et al. |

(56) References Cited

U.S. PATENT DOCUMENTS

| | | |
|---|---|---|
| 7,485,439 B2 | 2/2009 | Folkman et al. |
| 7,491,529 B2 | 2/2009 | Goddard et al. |
| 7,504,247 B2 | 3/2009 | Sasisekharan et al. |
| 7,510,859 B2 | 3/2009 | Wieland et al. |
| 7,514,089 B2 | 4/2009 | Bermudes et al. |
| 7,544,486 B2 | 6/2009 | Ting et al. |
| 7,569,226 B2 | 8/2009 | Weber et al. |
| 7,569,376 B2 | 8/2009 | Bayer et al. |
| 7,569,384 B2 | 8/2009 | Rosen et al. |
| 7,569,386 B2 | 8/2009 | DeAngelis |
| 7,572,618 B2 | 8/2009 | Mintier et al. |
| 7,582,445 B2 | 9/2009 | Anan et al. |
| 7,588,767 B2 | 9/2009 | Szalay et al. |
| 7,588,771 B2 | 9/2009 | Szalay et al. |
| 7,598,067 B2 | 10/2009 | Beavo et al. |
| 7,611,712 B2 | 11/2009 | Karp |
| 7,611,883 B2 | 11/2009 | Cranenburgh |
| 7,622,564 B2 | 11/2009 | Ge et al. |
| 7,626,000 B2 | 12/2009 | Doucette-Stamm et al. |
| 7,629,150 B2 | 12/2009 | Narimatsu et al. |
| 7,635,598 B2 | 12/2009 | Cook et al. |
| 7,635,765 B2 | 12/2009 | Farnet et al. |
| 7,638,282 B2 | 12/2009 | Bakaletz et al. |
| 7,645,577 B2 | 1/2010 | Adderson et al. |
| 7,655,774 B2 | 2/2010 | Mullins et al. |
| 7,655,781 B2 | 2/2010 | Shemesh et al. |
| 7,662,398 B2 | 2/2010 | Szalay et al. |
| 7,666,419 B2 | 2/2010 | Olson et al. |
| 7,666,627 B2 | 2/2010 | Gal et al. |
| 7,667,018 B2 | 2/2010 | Jakobovits et al. |
| 7,670,835 B2 | 3/2010 | Smith |
| 7,687,474 B2 | 3/2010 | Matin et al. |
| 7,691,383 B2 | 4/2010 | Chakrabarty et al. |
| 7,695,711 B2 | 4/2010 | Myette et al. |
| 7,700,104 B2 | 4/2010 | Hensel et al. |
| 7,700,317 B2 | 4/2010 | Ambrose et al. |
| 7,718,180 B2 | 5/2010 | Karp |
| 7,722,867 B2 | 5/2010 | Umana et al. |
| 7,727,741 B2 | 6/2010 | Umana et al. |
| 7,736,898 B1 | 6/2010 | Fulton et al. |
| 7,740,835 B2 | 6/2010 | Fujimori et al. |
| 7,741,091 B2 | 6/2010 | DeAngelis et al. |
| 7,749,746 B2 | 7/2010 | Raitano et al. |
| 7,754,221 B2 | 7/2010 | Szalay et al. |
| 7,763,250 B2 | 7/2010 | Rosenthal et al. |
| 7,763,420 B2 | 7/2010 | Stritzker et al. |
| 7,771,981 B2 | 8/2010 | DeAngelis |
| 7,776,323 B2 | 8/2010 | Smith |
| 7,786,288 B2 | 8/2010 | Karp |
| 7,790,177 B2 | 9/2010 | Karp |
| 7,803,531 B2 | 9/2010 | Fulton et al. |
| 7,803,604 B2 | 9/2010 | Breves et al. |
| 7,803,923 B2 | 9/2010 | Han et al. |
| 7,807,434 B2 | 10/2010 | Dunn-Coleman et al. |
| 7,807,441 B2 | 10/2010 | Steinaa et al. |
| 7,811,799 B2 | 10/2010 | Dunn-Coleman et al. |
| 7,816,086 B2 | 10/2010 | Bakaletz et al. |
| 7,820,184 B2 | 10/2010 | Stritzker et al. |
| 7,824,894 B2 | 11/2010 | Barrangou et al. |
| 7,824,895 B2 | 11/2010 | Short et al. |
| 7,834,164 B2 | 11/2010 | Sullivan et al. |
| 7,834,166 B2 | 11/2010 | Doucette-Stamm et al. |
| 7,842,290 B2 | 11/2010 | Holden |
| 7,842,492 B2 | 11/2010 | Myette et al. |
| 7,846,706 B2 | 12/2010 | Mintier et al. |
| 7,847,079 B2 | 12/2010 | Rosen et al. |
| 7,867,484 B2 | 1/2011 | Samulski et al. |
| 7,867,732 B2 | 1/2011 | Hori et al. |
| 7,887,816 B2 | 2/2011 | Feldman et al. |
| 7,893,230 B2 | 2/2011 | Doucette-Stamm et al. |
| 7,893,238 B2 | 2/2011 | Doucette-Stamm et al. |
| 7,915,218 B2 | 3/2011 | Capecchi et al. |
| 7,923,221 B1 | 4/2011 | Cabilly et al. |
| 7,939,319 B2 | 5/2011 | Polack et al. |
| 7,951,557 B2 | 5/2011 | Shaaltiel et al. |
| 7,951,560 B2 | 5/2011 | Myette et al. |
| 7,955,600 B2 | 6/2011 | Hensel et al. |
| 7,968,684 B2 | 6/2011 | Ghayur et al. |
| 7,977,080 B2 | 7/2011 | Gramatikova et al. |
| 7,993,905 B2 | 8/2011 | Singhvi et al. |
| 7,998,461 B2 | 8/2011 | Forbes et al. |
| 8,008,283 B2 | 8/2011 | Hochman et al. |
| 8,012,733 B2 | 9/2011 | Van Dijk et al. |
| 8,021,662 B2 | 9/2011 | Szalay et al. |
| 8,021,859 B2 | 9/2011 | Steward et al. |
| 8,029,789 B2 | 10/2011 | Jung et al. |
| 8,030,023 B2 | 10/2011 | Adams et al. |
| 8,043,839 B2 | 10/2011 | Weiner et al. |
| 8,048,646 B2 | 11/2011 | Ting et al. |
| 8,066,987 B2 | 11/2011 | Moore et al. |
| 8,067,179 B2 | 11/2011 | Georgiou et al. |
| 8,067,530 B2 | 11/2011 | O'Keefe et al. |
| 8,093,032 B2 | 1/2012 | Kumar et al. |
| 8,097,436 B2 | 1/2012 | Umana et al. |
| 8,101,168 B2 | 1/2012 | Hassan et al. |
| 8,101,396 B2 | 1/2012 | Sabbadini et al. |
| 8,105,603 B2 | 1/2012 | Kelley et al. |
| 8,105,804 B2 | 1/2012 | Mintier et al. |
| 8,124,729 B2 | 2/2012 | Feder et al. |
| 8,128,940 B2 | 3/2012 | Steward et al. |
| 8,129,166 B2 | 3/2012 | Sabbadini et al. |
| 8,137,904 B2 | 3/2012 | Szalay et al. |
| 8,137,928 B2 | 3/2012 | Schwartz et al. |
| 8,173,397 B2 | 5/2012 | Gal et al. |
| 8,178,319 B2 | 5/2012 | Pahlsson et al. |
| 8,178,339 B2 | 5/2012 | Campbell et al. |
| 8,183,354 B2 | 5/2012 | DeVico et al. |
| 8,198,045 B2 | 6/2012 | DeFrees et al. |
| 8,198,430 B2 | 6/2012 | Prior et al. |
| 8,221,769 B2 | 7/2012 | Szalay et al. |
| 8,227,217 B2 | 7/2012 | Liu et al. |
| 8,227,230 B2 | 7/2012 | Shaaltiel et al. |
| 8,236,494 B2 | 8/2012 | Bakaletz et al. |
| 8,241,623 B1 | 8/2012 | Bermudes |
| 8,257,949 B2 | 9/2012 | Wakarchuk et al. |
| 8,278,065 B2 | 10/2012 | Nicolaides et al. |
| 8,282,919 B2 | 10/2012 | Eisenstark et al. |
| 8,283,114 B2 | 10/2012 | Bakaletz et al. |
| 8,323,959 B2 | 12/2012 | Szalay et al. |
| 8,324,362 B2 | 12/2012 | Chen et al. |
| 8,329,886 B2 | 12/2012 | Bardroff et al. |
| 8,343,509 B2 | 1/2013 | Stritzker et al. |
| 8,354,264 B2 | 1/2013 | Mintier et al. |
| 8,357,486 B2 | 1/2013 | Stritzker et al. |
| 8,372,601 B2 | 2/2013 | Metcalf et al. |
| 8,372,625 B2 | 2/2013 | Walsh et al. |
| 8,383,388 B2 | 2/2013 | Oyhenart et al. |
| 8,394,607 B2 | 3/2013 | Ebens, Jr. et al. |
| 8,409,825 B2 | 4/2013 | Chiba et al. |
| 8,415,118 B2 | 4/2013 | Huang et al. |
| 8,420,350 B2 | 4/2013 | Nakamura et al. |
| 8,426,187 B2 | 4/2013 | Georgiou et al. |
| 8,426,571 B2 | 4/2013 | Raitano et al. |
| 8,435,506 B2 | 5/2013 | Hassan et al. |
| 8,440,207 B2 | 5/2013 | Bermudes |
| 8,445,227 B2 | 5/2013 | Bobrowicz et al. |
| 8,449,876 B2 | 5/2013 | Shaaltiel et al. |
| 8,475,807 B2 | 7/2013 | Perez |
| 8,507,227 B2 | 8/2013 | Samain |
| 8,507,250 B2 | 8/2013 | Liu et al. |
| 8,513,396 B2 | 8/2013 | Boone et al. |
| 8,513,493 B2 | 8/2013 | Baum et al. |
| 8,518,417 B1 | 8/2013 | Steward et al. |
| 8,524,220 B1 | 9/2013 | Bermudes |
| 8,524,484 B2 | 9/2013 | Sabbadini et al. |
| 8,535,909 B2 | 9/2013 | Woldike et al. |
| 8,540,992 B2 | 9/2013 | Naso et al. |
| 8,541,201 B2 | 9/2013 | Min et al. |
| 8,551,471 B2 | 10/2013 | Filutowicz et al. |
| 8,568,707 B2 | 10/2013 | Szalay et al. |
| 8,569,016 B2 | 10/2013 | Obayashi et al. |
| 8,575,316 B2 | 11/2013 | Hiruma et al. |
| 8,586,022 B2 | 11/2013 | Szalay et al. |
| 8,586,332 B2 | 11/2013 | Samain et al. |

(56) References Cited

U.S. PATENT DOCUMENTS

| | | |
|---|---|---|
| 8,591,862 B2 | 11/2013 | Brahmbhatt et al. |
| 8,604,004 B2 | 12/2013 | Kahne et al. |
| 8,604,178 B2 | 12/2013 | Bottje et al. |
| 8,623,350 B1 | 1/2014 | Bermudes |
| 8,623,999 B2 | 1/2014 | Steward et al. |
| 8,628,917 B2 | 1/2014 | Bakaletz et al. |
| 8,632,995 B2 | 1/2014 | Sun et al. |
| 8,642,257 B2 | 2/2014 | Szalay et al. |
| 8,642,292 B2 | 2/2014 | Sandig et al. |
| 8,647,642 B2 | 2/2014 | Bermudes |
| 8,652,773 B2 | 2/2014 | Bakaletz et al. |
| 8,652,808 B2 | 2/2014 | Jennewein et al. |
| 8,652,838 B2 | 2/2014 | Shen et al. |
| 8,663,634 B2 | 3/2014 | Koenig et al. |
| 8,674,062 B2 | 3/2014 | Dunn-Coleman et al. |
| 8,674,083 B2 | 3/2014 | Presta |
| 8,680,236 B2 | 3/2014 | Luft et al. |
| 8,685,939 B2 | 4/2014 | Wei et al. |
| 8,697,398 B2 | 4/2014 | Doherty et al. |
| 8,697,414 B2 | 4/2014 | Steward et al. |
| 8,703,153 B2 | 4/2014 | Telfer et al. |
| 8,703,471 B2 | 4/2014 | Aebi et al. |
| 8,715,641 B2 | 5/2014 | Filutowicz et al. |
| 8,716,450 B2 | 5/2014 | Ghayur et al. |
| 8,722,618 B2 | 5/2014 | Jacobs et al. |
| 8,722,668 B2 | 5/2014 | Hochman |
| 8,722,855 B2 | 5/2014 | Ghayur et al. |
| 8,722,869 B2 | 5/2014 | Fang et al. |
| 8,734,779 B2 | 5/2014 | Hamaji et al. |
| 8,734,814 B2 | 5/2014 | Datta et al. |
| 8,735,546 B2 | 5/2014 | Ghayur et al. |
| 8,741,620 B2 | 6/2014 | Shaaltiel et al. |
| 8,759,494 B2 | 6/2014 | Bachmann et al. |
| 8,771,669 B1 | 7/2014 | Bermudes |
| 8,771,991 B2 | 7/2014 | Gilbert et al. |
| 8,784,836 B2 | 7/2014 | Szalay et al. |
| 8,790,641 B2 | 7/2014 | Shaaltiel et al. |
| 8,815,558 B2 | 8/2014 | Frost et al. |
| RE45,170 E | 9/2014 | Smith |
| 8,822,194 B2 | 9/2014 | Zhao et al. |
| 8,822,645 B2 | 9/2014 | Ghayur et al. |
| 8,822,664 B2 | 9/2014 | Cicortas Gunnarsson et al. |
| 8,828,681 B2 | 9/2014 | Bell, III et al. |
| 8,835,162 B2 | 9/2014 | Kwon et al. |
| 8,846,363 B2 | 9/2014 | Myette et al. |
| 8,853,154 B2 | 10/2014 | Cload et al. |
| 8,871,491 B2 | 10/2014 | Wacker et al. |
| 8,907,071 B2 | 12/2014 | Sullivan et al. |
| 8,920,798 B2 | 12/2014 | Han et al. |
| 8,932,598 B2 | 1/2015 | Song et al. |
| 8,956,859 B1 | 2/2015 | Bermudes |
| 8,962,275 B2 | 2/2015 | Liang et al. |
| 8,969,538 B2 | 3/2015 | Rosen et al. |
| 8,975,040 B2 | 3/2015 | Naso et al. |
| 8,993,265 B2 | 3/2015 | Cload et al. |
| 8,993,297 B2 | 3/2015 | Ronin et al. |
| 9,005,949 B2 | 4/2015 | Oxvig et al. |
| 9,012,186 B2 | 4/2015 | Cann et al. |
| 9,017,986 B2 | 4/2015 | Sabbadini et al. |
| 9,023,635 B2 | 5/2015 | Bayer et al. |
| 9,029,136 B2 | 5/2015 | Heidtman et al. |
| 9,029,508 B2 | 5/2015 | Ghayur et al. |
| 9,034,642 B2 | 5/2015 | Bakaletz et al. |
| 9,068,187 B1 | 6/2015 | Bermudes |
| 9,200,251 B1 | 12/2015 | Bermudes |
| 9,200,289 B1 | 12/2015 | Bermudes |
| 9,315,817 B2 | 4/2016 | Bermudes |
| 9,365,625 B1 | 6/2016 | Bermudes |
| 9,421,252 B2 | 8/2016 | Bermudes |
| 9,486,513 B1 | 11/2016 | Bermudes |
| 9,616,114 B1 | 4/2017 | Bermudes |
| 10,286,051 B1 | 5/2019 | Bermudes |
| 10,449,237 B1 | 10/2019 | Bermudes |
| 2001/0041333 A1 | 11/2001 | Short et al. |
| 2002/0026655 A1 | 2/2002 | Bermudes et al. |
| 2002/0032323 A1 | 3/2002 | Kunsch et al. |
| 2002/0042382 A1 | 4/2002 | Duffy et al. |
| 2002/0061545 A1 | 5/2002 | Choi et al. |
| 2002/0072104 A1 | 6/2002 | Landry |
| 2002/0102242 A1 | 8/2002 | Briles et al. |
| 2002/0103338 A1 | 8/2002 | Choi |
| 2002/0120116 A1 | 8/2002 | Kunsch et al. |
| 2002/0127702 A1 | 9/2002 | Bernstein et al. |
| 2002/0151063 A1 | 10/2002 | Lasham et al. |
| 2002/0155519 A1 | 10/2002 | Lindner et al. |
| 2002/0176848 A1 | 11/2002 | Sizemore et al. |
| 2003/0008839 A1 | 1/2003 | van Rooij et al. |
| 2003/0009015 A1 | 1/2003 | Ulrich et al. |
| 2003/0022835 A1 | 1/2003 | Watson et al. |
| 2003/0031628 A1 | 2/2003 | Zhao et al. |
| 2003/0031683 A1 | 2/2003 | Curtiss et al. |
| 2003/0036644 A1 | 2/2003 | Ulrich |
| 2003/0045492 A1 | 3/2003 | Tang et al. |
| 2003/0049648 A1 | 3/2003 | Choi |
| 2003/0059400 A1 | 3/2003 | Szalay |
| 2003/0059923 A1 | 3/2003 | Feder et al. |
| 2003/0077677 A1 | 4/2003 | Short et al. |
| 2003/0092164 A1 | 5/2003 | Gross et al. |
| 2003/0100071 A1 | 5/2003 | Apicella et al. |
| 2003/0100108 A1 | 5/2003 | Altman et al. |
| 2003/0100488 A1 | 5/2003 | Boyle |
| 2003/0103958 A1 | 6/2003 | Short et al. |
| 2003/0109026 A1 | 6/2003 | Bermudes et al. |
| 2003/0113293 A1 | 6/2003 | Bermudes et al. |
| 2003/0113343 A1 | 6/2003 | Tuomanen et al. |
| 2003/0125278 A1 | 7/2003 | Tang et al. |
| 2003/0143676 A1 | 7/2003 | Strachan et al. |
| 2003/0153527 A1 | 8/2003 | Powell et al. |
| 2003/0166541 A1 | 9/2003 | Ruben et al. |
| 2003/0170211 A1 | 9/2003 | Goudsmit et al. |
| 2003/0170276 A1 | 9/2003 | Bermudes et al. |
| 2003/0194798 A1 | 10/2003 | Surber et al. |
| 2003/0207271 A1 | 11/2003 | Holwitt et al. |
| 2003/0211599 A1 | 11/2003 | Sabbadini et al. |
| 2004/0005695 A1 | 1/2004 | Miksch et al. |
| 2004/0005700 A1 | 1/2004 | Surber et al. |
| 2004/0009490 A1 | 1/2004 | Glenn et al. |
| 2004/0009936 A1 | 1/2004 | Tang et al. |
| 2004/0014177 A1 | 1/2004 | Navran, Jr. et al. |
| 2004/0022805 A1 | 2/2004 | Narum et al. |
| 2004/0023266 A1 | 2/2004 | Vivekananda et al. |
| 2004/0054142 A1 | 3/2004 | Cassart et al. |
| 2004/0058849 A1 | 3/2004 | Sleeman et al. |
| 2004/0071729 A1 | 4/2004 | Adderson et al. |
| 2004/0077540 A1 | 4/2004 | Quay |
| 2004/0082002 A1 | 4/2004 | Choi |
| 2004/0091969 A1 | 5/2004 | Agarwal et al. |
| 2004/0101932 A1 | 5/2004 | Naleway et al. |
| 2004/0106185 A1 | 6/2004 | Ranganathan |
| 2004/0115174 A1 | 6/2004 | Gilboa et al. |
| 2004/0171123 A1 | 9/2004 | Rosen et al. |
| 2004/0202648 A1 | 10/2004 | Cabezon et al. |
| 2004/0202663 A1 | 10/2004 | Hu et al. |
| 2004/0219169 A1 | 11/2004 | Bermudes et al. |
| 2004/0229338 A1 | 11/2004 | King |
| 2004/0234455 A1 | 11/2004 | Szalay |
| 2004/0266003 A1 | 12/2004 | Powell et al. |
| 2005/0003400 A1 | 1/2005 | Boyle |
| 2005/0008618 A1 | 1/2005 | Kaufman et al. |
| 2005/0009750 A1 | 1/2005 | Sleeman et al. |
| 2005/0026866 A1 | 2/2005 | Pawelek |
| 2005/0036987 A1 | 2/2005 | Pawelek et al. |
| 2005/0059122 A1 | 3/2005 | Shen |
| 2005/0064526 A1 | 3/2005 | Ulrich et al. |
| 2005/0069491 A1 | 3/2005 | Szalay et al. |
| 2005/0070005 A1 | 3/2005 | Keller |
| 2005/0089552 A1 | 4/2005 | Altman et al. |
| 2005/0106597 A1 | 5/2005 | Choi |
| 2005/0112139 A1 | 5/2005 | Karp |
| 2005/0112140 A1 | 5/2005 | Karp |
| 2005/0112642 A1 | 5/2005 | Sleeman et al. |
| 2005/0112751 A1 | 5/2005 | Fang et al. |
| 2005/0118193 A1 | 6/2005 | Andino-Pavlovsky et al. |
| 2005/0136404 A1 | 6/2005 | Doucette-Stamm et al. |

(56) References Cited

U.S. PATENT DOCUMENTS

| | | |
|---|---|---|
| 2005/0147590 A1 | 7/2005 | Sabbadini et al. |
| 2005/0181439 A1 | 8/2005 | Choi et al. |
| 2005/0214317 A1 | 9/2005 | Karp |
| 2005/0214318 A1 | 9/2005 | Karp |
| 2005/0221439 A1 | 10/2005 | Bakaletz et al. |
| 2005/0249706 A1 | 11/2005 | Bermudes et al. |
| 2005/0250196 A1 | 11/2005 | Paton et al. |
| 2005/0255088 A1 | 11/2005 | Bermudes et al. |
| 2005/0267103 A1 | 12/2005 | Hochman |
| 2005/0287639 A1 | 12/2005 | Kwon et al. |
| 2006/0008465 A1 | 1/2006 | Steinaa et al. |
| 2006/0025387 A1 | 2/2006 | Hochman |
| 2006/0035813 A1 | 2/2006 | Sternberg et al. |
| 2006/0051839 A1 | 3/2006 | Robinson et al. |
| 2006/0057152 A1 | 3/2006 | Marshall |
| 2006/0073168 A1 | 4/2006 | Stephens et al. |
| 2006/0083716 A1 | 4/2006 | Kaufman et al. |
| 2006/0089350 A1 | 4/2006 | Hochman et al. |
| 2006/0104955 A1 | 5/2006 | Redshaw |
| 2006/0115483 A1 | 6/2006 | Sleeman et al. |
| 2006/0127408 A1 | 6/2006 | Young et al. |
| 2006/0140975 A1 | 6/2006 | Curtiss et al. |
| 2006/0167229 A1 | 7/2006 | Wong et al. |
| 2006/0234943 A1 | 10/2006 | Wong |
| 2006/0270043 A1 | 11/2006 | Blattner et al. |
| 2006/0281908 A1 | 12/2006 | Callen |
| 2007/0004666 A1 | 1/2007 | Lasham et al. |
| 2007/0009489 A1 | 1/2007 | Bermudes et al. |
| 2007/0009900 A1 | 1/2007 | Doucette-Stamm et al. |
| 2007/0009901 A1 | 1/2007 | Doucette-Stamm et al. |
| 2007/0009902 A1 | 1/2007 | Doucette-Stamm et al. |
| 2007/0009903 A1 | 1/2007 | Doucette-Stamm et al. |
| 2007/0009904 A1 | 1/2007 | Doucette-Stamm et al. |
| 2007/0009905 A1 | 1/2007 | Doucette-Stamm et al. |
| 2007/0009906 A1 | 1/2007 | Doucette-Stamm et al. |
| 2007/0009932 A1 | 1/2007 | Stephanopoulos et al. |
| 2007/0015271 A1 | 1/2007 | Rosen et al. |
| 2007/0026507 A1 | 2/2007 | Olivo et al. |
| 2007/0031382 A1 | 2/2007 | Powell et al. |
| 2007/0031852 A1 | 2/2007 | Doucette-Stamm et al. |
| 2007/0059801 A1 | 3/2007 | Doucette-Stamm et al. |
| 2007/0059802 A1 | 3/2007 | Doucette-Stamm et al. |
| 2007/0065820 A1 | 3/2007 | Jiang et al. |
| 2007/0071675 A1 | 3/2007 | Wu et al. |
| 2007/0104689 A1 | 5/2007 | Gillies et al. |
| 2007/0110721 A1 | 5/2007 | Cranenburgh |
| 2007/0110752 A1 | 5/2007 | Murison et al. |
| 2007/0116671 A1 | 5/2007 | Prakash et al. |
| 2007/0122881 A1 | 5/2007 | Surber |
| 2007/0134264 A1 | 6/2007 | Marshall |
| 2007/0154986 A1 | 7/2007 | Kunsch et al. |
| 2007/0178116 A1 | 8/2007 | Adderson et al. |
| 2007/0178492 A1 | 8/2007 | Gross et al. |
| 2007/0178505 A1 | 8/2007 | Fischer et al. |
| 2007/0184517 A1 | 8/2007 | Schultz et al. |
| 2007/0184528 A1 | 8/2007 | Pierce et al. |
| 2007/0184543 A1 | 8/2007 | Pierce et al. |
| 2007/0191262 A1 | 8/2007 | Racila et al. |
| 2007/0202578 A1 | 8/2007 | Samain et al. |
| 2007/0202591 A1 | 8/2007 | Ulrich |
| 2007/0212311 A1 | 9/2007 | Burne et al. |
| 2007/0231820 A1 | 10/2007 | Weiner et al. |
| 2007/0244047 A1 | 10/2007 | Rosen et al. |
| 2007/0254846 A1 | 11/2007 | Wong et al. |
| 2007/0264689 A1 | 11/2007 | Gross et al. |
| 2007/0269369 A1 | 11/2007 | Gegg et al. |
| 2007/0281342 A1 | 12/2007 | DeAngelis |
| 2007/0287171 A1 | 12/2007 | Inouye |
| 2007/0298012 A1 | 12/2007 | King et al. |
| 2007/0299008 A1 | 12/2007 | Rummel |
| 2008/0004206 A1 | 1/2008 | Rosen et al. |
| 2008/0009446 A1 | 1/2008 | Yu et al. |
| 2008/0031877 A1 | 2/2008 | Covacci et al. |
| 2008/0038296 A1 | 2/2008 | Brahmbhatt et al. |
| 2008/0064062 A1 | 3/2008 | Leonhartsberger et al. |
| 2008/0070840 A1 | 3/2008 | Min et al. |
| 2008/0076157 A1 | 3/2008 | Leonhartsberger et al. |
| 2008/0102115 A1 | 5/2008 | Oyhenart et al. |
| 2008/0124355 A1 | 5/2008 | Bermudes |
| 2008/0166757 A1 | 7/2008 | Bron et al. |
| 2008/0166764 A1 | 7/2008 | Schloesser et al. |
| 2008/0171014 A1 | 7/2008 | Wu et al. |
| 2008/0182295 A1 | 7/2008 | Patkar et al. |
| 2008/0187520 A1 | 8/2008 | Polack et al. |
| 2008/0193974 A1 | 8/2008 | Coleman et al. |
| 2008/0194481 A1 | 8/2008 | Rosen et al. |
| 2008/0206284 A1 | 8/2008 | Williams et al. |
| 2008/0206814 A1 | 8/2008 | Lee et al. |
| 2008/0206818 A1 | 8/2008 | Wich et al. |
| 2008/0213316 A1 | 9/2008 | Tarasenko |
| 2008/0214469 A1 | 9/2008 | Lam et al. |
| 2008/0227704 A1 | 9/2008 | Kamens |
| 2008/0242620 A1 | 10/2008 | Wong et al. |
| 2008/0249013 A1 | 10/2008 | Cabezon et al. |
| 2008/0254511 A1 | 10/2008 | Dassler et al. |
| 2008/0260769 A1 | 10/2008 | Capecchi et al. |
| 2008/0274155 A1 | 11/2008 | Barton et al. |
| 2008/0280346 A1 | 11/2008 | de Lorenzo Prieto et al. |
| 2008/0311081 A1 | 12/2008 | Fruehauf et al. |
| 2008/0311125 A1 | 12/2008 | O'Keefe et al. |
| 2008/0317731 A1 | 12/2008 | Gramatikova et al. |
| 2009/0004744 A1 | 1/2009 | Surber et al. |
| 2009/0010956 A1 | 1/2009 | Rikihisa |
| 2009/0011490 A1 | 1/2009 | Sabbadini et al. |
| 2009/0011995 A1 | 1/2009 | Lee et al. |
| 2009/0028890 A1 | 1/2009 | Karp |
| 2009/0035827 A1 | 2/2009 | Stephens et al. |
| 2009/0042785 A1 | 2/2009 | Matschiner et al. |
| 2009/0053186 A1 | 2/2009 | Hu et al. |
| 2009/0054323 A1 | 2/2009 | Oliner et al. |
| 2009/0062139 A1 | 3/2009 | Short et al. |
| 2009/0068226 A1 | 3/2009 | Ulrich et al. |
| 2009/0069241 A1 | 3/2009 | Barnstable et al. |
| 2009/0081193 A1 | 3/2009 | Sasisekharan et al. |
| 2009/0081673 A1 | 3/2009 | Shen et al. |
| 2009/0092632 A1 | 4/2009 | Lee |
| 2009/0117047 A1 | 5/2009 | Szalay et al. |
| 2009/0117048 A1 | 5/2009 | Szalay et al. |
| 2009/0117049 A1 | 5/2009 | Szalay et al. |
| 2009/0123382 A1 | 5/2009 | Szalay et al. |
| 2009/0123426 A1 | 5/2009 | Li et al. |
| 2009/0123921 A1 | 5/2009 | Georgiou et al. |
| 2009/0130709 A1 | 5/2009 | Hamilton |
| 2009/0136542 A1 | 5/2009 | Karp |
| 2009/0142343 A1 | 6/2009 | Fuh et al. |
| 2009/0155238 A1 | 6/2009 | Weiner et al. |
| 2009/0169517 A1 | 7/2009 | Bermudes et al. |
| 2009/0170155 A1 | 7/2009 | Johnson et al. |
| 2009/0175829 A1 | 7/2009 | Forbes et al. |
| 2009/0175897 A1 | 7/2009 | Tang et al. |
| 2009/0180955 A1 | 7/2009 | Stritzker et al. |
| 2009/0186377 A1 | 7/2009 | Johnson et al. |
| 2009/0203103 A1 | 8/2009 | Pierce et al. |
| 2009/0208534 A1 | 8/2009 | Xu et al. |
| 2009/0215754 A1 | 8/2009 | Hochman et al. |
| 2009/0220480 A1 | 9/2009 | Gray et al. |
| 2009/0220540 A1 | 9/2009 | Marshall |
| 2009/0232801 A1 | 9/2009 | Hillen et al. |
| 2009/0238789 A1 | 9/2009 | Guyon et al. |
| 2009/0246832 A1 | 10/2009 | Wakarchuk et al. |
| 2009/0271894 A1 | 10/2009 | Benfey et al. |
| 2009/0300779 A1 | 12/2009 | Zhao et al. |
| 2009/0304693 A1 | 12/2009 | Ghayur et al. |
| 2009/0311253 A1 | 12/2009 | Ghayur et al. |
| 2009/0311744 A1 | 12/2009 | DeFrees et al. |
| 2009/0317404 A1 | 12/2009 | Markham |
| 2009/0324576 A1 | 12/2009 | Padmanabhan et al. |
| 2009/0325298 A1 | 12/2009 | Kernodle |
| 2009/0325866 A1 | 12/2009 | Kim et al. |
| 2010/0008851 A1 | 1/2010 | Nicolaides et al. |
| 2010/0011456 A1 | 1/2010 | Mathur et al. |
| 2010/0028340 A1 | 2/2010 | Mueller et al. |
| 2010/0040537 A1 | 2/2010 | Gu et al. |
| 2010/0040640 A1 | 2/2010 | Lanar et al. |

(56) References Cited

U.S. PATENT DOCUMENTS

| | | |
|---|---|---|
| 2010/0047239 A1 | 2/2010 | Wu et al. |
| 2010/0047245 A1 | 2/2010 | Lacy et al. |
| 2010/0068173 A1 | 3/2010 | Yu et al. |
| 2010/0074900 A1 | 3/2010 | Ghayur et al. |
| 2010/0074933 A1 | 3/2010 | Prakash et al. |
| 2010/0080815 A1 | 4/2010 | Zavada et al. |
| 2010/0092438 A1 | 4/2010 | Fruehauf et al. |
| 2010/0095398 A1 | 4/2010 | Meana et al. |
| 2010/0105106 A1 | 4/2010 | Ronin et al. |
| 2010/0112670 A1 | 5/2010 | Giacalone et al. |
| 2010/0119550 A1 | 5/2010 | Gomi et al. |
| 2010/0119588 A1 | 5/2010 | Sato et al. |
| 2010/0124558 A1 | 5/2010 | Curtiss, III et al. |
| 2010/0135961 A1 | 6/2010 | Bermudes |
| 2010/0135973 A1 | 6/2010 | Eisenstark et al. |
| 2010/0136027 A1 | 6/2010 | Kim |
| 2010/0136048 A1 | 6/2010 | Bermudes |
| 2010/0136657 A1 | 6/2010 | Jokinen et al. |
| 2010/0158952 A1 | 6/2010 | Goletz |
| 2010/0160612 A1 | 6/2010 | Skerra et al. |
| 2010/0172976 A1 | 7/2010 | Satishchandran et al. |
| 2010/0183516 A1 | 7/2010 | Ribbert et al. |
| 2010/0189686 A1 | 7/2010 | Rosen et al. |
| 2010/0189691 A1 | 7/2010 | Fruehauf et al. |
| 2010/0189740 A1 | 7/2010 | Michon et al. |
| 2010/0196315 A1 | 8/2010 | Lacy et al. |
| 2010/0209405 A1 | 8/2010 | Altman et al. |
| 2010/0216720 A1 | 8/2010 | Brophy et al. |
| 2010/0221179 A1 | 9/2010 | Hsieh et al. |
| 2010/0221779 A1 | 9/2010 | Short et al. |
| 2010/0233079 A1 | 9/2010 | Jakob et al. |
| 2010/0233195 A1 | 9/2010 | Delisa et al. |
| 2010/0239546 A1 | 9/2010 | Fruehauf et al. |
| 2010/0249026 A1 | 9/2010 | Rosen et al. |
| 2010/0255036 A1 | 10/2010 | Hassan et al. |
| 2010/0260668 A1 | 10/2010 | Ghayur et al. |
| 2010/0281577 A1 | 11/2010 | Mulet Salort et al. |
| 2010/0285564 A1 | 11/2010 | Skerra et al. |
| 2010/0286060 A1 | 11/2010 | Oliner et al. |
| 2010/0291033 A1 | 11/2010 | Rosen et al. |
| 2010/0291088 A1 | 11/2010 | Ghayur et al. |
| 2010/0310593 A1 | 12/2010 | Brazer et al. |
| 2011/0008828 A1 | 1/2011 | Kwon et al. |
| 2011/0027349 A1 | 2/2011 | Sable et al. |
| 2011/0044980 A1 | 2/2011 | Ghayur et al. |
| 2011/0045587 A1 | 2/2011 | Sullivan et al. |
| 2011/0091372 A1 | 4/2011 | Ghayur et al. |
| 2011/0091463 A1 | 4/2011 | Ghayur et al. |
| 2011/0091493 A1 | 4/2011 | Moahamadzadeh et al. |
| 2011/0093965 A1 | 4/2011 | O'Donoghue et al. |
| 2011/0104163 A1 | 5/2011 | Dimitrov et al. |
| 2011/0104196 A1 | 5/2011 | Karp |
| 2011/0104240 A1 | 5/2011 | Jones et al. |
| 2011/0106000 A1 | 5/2011 | Jones et al. |
| 2011/0111481 A1 | 5/2011 | Li |
| 2011/0111496 A1 | 5/2011 | Li |
| 2011/0117079 A1 | 5/2011 | Benatuil et al. |
| 2011/0117617 A1 | 5/2011 | Liu et al. |
| 2011/0136759 A1 | 6/2011 | Kahne et al. |
| 2011/0142761 A1 | 6/2011 | Wu et al. |
| 2011/0165063 A1 | 7/2011 | Hsieh et al. |
| 2011/0165066 A1 | 7/2011 | Wu et al. |
| 2011/0165680 A1 | 7/2011 | Blattner et al. |
| 2011/0189773 A1 | 8/2011 | Altman et al. |
| 2011/0195090 A1 | 8/2011 | Dimitrov |
| 2011/0206616 A1 | 8/2011 | Ichtchenko et al. |
| 2011/0212094 A1 | 9/2011 | Ghayur et al. |
| 2011/0217237 A1 | 9/2011 | Chen et al. |
| 2011/0223241 A1 | 9/2011 | Tardi et al. |
| 2011/0243980 A1 | 10/2011 | Feldman et al. |
| 2011/0243992 A1 | 10/2011 | Kernodle |
| 2011/0268661 A1 | 11/2011 | Markiv et al. |
| 2011/0274719 A1 | 11/2011 | Marshall |
| 2011/0275122 A1 | 11/2011 | Min et al. |
| 2011/0275585 A1 | 11/2011 | Brahmbhatt et al. |
| 2011/0280800 A1 | 11/2011 | Wu et al. |
| 2011/0280830 A9 | 11/2011 | Rosen et al. |
| 2011/0281330 A1 | 11/2011 | Sabbadini et al. |
| 2011/0286916 A1 | 11/2011 | Aste-Amezaga et al. |
| 2011/0318308 A1 | 12/2011 | Ragolia |
| 2011/0318316 A1 | 12/2011 | Wong et al. |
| 2011/0318317 A1 | 12/2011 | Wong et al. |
| 2011/0318349 A1 | 12/2011 | Ghayur et al. |
| 2012/0009194 A1 | 1/2012 | Ferrone et al. |
| 2012/0009196 A1 | 1/2012 | Muerhoff et al. |
| 2012/0009205 A1 | 1/2012 | Gegg et al. |
| 2012/0014941 A1 | 1/2012 | Wu et al. |
| 2012/0014957 A1 | 1/2012 | Ghayur et al. |
| 2012/0020883 A1 | 1/2012 | Stritzker et al. |
| 2012/0021517 A1 | 1/2012 | Jin et al. |
| 2012/0021985 A1 | 1/2012 | Rosen et al. |
| 2012/0034160 A1 | 2/2012 | Ghayur et al. |
| 2012/0064568 A1 | 3/2012 | Hamilton |
| 2012/0076758 A1 | 3/2012 | Diamond et al. |
| 2012/0076803 A1 | 3/2012 | Brophy et al. |
| 2012/0083587 A1 | 4/2012 | Gallo et al. |
| 2012/0087858 A1 | 4/2012 | Ghayur et al. |
| 2012/0093773 A1 | 4/2012 | Li et al. |
| 2012/0093805 A1 | 4/2012 | Kubota |
| 2012/0094906 A1 | 4/2012 | Guyon et al. |
| 2012/0100140 A1 | 4/2012 | Reyes et al. |
| 2012/0100581 A1 | 4/2012 | Gramatikova et al. |
| 2012/0107360 A1 | 5/2012 | Le Butt et al. |
| 2012/0108521 A1 | 5/2012 | Eggink et al. |
| 2012/0108640 A1 | 5/2012 | Hochman et al. |
| 2012/0114652 A1 | 5/2012 | Elvin et al. |
| 2012/0121637 A1 | 5/2012 | Granoff et al. |
| 2012/0122762 A1 | 5/2012 | Ruben et al. |
| 2012/0122962 A1 | 5/2012 | Han et al. |
| 2012/0128594 A1 | 5/2012 | Choy et al. |
| 2012/0128624 A1 | 5/2012 | Yu et al. |
| 2012/0128718 A1 | 5/2012 | Hassan et al. |
| 2012/0135503 A1 | 5/2012 | Sabbadini et al. |
| 2012/0141415 A1 | 6/2012 | Ballance et al. |
| 2012/0142079 A1 | 6/2012 | Sabbadini et al. |
| 2012/0142080 A1 | 6/2012 | Bermudes |
| 2012/0144509 A1 | 6/2012 | Benghezal et al. |
| 2012/0148601 A1 | 6/2012 | Ulrich et al. |
| 2012/0164687 A1 | 6/2012 | Bereta et al. |
| 2012/0171234 A1 | 7/2012 | Wong et al. |
| 2012/0177682 A1 | 7/2012 | Marshall |
| 2012/0189541 A1 | 7/2012 | Wu |
| 2012/0189572 A1 | 7/2012 | Wei et al. |
| 2012/0195900 A1 | 8/2012 | Ghayur et al. |
| 2012/0195922 A1 | 8/2012 | Lee |
| 2012/0208181 A1 | 8/2012 | Merighi et al. |
| 2012/0210467 A1 | 8/2012 | Barton et al. |
| 2012/0213767 A1 | 8/2012 | Wei et al. |
| 2012/0225454 A1 | 9/2012 | Benghezal et al. |
| 2012/0232012 A1 | 9/2012 | Popel et al. |
| 2012/0237491 A1 | 9/2012 | Padmanabhan et al. |
| 2012/0244600 A1 | 9/2012 | Jin |
| 2012/0244621 A1 | 9/2012 | Weiss et al. |
| 2012/0252099 A1 | 10/2012 | Sabbadini et al. |
| 2012/0253009 A1 | 10/2012 | Walker |
| 2012/0258108 A1 | 10/2012 | Ghayur et al. |
| 2012/0258521 A1 | 10/2012 | Liu et al. |
| 2012/0263722 A1 | 10/2012 | Ghayur et al. |
| 2012/0264686 A9 | 10/2012 | Guyon et al. |
| 2012/0266328 A1 | 10/2012 | Gray et al. |
| 2012/0266329 A1 | 10/2012 | Mathur et al. |
| 2012/0275996 A1 | 11/2012 | Hsieh |
| 2012/0277143 A1 | 11/2012 | Jacobs et al. |
| 2012/0282700 A1 | 11/2012 | Lunder et al. |
| 2012/0301493 A1 | 11/2012 | Brandariz Nunez et al. |
| 2012/0301497 A1 | 11/2012 | Yadava et al. |
| 2012/0308594 A1 | 12/2012 | Sablon et al. |
| 2012/0329150 A1 | 12/2012 | Duke et al. |
| 2013/0004416 A1 | 1/2013 | Wu et al. |
| 2013/0011409 A1 | 1/2013 | Shipp et al. |
| 2013/0022539 A1 | 1/2013 | Pilkington et al. |
| 2013/0022578 A1 | 1/2013 | Newman et al. |
| 2013/0045184 A1 | 2/2013 | Teitelbaum |
| 2013/0059318 A1 | 3/2013 | Kaneko et al. |

(56) References Cited

U.S. PATENT DOCUMENTS

| | | |
|---|---|---|
| 2013/0065274 A1 | 3/2013 | Gerngross et al. |
| 2013/0078275 A1 | 3/2013 | Tao |
| 2013/0101577 A9 | 4/2013 | Wei et al. |
| 2013/0122565 A1 | 5/2013 | Pierce et al. |
| 2013/0129737 A1 | 5/2013 | Adderson et al. |
| 2013/0129761 A1 | 5/2013 | Garcia-Sastre et al. |
| 2013/0130292 A1 | 5/2013 | Szalay et al. |
| 2013/0149313 A1 | 6/2013 | Gu et al. |
| 2013/0164307 A1 | 6/2013 | Markham |
| 2013/0164317 A1 | 6/2013 | Yousef et al. |
| 2013/0164329 A1 | 6/2013 | Rossomando et al. |
| 2013/0164380 A1 | 6/2013 | Durum et al. |
| 2013/0171096 A1 | 7/2013 | Hsieh et al. |
| 2013/0171182 A1 | 7/2013 | Whelan et al. |
| 2013/0171190 A1 | 7/2013 | Curtiss, III et al. |
| 2013/0177555 A1 | 7/2013 | Wilkinson et al. |
| 2013/0190241 A1 | 7/2013 | Wong et al. |
| 2013/0190255 A1 | 7/2013 | Wong et al. |
| 2013/0197194 A1 | 8/2013 | Kaplan et al. |
| 2013/0197203 A1 | 8/2013 | Michon et al. |
| 2013/0202623 A1 | 8/2013 | Chomont et al. |
| 2013/0203164 A1 | 8/2013 | Rosen et al. |
| 2013/0205416 A1 | 8/2013 | Nash et al. |
| 2013/0209405 A1 | 8/2013 | Curtiss et al. |
| 2013/0209407 A1 | 8/2013 | Hamer |
| 2013/0209499 A1 | 8/2013 | Garcia-Sastre et al. |
| 2013/0210073 A1 | 8/2013 | Kwon et al. |
| 2013/0210077 A1 | 8/2013 | Brzezinski et al. |
| 2013/0210121 A1 | 8/2013 | Giacalone et al. |
| 2013/0210149 A1 | 8/2013 | Li |
| 2013/0210747 A1 | 8/2013 | Hamm-Alvarez et al. |
| 2013/0216555 A1 | 8/2013 | Nitsch et al. |
| 2013/0216568 A1 | 8/2013 | Maione et al. |
| 2013/0217068 A1 | 8/2013 | Parkot et al. |
| 2013/0217145 A1 | 8/2013 | Yoshimura et al. |
| 2013/0227741 A1 | 8/2013 | Gray et al. |
| 2013/0243747 A1 | 9/2013 | Fima et al. |
| 2013/0266585 A1 | 10/2013 | Nitsch et al. |
| 2013/0274187 A1 | 10/2013 | Mogelsvang et al. |
| 2013/0287810 A1 | 10/2013 | Mohamadzadeh et al. |
| 2013/0295054 A1 | 11/2013 | Huang et al. |
| 2013/0295072 A1 | 11/2013 | Fima et al. |
| 2013/0318640 A1 | 11/2013 | Oldenburg et al. |
| 2013/0323801 A1 | 12/2013 | Chilton et al. |
| 2013/0330350 A1 | 12/2013 | Dimasi |
| 2013/0330824 A1 | 12/2013 | Li |
| 2013/0337516 A1 | 12/2013 | Herrema |
| 2013/0337545 A1 | 12/2013 | Sabbadini et al. |
| 2013/0345114 A1 | 12/2013 | Williams et al. |
| 2014/0010811 A1 | 1/2014 | Ferrone et al. |
| 2014/0010829 A1 | 1/2014 | Bigner et al. |
| 2014/0024050 A1 | 1/2014 | Yoshimura et al. |
| 2014/0024820 A1 | 1/2014 | Parkot et al. |
| 2014/0031541 A1 | 1/2014 | Heidtman et al. |
| 2014/0044748 A1 | 2/2014 | Lee |
| 2014/0045261 A1 | 2/2014 | Wang et al. |
| 2014/0050693 A1 | 2/2014 | Skerra et al. |
| 2014/0072595 A1 | 3/2014 | Benghezal et al. |
| 2014/0073683 A1 | 3/2014 | Han et al. |
| 2014/0079701 A1 | 3/2014 | Miller et al. |
| 2014/0080201 A1 | 3/2014 | Merighi et al. |
| 2014/0086950 A1 | 3/2014 | Pascual et al. |
| 2014/0093521 A1 | 4/2014 | Benatuil et al. |
| 2014/0093540 A1 | 4/2014 | Wright et al. |
| 2014/0093885 A1 | 4/2014 | Hua et al. |
| 2014/0094404 A1 | 4/2014 | Villaverde Corrales et al. |
| 2014/0099670 A1 | 4/2014 | Kostenuik et al. |
| 2014/0099671 A1 | 4/2014 | Wu et al. |
| 2014/0112951 A1 | 4/2014 | Tang et al. |
| 2014/0113376 A1 | 4/2014 | Sorek et al. |
| 2014/0127216 A1 | 5/2014 | Balraj et al. |
| 2014/0134171 A1 | 5/2014 | Ghayur et al. |
| 2014/0148582 A1 | 5/2014 | Gallo et al. |
| 2014/0154250 A1 | 6/2014 | Thompson et al. |
| 2014/0154252 A1 | 6/2014 | Thompson et al. |
| 2014/0154256 A1 | 6/2014 | Wu et al. |
| 2014/0155343 A1 | 6/2014 | Brahmbhatt et al. |
| 2014/0155581 A1 | 6/2014 | Gao et al. |
| 2014/0161767 A1 | 6/2014 | Leuschner et al. |
| 2014/0161800 A1 | 6/2014 | Blankenship et al. |
| 2014/0178341 A1 | 6/2014 | Zhao et al. |
| 2014/0186377 A1 | 7/2014 | Gu et al. |
| 2014/0186401 A1 | 7/2014 | Diamond et al. |
| 2014/0187491 A1 | 7/2014 | Wilmen et al. |
| 2014/0189896 A1 | 7/2014 | Zhang et al. |
| 2014/0199306 A1 | 7/2014 | Ghosh et al. |
| 2014/0205538 A1 | 7/2014 | Wei et al. |
| 2014/0206064 A1 | 7/2014 | Bayer et al. |
| 2014/0206599 A1 | 7/2014 | Baumann et al. |
| 2014/0212396 A1 | 7/2014 | Newman |
| 2014/0212925 A1 | 7/2014 | Wu et al. |
| 2014/0219912 A1 | 8/2014 | Ghayur et al. |
| 2014/0220019 A1 | 8/2014 | Ghayur et al. |
| 2014/0220661 A1 | 8/2014 | Bermudes |
| 2014/0227291 A1 | 8/2014 | Barghorn et al. |
| 2014/0227294 A1 | 8/2014 | Anderson et al. |
| 2014/0234208 A1 | 8/2014 | Ghayur et al. |
| 2014/0255345 A1 | 9/2014 | Grabstein et al. |
| 2014/0256922 A1 | 9/2014 | David et al. |
| 2014/0271640 A1 | 9/2014 | Bowdish et al. |
| 2014/0298499 A1 | 10/2014 | Gray et al. |
| 2014/0308286 A1 | 10/2014 | Ghayur et al. |
| 2014/0328794 A1 | 11/2014 | Rosen et al. |
| 2014/0328849 A1 | 11/2014 | Reif et al. |
| 2014/0328875 A1 | 11/2014 | Garcia-Sastre et al. |
| 2014/0335014 A1 | 11/2014 | Ghayur et al. |
| 2014/0335087 A1 | 11/2014 | Buechler et al. |
| 2014/0335564 A1 | 11/2014 | Hsieh et al. |
| 2014/0341943 A1 | 11/2014 | Rikihisa |
| 2014/0342405 A1 | 11/2014 | Rosen et al. |
| 2014/0342451 A1 | 11/2014 | Kwon et al. |
| 2014/0343267 A1 | 11/2014 | Hsieh et al. |
| 2014/0348817 A1 | 11/2014 | Jiang et al. |
| 2014/0369986 A1 | 12/2014 | Padmanabhan et al. |
| 2014/0371194 A1 | 12/2014 | Seed et al. |
| 2014/0377858 A1 | 12/2014 | Wu et al. |
| 2014/0377860 A1 | 12/2014 | Wu et al. |
| 2014/0378372 A1 | 12/2014 | Mogelsvang et al. |
| 2015/0010592 A1 | 1/2015 | Wacker et al. |
| 2015/0017095 A1 | 1/2015 | Ghayur et al. |
| 2015/0018522 A1 | 1/2015 | Qasba et al. |
| 2015/0030584 A1 | 1/2015 | Rummel |
| 2015/0031658 A1 | 1/2015 | Seed et al. |
| 2015/0044722 A1 | 2/2015 | Tremblay et al. |
| 2015/0050215 A1 | 2/2015 | Novak et al. |
| 2015/0079063 A1 | 3/2015 | Fima et al. |
| 2015/0093358 A1 | 4/2015 | Fares et al. |
| 2015/0093387 A1 | 4/2015 | Wu et al. |
| 2015/0098900 A1 | 4/2015 | Ebens et al. |
| 2015/0099707 A1 | 4/2015 | Pastan et al. |
| 2015/0104452 A1 | 4/2015 | Ghayur et al. |
| 2015/0104514 A1 | 4/2015 | Kaplan et al. |
| 2015/0110720 A1 | 4/2015 | Markiv et al. |
| 2015/0110836 A1 | 4/2015 | Glanville |
| 2015/0119354 A1 | 4/2015 | Kahne et al. |
| 2015/0126445 A1 | 5/2015 | Fares et al. |
| 2015/0132218 A1 | 5/2015 | Asundi et al. |
| 2015/0132330 A1 | 5/2015 | Garcia-Sastre et al. |
| 2015/0132368 A1 | 5/2015 | Muro Galindo et al. |
| 2015/0133375 A1 | 5/2015 | Mogelsvang et al. |
| 2015/0141331 A1 | 5/2015 | Fares et al. |
| 2015/0141622 A1 | 5/2015 | Alitalo et al. |
| 2015/0147343 A1 | 5/2015 | Nitsch et al. |
| 2015/0148291 A1 | 5/2015 | Fima et al. |
| 2015/0150959 A1 | 6/2015 | Watnick |
| 2015/0152161 A1 | 6/2015 | Reiter et al. |
| 2015/0166594 A1 | 6/2015 | Kahne et al. |
| 2015/0166661 A1 | 6/2015 | Chen et al. |
| 2015/0166975 A1 | 6/2015 | Prakash et al. |
| 2015/0183867 A1 | 7/2015 | Ghayur et al. |
| 2015/0191691 A1 | 7/2015 | Bisanz et al. |
| 2015/0202284 A1 | 7/2015 | Dimitrov |
| 2015/0203578 A1 | 7/2015 | Bebbington et al. |
| 2015/0218231 A1 | 8/2015 | Bakaletz et al. |

(56) References Cited

U.S. PATENT DOCUMENTS

| | | |
|---|---|---|
| 2015/0218254 A1 | 8/2015 | Sabbadini et al. |
| 2015/0218261 A1 | 8/2015 | Barghorn et al. |
| 2015/0218544 A9 | 8/2015 | Jiang et al. |
| 2015/0232550 A1 | 8/2015 | Ghayur et al. |
| 2015/0232557 A1 | 8/2015 | Tan et al. |
| 2015/0232861 A1 | 8/2015 | Delisa et al. |
| 2015/0240226 A1 | 8/2015 | Mathur et al. |
| 2015/0247172 A1 | 9/2015 | Herrema |
| 2015/0252097 A1 | 9/2015 | Camphausen et al. |
| 2015/0258209 A1 | 9/2015 | Benz et al. |
| 2015/0259418 A1 | 9/2015 | Barth et al. |
| 2015/0266939 A1 | 9/2015 | Vogan et al. |
| 2015/0266977 A1 | 9/2015 | Hsieh et al. |
| 2015/0273045 A1 | 10/2015 | Kolander et al. |
| 2015/0273048 A1 | 10/2015 | Kang et al. |
| 2015/0275241 A1 | 10/2015 | Herrema |
| 2015/0284467 A1 | 10/2015 | Lipp et al. |
| 2015/0307576 A1 | 10/2015 | Bowdish et al. |
| 2015/0315283 A1 | 11/2015 | Ghayur et al. |
| 2015/0329619 A1 | 11/2015 | Rosen et al. |
| 2015/0329644 A1 | 11/2015 | Shi et al. |
| 2015/0335729 A1 | 11/2015 | Garcia-Sastre et al. |
| 2015/0337053 A1 | 11/2015 | McCarthy et al. |
| 2015/0344862 A1 | 12/2015 | Schellenberger et al. |
| 2015/0344894 A1 | 12/2015 | Giacalone et al. |
| 2015/0353911 A1 | 12/2015 | Salas et al. |
| 2015/0368630 A9 | 12/2015 | Fima et al. |
| 2016/0222393 A1 | 8/2016 | Bermudes |

FOREIGN PATENT DOCUMENTS

| | | |
|---|---|---|
| WO | WO2002070645 | 9/2002 |
| WO | WO2002074336 | 9/2002 |
| WO | WO2002083214 | 10/2002 |
| WO | WO2002087494 | 11/2002 |
| WO | WO2003014380 | 2/2003 |
| WO | WO2004016281 | 2/2004 |
| WO | WO2005018332 | 3/2005 |
| WO | WO2005054477 | 6/2005 |
| WO | WO2006017929 | 2/2006 |
| WO | WO2006048344 | 5/2006 |
| WO | WO2008073148 | 6/2008 |
| WO | WO2008089132 | 7/2008 |
| WO | WO2009021548 | 2/2009 |
| WO | WO2009111177 | 9/2009 |
| WO | WO2009126189 | 10/2009 |
| WO | WO2010027423 | 3/2010 |
| WO | WO2012072806 | 6/2012 |
| WO | WO2013022091 | 2/2013 |

Bacterial population 0.7 -1.5 x 2.0 -5.0 µm

MODIFIED BACTERIA HAVING IMPROVED
PHARMACOKINETICS AND TUMOR
COLONIZATION ENHANCING ANTITUMOR
ACTIVITY

CROSS REFERENCE TO RELATED
APPLICATIONS

The present application is a Divisional of U.S. patent application Ser. No. 15/679,874, filed Aug. 17, 2017, which is a continuation of Ser. No. 15/482,170, filed Apr. 7, 2017, now pending, which is a Divisional of U.S. patent application Ser. No. 14/858,810, filed Sep. 18, 2015, now U.S. Pat. No. 9,616,114, issued Apr. 11, 2017, which is a non-provisional of, and claims benefit of priority under 35 U.S.C. § 119(e) from, U.S. Provisional Patent Application No. 62/052,252, filed Sep. 18, 2014, the entirety of which is expressly incorporated herein by reference.

1. FIELD OF THE INVENTION

This invention is generally in the field of therapeutic delivery systems utilizing live bacteria for the diagnosis and treatment of neoplastic disease.

2. BACKGROUND OF THE INVENTION

Citation or identification of any reference herein, or any section of this application shall not be construed as an admission that such reference is available as prior art to the present application. The disclosures of each of these publications and patents are hereby incorporated by reference in their entirety in this application, and shall be treated as if the entirety thereof forms a part of this application. Such references are provided for their disclosure of technologies to enable practice of the present invention, to provide basis for claim language, to make clear applicant's possession of the invention with respect to the various aggregates, combinations, and subcombinations of the respective disclosures or portions thereof (within a particular reference or across multiple references). The citation of references is intended to be part of the disclosure of the invention, and not merely supplementary background information. The incorporation by reference does not extend to teachings which are inconsistent with the invention as expressly described herein, and is evidence of a proper interpretation by persons of ordinary skill in the art of the terms, phrase and concepts discussed herein, without being limiting as the sole interpretation available.

Cancer or neoplastic diseases including solid tumors, lymphomas, leukemias or leukemic bone marrow, is a devastating condition of uncontrolled cell growth, which often has the ability to spread throughout the body (metastases) resulting in death. Tumor-targeted bacteria offer tremendous potential advantages for the treatment of solid tumors, including the targeting from a distant inoculation site and the ability to express therapeutic agents directly within the tumor (Pawelek et al., 1997, Tumor-targeted *Salmonella* as a novel anticancer agent, Cancer Research 57: 4537-4544; Low et al., 1999, Lipid A mutant *Salmonella* with suppressed virulence and TNF-alpha induction retain tumor-targeting in vivo, Nature Biotechnol. 17: 37-41), each of which is expressly incorporated herein by reference in its entirety.

The primary shortcoming of tumor-targeted bacteria investigated in the human clinical trials (*Salmonella* strain VNP20009 and its derivative TAPET-CD; Toso et al., 2002, Phase I study of the intravenous administration of attenuated *Salmonella typhimurium* to patients with metastatic melanoma, J. Clin, Oncol. 20: 142-152; Meir et al., 2001, Phase 1 trial of a live, attenuated *Salmonella typhimurium* (VNP20009) administered by direct Intra-tumoral (IT) injection, Proc Am Soc Clin Oncol 20: abstr 1043); Nemunaitis et al., 2003, Pilot trial of genetically modified, attenuated *Salmonella* expressing the *E. coli* cytosine deaminase gene in refractory cancer patients, Cancer Gene Therapy 10: 737-744, each of which is expressly incorporated herein by reference in its entirety) was that no significant antitumor activity was observed, even in patients where the bacteria was documented to target the tumor. In addition, an important factor was also that bacterial colonization of tumors, both in the form of the percentage of tumors that were colonized and amount of the bacteria that accumulated within the tumors, was usually lower compared to the preclinical studies using mice. One method of increasing the ability of the bacteria to expand their numbers within tumors is to kill tumor cells by engineering the bacteria to express conventional bacterial toxins (e.g., WO2009/126189, WO03/014380, WO/2005/018332, WO/2008/073148, US 2003/0059400 U.S. Pat. Nos. 7,452,531, 7,354,592, 6,962, 696, 6,923,972, 6,863,894, 6,685,935, 6,475,482, 6,447,784, 6,190,657 and 6,080,849, each of which is expressly incorporated herein by reference in its entirety).

Use of secreted proteins in live bacterial vectors has been demonstrated by several authors. Holland et al. (U.S. Pat. No. 5,143,830, expressly incorporated in its entirety herein by reference in its entirety) have illustrated the use of fusions with the C-terminal portion of the hemolysin A (hlyA) gene, a member of the type I secretion system. When co-expressed in the presence of the hemolysin protein secretion channel (hlyBD) and a functional TolC, heterologous fusions are readily secreted from the bacteria. The type I secretion system that has been utilized most widely, and although it is currently considered the best system available, is thought to have limitations for delivery by attenuated bacteria (Hahn and Specht, 2003, FEMS Immunology and Medical Microbiology, 37: 87-98, expressly incorporated herein by reference in its entirety). Those limitations include the amount of protein secreted and the ability of the protein fused to it to interfere with secretion. Improvements of the type I secretion system have been demonstrated by Sugamata and Shiba (2005 Applied and Environmental Microbiology 71: 656-662), expressly incorporated herein by reference in its entirety, using a modified hlyB, and by Gupta and Lee (2008 Biotechnology and Bioengineering, 101: 967-974), expressly incorporated herein by reference in its entirety, by addition of rare codons to the hlyA gene, each of which is expressly incorporated by reference in their entirety herein. Fusion to the gene ClyA (Galen et al., 2004, Infection and Immunity, 72: 7096-7106 and Type III secretion proteins have also been used. Surface display has been used to export proteins outside of the bacteria. For example, fusion of the Lpp protein amino acids 1-9 with the transmembrane region B3-B7 of OmpA has been used for surface display (Samuelson et al., 2002, Display of proteins on bacteria, J. Biotechnology 96: 129-154, expressly incorporated by reference in its entirety). The autotransporter surface display has been described by Berthet et al., WO/2002/070645, expressly incorporated by reference in its entirety. Other heterologous protein secretion systems utilizing the autotransporter family can be modulated to result in either surface display or complete release into the medium (see Henderson et al., 2004, Type V secretion pathway: the autotransporter story, Microbiology and Molecular Biology Reviews 68: 692-744; Jose, 2006 Applied Microbiol. Biotechnol. 69: 607-614; Jose J, Zangen D (2005) Autodisplay of the protease inhibitor aprotinin in *Escherichia coli*. Biochem Biophys Res Commun 333:1218-1226 and Rutherford and Mourez 2006 Microbial Cell Factories 5: 22). For example, Veiga et al. (2003 Journal of Bacteriology 185: 5585-5590 and Klauser et al., 1990 EMBO Journal 9: 1991-1999), each of which is expressly incorporated herein by reference in its entirety, demonstrated hybrid proteins containing the b-autotransporter domain of the immunoglobulin A (IgA) protease of *Nisseria gonorrhea*. Fusions to flagellar proteins have been demonstrated. The peptide, usually of 15 to 36 amino acids in length, is inserted into the central, hypervariable region of the FliC gene such as that from *Salmonella muenchen* (Verma et al. 1995 Vaccine 13: 235-24; Wu et al., 1989 Proc. Natl. Acad. Sci. USA 86: 4726-4730; Cuadro et al., 2004 Infect. Immun. 72: 2810-2816; Newton et al., 1995, Res. Microbiol. 146: 203-216, each of which is expressly incorporated by reference in its entirety). Multihybrid FliC insertions of up to 302 amino acids have also been prepared (Tanskanen et al. 2000, Appl. Env. Microbiol. 66: 4152-4156, each of which is expressly incorporated by reference in its entirety). Trimerization of antigens and functional proteins can be achieved using the T4 fibritin foldon trimerization sequence (Wei et al. 2008 J. Virology 82: 6200-6208) and VASP tetramerization domains (Kühnel et al., 2004 PNAS 101: 17027-17032), each of which is expressly incorporated by reference in its entirety. The multimerization domains are used to create, bi-specific, tri-specific, and quatra-specific targeting agents, whereby each individual agent is expressed with a multimerization tag, each of which may have the same or separate targeting peptide, such that following expression, surface display, secretion and/or release, they form multimers with multiple targeting domains. Other secretion systems include C-terminal fusions to the protein YebF (Zhang et al., 2006, Extracellular accumulation of recombinant proteins fused to the carrier protein YebF in *Escherichia coli*, Nat Biotechnol 24: 100-104, expressly incorporated herein by reference in its entirety), which is commercially available as a kit (pAES40; AthenaES, Baltimore, Md.). Fusions to OmsY and other proteins are also capable of secreting proteins into the medium (Zian et al., 2008, Proteome-Based Identification of Fusion Partner for High-Level Extracellular Production of Recombinant Proteins in *Escherichia coli*, Biotechnol Bioegineer 101: 587-601), expressly incorporated herein by reference in its entirety. Other secretions systems usable according to the present invention include that of Kotzsch et al. 2011 (A secretory system for bacterial production of high-profile protein targets, Protein Science 20: 597-609) using OmpA, OmpF and OsmY, or those described by Yoon et al., 2010 (Secretory production of recombinant proteins in *Escherichia coli*, Recent Patents on Biotechnology 4: 23-29; US20067094579B2, WO2009021548A1, EP1402036B1, US20067070989B2, US20080193974A1, US200670528-67B2, US20036605697B1, U.S. Pat. No. 5,470,719A, US20070287171A1, US20090011995A1, US200800761-57A1, US20067112434B2, US20056919198B1, US026455279B1, US20077291325B2, US20087410788B2, US006083715A, EP1270730A1, US20046673569B1, US016309861B1, U.S. Pat. No. 5,989,868A, US20067056732B2, US20056852512B2, US2005686140-3B2, EP1407052B1, WO2008089132A2, U.S. Pat. No. 5,824,502A, EP1068339B1, US20080166757A1, US016329172B1, US036596509B1, US20036642027B2, WO2006017929A1, US20036596510B1, US2008028034-6A1, US20077202059B2, US20080280346A1, US2007-7202059B2, US20097491528B2, US20080206814A1, US20080166764A1, US20080182295A1, US20080254511-A1, US20080206818A1, US20067105327B1, US2004-0005695A1, U.S. Pat. No. 5,508,192A, EP866132A2, U.S. Pat. No. 6,921,659B2, U.S. Pat. No. 6,828,121B2, US20080064062A1, EP786009B1, US20060270043A1), and Habermann and Ertl (U.S. Pat. No. 7,202,059 Fusion proteins capable of being secreted into a fermentation medium), which uses fusions to hirudin, each of which is expressly incorporated herein by reference in its entirety.

Compositions described in accordance with various embodiments herein include, without limitation, *Salmonella enterica* serovar *typhimurium* ("*S. typhimurium*"), *Salmonella montevideo*, *Salmonella enterica* serovar *typhi* ("*S. typhi*"), *Salmonella enterica* serovar *paratyphi* A, *paratyphi* B ("*S. paratyphi* 13"), *Salmonella enterica* serovar *paratyphi* C ("*S. paratyphi* C"), *Salmonella enterica* serovar *hadar* ("*S. hadar*"), *Salmonella enterica* serovar *Enteriditis* ("*S. enteriditis*"), *Salmonella enterica* serovar *kentucky* ("*S. kentucky*"), *Salmonella enterica* serovar *infantis* ("*S. infantis*"), *Salmonella enterica* serovar *pullorum* ("*S. pullorum*"), *Salmonella enterica* serovar *gallinarum* ("*S. gallinarum*"), *Salmonella enterica* serovar *muenchen* ("*S. muenchen*"), *Salmonella enterica* serovar *anaturn* ("*S. anatum*"), *Salmonella enterica* serovar *dublin* ("*S. dublin*"), *Salmonella enterica* serovar *derby* ("*S. derby*"), *Salmonella enterica* serovar *choleraesuis* var. *kunzendorf* ("*S. cholerae* kunzendorf"), and *Salmonella enterica* serovar *minnesota* (*S. minnesota*). A preferred serotype for the treatment of bone marrow related diseases is *S. dublin*.

By way of example, live bacteria in accordance with aspects of the invention include known strains of *S. enterica* serovar *typhimurium* (*S. typhimurium*) and *S. enterica* serovar *typhi* (*S. typhi*) which are further modified as provided by various embodiments of the invention. Such Strains include Ty21a, CMV906, CMV908, CMV906-htr, CMV908-htr, Ty800, aroA-/serC-, holavax, M01ZH09, VNP20009. See also, U.S. Pat. No. 6,548,287, and EP 0,973,911, each of which is expressly incorporated herein by reference in its entirety. See also, US 20140256922; 20120108640; 20110318308; 20090215754; 20090169517; 20070298012; 20070110752; 20070004666; 20060115483; 20060104955; 20060089350; 20060025387; 20050267103; 20050249706; 20050112642; 20050009750; 20040229338; 20040219169; 20040058849; 20030143676; 20030113293; 20030031628; 20030022835; 20020151063; 20140220661; 20140212396; 20140186401; 20140178341; 20140155343; 20140093885; 20130330824; 20130295054; 20130209405; 20130130292; 20120164687; 20120142080; 20120128594; 20120093773; 20120020883; 20110275585; 20110111496; 20110111481; 20100239546; 20100189691; 20100136048; 20100135973; 20100135961; 20100092438; 20090300779; 20090180955; 20090175829; 20090123426; 20090053186; 20080311081; 20080124355; 20080038296; 20070110721; 20070104689; 20060083716; 20050026866; 20050008618; 20040202663; 20050255088; 20030109026; 20020026655; 20110223241; 20070009489; 20050036987; 20030170276; 20140148582; 20130345114; 20130287810; 20130164380; 20130164307; 20130078275; 20120225454; 20120177682; 20120148601; 20120144509; 20120083587; 20120021517; 20110274719; 20110268661; 20110165680; 20110091493; 20110027349; 20100172976; 20090317404; 20090220540; 20090123382; 20090117049; 20090117048; 20090117047; 20090068226; 20080249013; 20080206284; 20070202591;

20070191262; 20070134264; 20060127408; 20060057152; 20050118193; 20050069491; 20050064526; 20040234455; 20040202648; 20040054142; 20030170211; 20030059400; 20030036644; 20030009015; 20030008839; 20020176848; 20020102242; 20140205538; 20140112951; 20140086950; 20120244621; 20120189572; 20110104196; 20100233195; 20090208534; 20090136542; 20090028890; 20080260769; 20080187520; 20070031382; 20060140975; 20050214318; 20050214317; 20050112140; 20050112139; 20040266003; 20040115174; 20040009936; 20030153527; 20030125278; 20030045492; U.S. Pat. Nos. 8,828,681; 8,822,194; 8,784,836; 8,771,669; 8,734,779; 8,722,668; 8,715,641; 8,703,153; 8,685,939; 8,663,634; 8,647,642; 8,642,257; 8,623,350; 8,604,178; 8,591,862; 8,586,022; 8,568,707; 8,551,471; 8,524,220; 8,440,207; 8,357,486; 8,343,509; 8,323,959; 8,282,919; 8,241,623; 8,221,769; 8,198,430; 8,137,904; 8,066,987; 8,021,662; 8,008,283; 7,998,461; 7,955,600; 7,939,319; 7,915,218; 7,887,816; 7,842,290; 7,820,184; 7,803,531; 7,790,177; 7,786,288; 7,763,420; 7,754,221; 7,740,835; 7,736,898; 7,718,180; 7,700,104; 7,691,383; 7,687,474; 7,662,398; 7,611,883; 7,611,712; 7,588,771; 7,588,767; 7,514,089; 7,470,667; 7,452,531; 7,404,963; 7,393,525; 7,354,592; 7,344,710; 7,247,296; 7,195,757; 7,125,718; 7,084,105; 7,083,791; 7,015,027; 6,962,696; 6,923,972; 6,916,918; 6,863,894; 6,770,632; 6,685,935; 6,682,729; 6,506,550; 6,500,419; 6,475,482; 6,447,784; 6,207,648; 6,190,657; 6,150,170; 6,080,849; 6,030,624; and 5,877,159, each of which is expressly incorporated herein by reference in its entirety.

Novel strains are also encompassed that are, for example, attenuated in virulence by mutations in a variety of metabolic and structural genes. The invention therefore may provide a live composition for treating cancer comprising a live attenuated bacterium that is a serovar of *Salmonella enterica* comprising an attenuating mutation in a genetic locus of the chromosome of said bacterium that attenuates virulence of said bacterium and wherein said attenuating mutation is the Suwwan deletion (Murray et al., 2004. Hot spot for a large deletion in the 18-19 Cs region confers a multiple phenotype in *Salmonella enterica* serovar *typhimurium* strain ATCC 14028. Journal of Bacteriology 186: 8516-8523 (2004), expressly incorporated herein by reference in its entirety) or combinations with other known attenuating mutations. Other attenuating mutation useful in the *Salmonella* bacterial strains described herein may be in a genetic locus selected from the group consisting of phoP, phoQ, edt, cya, crp, poxA, rpoS, htrA, nuoG, pmi, pabA, pts, damA, pur, purA, purB, purI, purF, zwf, aroA, aroB, aroC, aroD, serC, gua, cadA, rfc, rjb, rfa, ompR, msbB, leucine and arginine, and combinations thereof. Strains of *Salmonella* deleted in stn are particularly preferred.

The invention also encompasses attenuated gram-positive bacteria. For example, *Staphylococcus epidermidis*, group B *Streptococcus* including *S. agalaciae*, and *Listeria* species including *L. monocytogenes* may be employed. It is known to those skilled in the art that variations in molecular biology techniques such as use of gram-positive origins of replication, gram-positive signal sequences and gram-positive promoters and filamentous phage (e.g., phage B5; Chopin et al., 2002 J. Bacteriol. 184: 2030-2033, expressly incorporated herein by reference in its entirety, described further below) may be employed and substituted as needed. Other bacterial strains may also be encompassed, including non-pathogenic bacteria of the gut skin (such as *Staphylococcus epidermidis*, Proprionibacteria) and other body locations known as the human microbiome (Grice et al., Topographical and temporal diversity of the human skin microbiome, Science 324: 1190-1192; A framework for human microbiome research; The Human Microbiome Project Consortium, 14 Jun. 2012 Nature 486, 215-221; Spor et al., 2011, Unravelling the effects of the environment and host genotype on the gut microbiome, Nature Reviews Microbiology 9: 279-290, each of which is expressly incorporated herein by reference in its entirety) such as *E. coli* strains, Bacteriodies, *Bifidobacterium* and *Bacillus*, attenuated pathogenic strains of *E. coli* including enteropathogenic and uropathogenic isolates, *Enterococcus* sp. and *Serratia* sp. as well as attenuated *Neisseria* sp., *Shigella* sp., *Staphylococcus* sp., *Staphylococcus carnosis*, *Yersinia* sp., *Streptococcus* sp. and *Listeria* sp. including *L. monocytogenes*. Bacteria of low pathogenic potential to humans and other mammals or birds or wild animals, pets and livestock, such as insect pathogenic *Xenorhabdus* sp., *Photorhabdus* sp. and human wound *Photorhabdus* (*Xenorhabdus*) are also encompassed. Probiotic strains of bacteria are also encompassed, including *Lactobacillus* sp. (e.g., *Lactobacillus acidophilus*, *Lactobacillus salivarius*) *Lactococcus* sp., (e.g., *Lactococcus lactis*, *Lactococcus casei*) *Leuconostoc* sp., *Pediococcus* sp., *Streptococcus* sp. (e.g., *S. salivariu*, *S. thermophilus*), *Bacillus* sp., *Bifidobacterium* sp., *Bacteroides* sp., and *Escherichia coli* such as the 1917 Nissel strain. It is known to those skilled in the art that minor variations in molecular biology techniques such as use of gram-positive origins of replication, gram-positive signal sequences gram-positive promoters (e.g., *Lactococcus* expression, Mohamadzadeh et al., PNAS Mar. 17, 2009 vol. 106 no. 114331-4336, expressly incorporated herein by reference in its entirety) may be used and substituted as needed. The bacteria may be further modified to be internalized into the host cell (Guimaraes et al., 2006, Use of Native Lactococci as Vehicles for Delivery of DNA into Mammalian Epithelial Cells, Appl Environ Microbiol. 2006 November; 72(11): 7091-7097; Innocentin et al., 2009, *Lactococcus lactis* Expressing either *Staphylococcus aureus* Fibronectin-Binding Protein A or *Listeria monocytogenes* Internalin A Can Efficiently Internalize and Deliver DNA in Human Epithelial Cells Appl Environ Microbiol. 2009 July; 75(14): 4870-4878, each of which is expressly incorporated herein by reference in its entirety).

The invention also encompasses combinations with known agents, including imatinib and reticuloendothelial system (RES) blocker such as clodronate (dichloromethylene-bisphosphonate; Compositions and methods comprising genetically enhanced obligate and facultative anaerobic bacteria for oncopathic cancer therapy, WO 2009111177, expressly incorporated herein by reference in its entirety) which have the potential to improve the circulation time of the bacteria, vascular permeability inducing agents such as bradykinin, hyperthermia or carbogen which have the potential to improve the permeability of the tumor enhancing entry of the bacteria, or aldose reductase inhibitors.

The invention also encompasses combinations with protease inhibitors and targeted toxins and chimeric toxins and antitumor enzymes and/or genetically engineered phage and phagemids (Bermudes U.S. Pat. No. 8,524,220, Protease Inhibitor: Protease sensitivity expression system composition and methods improving the therapeutic activity and specificity of proteins delivered by bacteria; U.S. Pat. No. 8,241,623, Protease Sensitivity Expression System; U.S. Pat. No. 8,623,350 Protease inhibitor protease sensitivity expression system and method improving the therapeutic activity and specificity of proteins and phage and phagemids delivered by bacteria, each of which is expressly incorporated herein by reference in its entirety).

The invention also encompasses combinations with antivascular agents, such as platelet factor 4 and thrombospondin, alone or in combination (Bermudes et al., U.S. Pat. Nos. 6,962,696, 7,452,531 Compositions and Methods for Tumor-Targeted Delivery of Effector Molecules, each of which is expressly incorporated herein by reference in its entirety).

The present invention provides, according to various embodiments, live attenuated therapeutic bacterial strains that have improved ability compared to a parental strain in regard to the pharmacokinetic properties of enhanced circulation in the bloodstream and entry into, persistence and growth within tumors, by resisting immune elimination or lytic destruction, increased numbers of foci within tumors, increased colonization, expansion and persistence within tumors. It is the intention of these changes that the result in an overall increase in 1) the percentage of tumors targeted, 2) the number of individual locations (foci) within a tumor that are targeted, 3) the number of CFU/g that are found within the tumor, 4) the length of time that they reside within the tumor and 5) reduced immune clearance from the tumor, and, alone or collectively 6) increased antitumor activity.

3. SUMMARY AND OBJECTS OF THE INVENTION

3.1 Improved Pharmacokinetics and Tumor Colonization

The present technology provides compositions and methods to enhance bacterial half-life in the bloodstream, passage out of the vasculature into the target tissue, targeting of tumors and lymphomas, colonization of tumors and lymphomas, expansion within tumor or lymphoma and persistence within tumor and lymphomas, each of which, alone or in combination or subcombination, result in an overall increase in 1) the percentage of tumors and lymphomas targeted, 2) the number of individual locations (foci) within a tumor or lymphoma that are established, 3) the number of colony forming units (CFU/g) that are found within the tumor or lymphoma, 4) the length of time that they reside within the tumor or lymphoma and 5) reduced immune clearance from the tumor or lymphoma, and, alone or collectively, 6) increased anticancer activity.

The compositions or genetically engineered bacteria may comprise at least one of 1) one or more mutations that result in smaller sized bacteria (e.g., smaller volume, smaller surface area, small linear dimensions, or smaller mass) with improved (increased) half-life pharmacokinetics in blood and improved penetration though leaky tumor vasculature, 2) bacteria with a protective sialic acid coat that have improved (increased) pharmacokinetics in blood and improved penetration though leaky tumor vasculature and reduced immune clearance, 3) bacteria that alternately express external antigens such as O and H antigens under exogenous control of inducible promoters such that different antigens are expressed at different times and result in bacteria with improved (increased) pharmacokinetics in blood and reduced immune clearance and reduced immune recognition upon repeated dosing, 4) bacteria that deliver ligands against programmed cell death protein 1 ligand (PD-L1) which sequester or block those ligands and result in T-cells attacking tumors and increasing the habitable region of the tumor by bacteria, 5) expression of the *E. coli* tryptophanase which results in greater tumor cell killing and enhanced penetration of the bacteria within the tumor, and 6) expression of mammalian or bacterial tyrosinase at high (toxic) levels, which e.g., can lead to oxidative stress and metabolic disruption, or prodrug activation.

7) bacteria with resistance to human serum and serum components, which acts as an alternative mechanism to reduced elimination by selection for spontaneously resistant mutants alone or together with $CO_2$ resistance, or expression of serum resistance proteins.

The types of cancers or neoplasias to which the present invention is directed include all neoplastic malignancies, including solid tumors such as those of colon, lung, breast, prostate, sarcomas, carcinomas, head and neck tumors, melanoma, as well as hematological, non-solid or diffuse cancers such as leukemia and lymphomas, myelodysplastic cells, plasma cell myeloma, plasmacytomas, and multiple myelomas. Specific types of cancers include acute lymphoblastic leukemia, acute myeloid leukemia, adrenocortical carcinoma adrenocortical carcinoma, aids-related cancers, aids-related lymphoma, anal cancer, appendix cancer, astrocytomas, childhood, teratoid/rhabdoid tumor, childhood, central nervous system tumors, basal cell carcinoma, bile duct cancer, extrahepatic bladder cancer, bladder cancer, bone cancer, osteosarcoma and malignant fibrous histiocytoma, brain glioma, brain tumor, brain stem glioma, central nervous system atypical teratoid/rhabdoid tumor, central nervous system embryonal tumors, brain tumor, astrocytomas, craniopharyngioma, ependymoblastoma, ependymoma, medulloblastoma, medulloepithelioma, pineal parenchymal tumors, supratentorial primitive neuroectodermal tumors and pineoblastoma, spinal cord tumors, breast cancer (female), breast cancer (male), bronchial tumors, burkitt lymphoma, carcinoid tumor, gastrointestinal, nervous system atypical teratoid/rhabdoid tumor, central nervous system embryonal tumors, central nervous system lymphoma, primary cervical cancer, cervical cancer, chordoma, chronic lymphocytic leukemia, chronic myelogenous leukemia, chronic myeloproliferative disorders, colon cancer, colorectal cancer, craniopharyngioma, cutaneous T-cell lymphoma, embryonal tumors, endometrial cancer, ependymoblastoma, ependymoma, esophageal cancer, ewing sarcoma family of tumors, extracranial germ cell tumor, extrahepatic bile duct cancer, eye cancer, intraocular melanoma, eye cancer, retinoblastoma gallbladder cancer, gastric (stomach) cancer, gastrointestinal carcinoid tumor, gastrointestinal stromal tumor (gist), gastrointestinal stromal cell tumor, germ cell tumor, extracranial germ cell tumor, extragonadal germ cell tumor, ovarian gestational trophoblastic tumor, glioma, hairy cell leukemia, head and neck cancer, hepatocellular (liver) cancer, primary hepatocellular (liver) cancer, histiocytosis, langerhans cell, hodgkin lymphoma, hypopharyngeal cancer, intraocular melanoma, islet cell tumors (endocrine pancreas), kaposi sarcoma, kidney (renal cell) cancer, kidney cancer, langerhans cell histiocytosis, laryngeal cancer, leukemia, acute lymphoblastic leukemia, acute myeloid leukemia, chronic lymphocytic leukemia, chronic myelogenous leukemia, hairy cell leukemia, lip and oral cavity cancer, liver cancer, adult (primary) liver cancer, (primary) lung cancer, non-small cell lung cancer, small cell lymphoma, aids-related lymphoma, burkitt lymphoma, cutaneous T-cell lymphoma, hodgkin lymphoma, non-hodgkin lymphoma, primary central nervous system lymphoma, macroglobulinemia, Waldenström malignant fibrous histiocytoma of bone and osteosarcoma, medulloblastoma, melanoma, intraocular (eye) melanoma, merkel cell carcinoma, mesothelioma, metastatic squamous neck cancer with occult primary, mouth cancer, multiple endocrine neoplasia syndrome, childhood multiple myeloma/ plasma cell neoplasm, mycosis fungoides, myelodysplastic syndromes, myelodysplastic/myeloproliferative diseases, myelogenous leukemia, chronic myeloid leukemia, adult acute myeloid leukemia, childhood acute myeloma, multiple myeloproliferative disorders, nasal cavity and paranasal sinus cancer, nasopharyngeal cancer, nasopharyngeal cancer, neuroblastoma, non-hodgkin lymphoma, non-small cell lung cancer, oral cancer, oral cavity cancer, lip and oropharyngeal cancer, osteosarcoma and malignant fibrous histiocytoma of bone, ovarian cancer, ovarian epithelial cancer, ovarian germ cell tumor, ovarian low malignant potential tumor, pancreatic cancer, islet cell tumors, papillomatosis, paranasal sinus and nasal cavity cancer, parathyroid cancer, penile cancer, pharyngeal cancer, pineal parenchymal tumors of intermediate differentiation, pineoblastoma and supratentorial primitive neuroectodermal tumors, pituitary tumor, plasma cell neoplasm/multiple myeloma, pleuropulmonary blastoma, primary central nervous system lymphoma, prostate cancer, rectal cancer, renal cell (kidney) cancer, renal pelvis and ureter, transitional cell cancer, respiratory tract carcinoma involving the nut gene on chromosome 15, retinoblastoma, rhabdomyosarcoma, salivary gland cancer, sarcoma, ewing sarcoma family of tumors, kaposi sarcoma, soft tissue sarcoma, uterine sarcoma, Sézary syndrome, skin cancer (nonmelanoma), melanoma, skin carcinoma, merkel cell, small cell lung cancer, small intestine cancer, soft tissue sarcoma, squamous cell carcinoma, see skin cancer (nonmelanoma), squamous neck cancer with occult primary, metastatic stomach (gastric) cancer, stomach (gastric) cancer, supratentorial primitive neuroectodermal tumors, T-cell lymphoma, cutaneous T-cell lymphoma, mycosis fungoides and Sézary syndrome, testicular cancer, throat cancer, thymoma and thymic carcinoma, thyroid cancer, transitional cell cancer of the renal pelvis and ureter, trophoblastic tumor, (gestational), unknown primary site, carcinoma of, unknown primary site carcinoma, ureter and renal pelvis, transitional cell cancer, urethral cancer, uterine cancer, endometrial uterine sarcoma, vaginal cancer, vulvar cancer, Waldenström macroglobulinemia, and Wilms tumor.

Issues related to bacterial targeting and efficacy have previously been address by Bermudes (Protease sensitivity expression system, U.S. Pat. No. 8,241,623 B1, incorporated by reference in its entirety in this application, and shall be treated as if the entirety thereof forms a part of this application). Survival under $CO_2$ conditions, high osmolarity and acidic conditions has also been addressed (Bermudes U.S. Pat. No. 8,647,642, (Live bacterial vaccines resistant to carbon dioxide ($CO_2$), acidic PH and/or osmolarity for viral infection prophylaxis or treatment), expressly incorporated by reference in its entirety.

As cited above, the primary shortcoming of tumor-targeted bacteria investigated in the human clinical trials (Salmonella strain VNP20009 and its derivative TAPET-CD; Toso et al., 2002, Phase I study of the intravenous administration of attenuated Salmonella typhimurium to patients with metastatic melanoma, J. Clin, Oncol. 20: 142-152; Meir et al., 2001, Phase 1 trial of a live, attenuated Salmonella typhimurium (VNP20009) administered by direct Intra-tumoral (IT) injection, Proc Am Soc Clin Oncol 20: abstr 1043; Nemunaitis et al., 2003, Pilot trial of genetically modified, attenuated Salmonella expressing the E. coli cytosine deaminase gene in refractory cancer patients, Cancer Gene Therapy 10: 737-744, each of which is expressly incorporated herein by reference in its entirety) is that no antitumor activity was observed, even in patients that were documented to have had tumors that were colonized by the bacteria. An additional divergence between the murine studies (e.g., Pawelek et al., 1997, Tumor-targeted Salmonella as a novel anticancer agent, Cancer Research 57: 4537-4544; Low et al., 1999, Lipid A mutant Salmonella with suppressed virulence and TNF-alpha induction retain tumor-targeting in vivo, Nature Biotechnol. 17: 37-41, each of which is expressly incorporated herein by reference in its entirety), is that in most patients, the levels of the bacteria were significantly lower. For example, whereas in the murine models the bacteria frequently achieved levels of $1\times10^9$ colony forming units (CFU) per gram of tumor tissue, in humans the levels were significantly lower, e.g., $1\times10^6$ CFU/g was achieved in 3 patients (Meir et al., 2001). Generally, it has been perceived that the murine studies should precede using bacteria with the greatest amount of tumor targeting. For example, Pawelek et al., WO/1996/040238, expressly incorporated herein by reference in its entirety, selected "super infective" bacteria by cycling through tumors. The novel cycling and selection procedure they employed selected for increased targeting numbers which was correlated with a greater antitumor effect. A similar study using the strain AR-1 was performed by Zhao et al., 2005 (Tumor-targeting bacterial therapy with amino acid auxotrophs of GFP-expressing Salmonella typhimurium) Proc Natl Acad Sci USA. 102: 755-760, expressly incorporated herein by reference in its entirety). In the development of the Salmonella strain A1-R by re-isolation form a tumor, as described by the same group in a later study (Hayashi et al., 2009, Cancer metastasis directly eradicated by targeted therapy with a modified Salmonella typhimurium, Journal of Cellular Biochemistry 106: 992-998, expressly incorporated herein by reference in its entirety) "The idea was to increase the tumor targeting capability of the bacteria." Thus, developing and testing bacteria with enhanced tumor targeting using known genetic backgrounds that already exhibit high levels of tumor targeting has been a focus within the field. However, while it is desirable to find ways to improve the levels of bacteria within tumors, including the present technology, the importance of selecting an appropriate tumor model and/or bacterial genetic background to assess the contribution that an effector system might have in a human, or how it might improve tumor colonization levels, wherein the tumor model and/or bacterial genetic background should provide low (rather than high) levels of tumor colonization, has not been appreciated. It has not been understood that to evaluate how an effector system such as the herpes simplex thymidine kinase or cytosine deaminase described by Pawelek et al., WO/1996/040238, expressly incorporated herein by reference in its entirety, or those provided in the present invention, would function in humans where lower targeting numbers might be expected (at least at the outset; greater number could be achieved if the effector system is effective), such that the murine tumor system and/or bacterial genetic background where the tumor-targeting level is similar to the level achieved in humans represents an appropriate model.

firA is a mutation within the gene that encodes the enzyme LJDP-3-O(R-30 hydroxymyristoyl)-glycocyamine N-acyltransferase, that regulates the third step in endotoxin biosynthesis (Kelley et al., 1993, J. Biol. Chem. 268:19866-19874, expressly incorporated herein by reference in its entirety). Salmonella typhimurium and E. coli strains bearing this type of mutation produce a lipid A that differs from wild type lipid A in that it contains a seventh fatty acid, a hexadecanoic acid (Roy and Coleman, 1994, J. Bacteriol. 176:1639-1646, expressly incorporated herein by reference in its entirety). Roy and Coleman demonstrated that in addition to blocking the third step in endotoxin biosynthesis, the firA mutation also decreases enzymatic activity of lipid A 4' kinase that regulates the sixth step of lipid A biosynthesis. *Salmonella typhimurium* strain SH5014 and its firA derivative SH7622 are described in Hirvas et al. 1991, EMBO J. 10:1017-1023, expressly incorporated herein by reference in its entirety. The genotypes of these strains are as follows: strain SH5014 ilv-1178 thr-914 rlis-6116 metA22 metE551 trpB2 xyl-404 HI-b H2-e, n, x flaA66 rpsL120 rfaJ4041; strain SH7622 ilv-1178 thr-914 his-6116 metA22 metE551 trpB2 xyl-404 Hl-b H2-e, n, x flahββ rpsL120 rfaJ4041, ssc-1 (firA$^{ts}$). A derivative of *Salmonella typhimurium* firA strain SH7622 was picked. designated SH7622-64, and used as the firA strain for the experiments. SH7622-64 was selected for its supersensitivity to the antibiotic novobiocin and temperature-sensitive growth, characteristics of the firA' SH7622 strain. When studies in two different tumor models, Pawelek et al. found *Salmonella*/g tissue: Primary Tumor of M27 lung cancer, 2.9×10 per gram and in B16 melanoma. 3.2×10$^5$ per gram, yet retaining a similar 3200: 1 tumor to liver targeting ratio. This strain, while never used in any subsequent studies, represents a surprising solution to translating murine to human studies wherein both systems tend to have the same number of bacteria per gram of target tissue.

In an alternative approach to selecting bacterial mutants using strain backgrounds with high tumor-targeting and antitumor effects as is commonly applied (Zhao et al., 2005, Tumor-targeting bacterial therapy with amino acid auxotrophs of GFP-expressing *Salmonella typhimurium*. Proc Natl Acad Sci USA. 102: 755-760, expressly incorporated herein by reference in its entirety), bacterial mutants with suboptimal targeting or low antitumor effects are used for selection of improved antitumor effects. The bacterial mutants can be generated by any standard method of mutation (e.g., UV, nitrosoguanadine, Tn10, Tn5), or can be a spontaneous mutation such as a suppressor mutation (e.g., Murray et al., 2001, Extragenic suppressors of growth defects in msbB *Salmonella*, J. Bacteriol. 183: 5554-5561, expressly incorporated herein by reference in its entirety), or those of the present invention.

Tyrosinase has been proposed as a cancer therapy, e.g., against melanoma. The action may be direct, or by action on a prodrug. See, Claus H, Decker H., Bacterial tyrosinases, Syst Appl Microbiol. 2006 January; 29(1):3-14. Epub 2005 Sep. 6; Maria Simonova, Alexander Wall, Ralph Weissleder, and Alexei Bogdanov, Jr., Tyrosinase Mutants Are Capable of Prodrug Activation in Transfected Nonmelanotic Cells, Cancer Research 60, 6656-6662, Dec. 1, 2000; Connors T. A. The choice of prodrugs for gene directed enzyme prodrug therapy of cancer. Gene Ther., 2: 702-709, 1995; Bridgewater J., Springer C., Knox R., Minton N., Michael N., Collins M. Expression of the bacterial nitroreductase enzyme in mammalian cells renders them selectively sensitive to killing by the prodrug CB1954. Eur. J. Cancer, 31A: 2362-2370, 1995; Austin E., Huber B. A first step in the development of gene therapy for colorectal carcinoma: cloning, sequencing, and expression of *Escherichia coli* cytosine. Mol. Pharmacol., 43: 380-387, 1993; Guzman R., Hirschowitz E., Brody S., Crystal R., Epstein S., Finkel T. In vivo suppression of injury-induced vascular smooth muscle cell accumulation using adenovirus-mediated transfer of the herpes simplex virus thymidine kinase gene. Proc. Natl. Acad. Sci. USA, 91: 10732-10736, 1994; Aghi M., Kramm C., Chou T., Breakefield X., Chiocca E. Synergistic anticancer effects of ganciclovir/thymidine kinase and 5-fluorocytosine/cytosine deaminase gene therapies. J. Natl. Cancer Inst., 90: 370-380, 1998; Jimbow K. Development of targeted chemoradiotherapy for malignant melanoma by exploitation of metabolic pathway. Hokkaido J. Med. Sci., 73: 105-110, 1998; Sterman D., Treat J., Litzky L., Amin K., Coonrod L., Molnar-Kimber K., Recio A., Knox L., Wilson J., Albelda S., Kaiser L. Adenovirus-mediated herpes simplex virus thymidine kinase/ganciclovir gene therapy in patients with localized malignancy: results of a Phase I clinical trial in malignant mesothelioma. Hum. Gene Ther., 9: 1083-1092, 1998; Bakina E., Wu Z., Rosenblum M., Farquhar D. Intensely cytotoxic anthracycline prodrugs: glucuronides. J. Med. Chem., 40: 4013-4018, 1997; Dewey D. L., Butcher F. W., Galpine A. R. Hydroxyanisole-induced regression of the Harding-Passey melanoma in mice. J. Pathol., 122: 117-127, 1977; Wick M. M., Byers L., Ratliff J. Selective toxicity of 6-hydroxydopa for melanoma cells. J. Investig. Dermatol., 72: 67-69, 1979; Jimbow M., Marusyk H., Jimbow K. The in vivo melanocytotoxicity and depigmenting potency of N-2,4-acetoxyphenyl thioethyl acetamide in the skin and hair. Br. J. Dermatol., 133: 526-536, 1995; Jimbow K. N-acetyl-4-S-cysteaminylphenol as a new type of depigmenting agent for the melanoderma of patients with melasma. Arch. Dermatol., 127:1528-1534, 1991; Singh M. V., Jimbow K. Tyrosinase transfection produces melanin synthesis and growth retardation in glioma cells. Melanoma Res., 8: 493-498, 1998; Toyofuku K., Wada I., Hirosaki K., Park J. S., Hori Y., Jimbow K. Promotion of tyrosinase folding in COS 7 cells by calnexin. J. Biochem. (Tokyo), 125: 82-89, 1999; Sanches-Ferrer A., Rodriguez-Lopez J., Garcia-Canovas F., Garcia-Carnoma F. Tyrosinase: a comprehensive review of its mechanism. Biochim. Biophys. Acta, 1247: 1-11, 1995; Luo D., Chen H., Jimbo K. Cotransfection of genes encoding human tyrosinase and tyrosinase-related protein-1 prevents melanocyte death and enhances melanin pigmentation and gene expression of Lamp-1. Exp. Cell Res., 213: 231-241, 1994; Eberle J., Garbe C., Wang N., Orfanos C. Incomplete expression of the tyrosinase gene family (tyrosinase, TRP-1, and TRP-2) in human malignant melanoma cells in vitro. Pigm. Cell. Res., 8: 307-313, 1995; Riley P. A., Cooksey C. J., Johnson C. I., Land E. J., Latter A. M., Ramsden C. A. Melanogenesis-targeted antimelanoma pro-drug development: effect of side-chain variations on the cytotoxicity of tyrosinase-generated ortho-quinones in a model screening system. Eur. J. Cancer, 33: 135-143, 1997; Bouchard B., Fuller B., Vijayasaraashi S., Houghton A. Induction of pigmentation in mouse fibroblasts by expression of human tyrosinase cDNA. J. Exp. Med., 169: 2029-2042, 1989; Kwon B. S. Pigmentation genes: the tyrosinase gene family and the pmel 17 gene family. J. Investig. Dermatol., 100(Suppl.): 134s-140s, 1993; Beermann F., Orlow S. J., Boissy R. E., Schmidt A., Boissy Y. L., Lamoreux M. L. Misrouting of tyrosinase with a truncated cytoplasmic tail as a result of the murine platinum (cp) mutation. Exp. Eye Res., 61: 599-607, 1995; Chen J., Cha Y., Yuksel K., Gracy R., August J. Isolation and sequencing of a cDNA clone encoding lysosomal membrane glycoprotein mouse LAMP-1. J. Biol. Chem., 263: 8754-8758, 1988; Williams R., Siegle R., Pierce B., Floyd L. Analogs of synthetic melanin polymers for specific imaging applications. Investig. Radiol., 29(Suppl.): 116s-119s, 1994; Kozak M. An analysis of 5'-noncoding sequences from 699 vertebrate messenger RNAs. Nucleic Acids Res., 15: 8125-8148, 1987; Halaban R., Cheng E., Zhang Y., Moellmann G., Hanlon D., Michalak M., Setaluri V., Hebert D. N. Aberrant retention of tyrosinase in the endoplasmic reticulum mediates accelerated degradation of the enzyme and contributes to the dedifferentiated phenotype of amelanotic melanoma cells. Proc. Natl. Acad. Sci. USA, 94: 6210-6215, 1997; Wheeler K., Tel N., Williams M., Sheppard S., Levin V., Kabra P. Factors influencing the survival of rat brain tumor cells after in vitro treatment with 1,3-bis (2-chloroethyl)-1-nitrosourea. Cancer Res., 35: 1464-1469, 1975; Pomerantz S. 1-tyrosine-3,5-3H assay for tyrosinase development in skin of newborn hamsters. Science (Washington D.C.), 164: 838-839, 1969; Mahalingam H., Vaughn J., Novothy J., Gruber J. R., Niles R. M. Regulation of melanogenesis in B16 mouse melanoma cells by protein kinase C. J. Cell. Physiol., 168: 549-558, 1996; Halaban R., Pomerantz S. H., Marshall S., Lambert D. T., Lerner A. B. Regulation of tyrosinase in human melanocytes grown in culture. J. Cell Biol., 97: 480-488, 1983; Enochs W. S., Petherick P., Bogdanova A., Mohr U., Weissleder R. Paramagnetic metal scavenging by melanin: MR imaging. Radiology, 204: 417-423, 1997; Chen Y-T., Stockert E., Tsang S., Coplan K. A., Old L. J. Immunotyping of melanomas for tyrosinase: implications for vaccine development. Proc. Natl. Acad. Sci. USA, 92: 8125-8129, 1995; Padgette S., Herman H., Han J., Pollock S., May S. Antihypertensive activities of phenylaminoethyl sulfides, a class of synthetic substrates for dopamine p-hydroxylase. J. Med. Chem., 27: 5826-5839, 1984; Prezioso J. A., Epperly M. W., Wang N., Bloomer W. D. Effects of tyrosinase activity on the cytotoxicity of 4-S-cysteaminylphenol and N-acetyl-4-S-cysteaminylphenol in melanoma cells. Cancer Lett., 63: 73-79, 1992; Morrison M. E., Yagi M. J., Cohen G. In vitro studies of 2,4-dihydroxyphenylalanine, a prodrug targeted against malignant melanoma cells. Proc. Natl. Acad. Sci. USA, 82: 2960-2964, 1985; Alena F., Jimbo K., I to S. Melanocytotoxicity and antimelanoma effects of phenolic amine compounds in mice in vivo. Cancer Res., 50: 3743-3747, 1990; Tandon M., Thomas P. D., Shokravi M., Ingh S., Samra S., Chang D., Jimbow K. Synthesis and antimelanoma effect of the melanogenesis-based antimelanoma agent N-propionyl-4-S-cysteaminylphenol. Biochem. Pharmacol., 55: 2023-2029, 1998; Naeyaert J., Eller M., Gordon P., Park H., Gilchrest B. Pigment content of cultured human melanocytes does not correlate with tyrosinase message level. Br. J. Dermatol., 125: 297-303, 1991; Potterf S. B., Muller J., Bernardini I., Tietze F., Kobayashi T., Hearing V. J., Gahl W. A. Characterization of a melanosomal transport system in murine melanocytes mediating entry of the melanogenic substrate tyrosine. J. Biol. Chem., 271: 4002-4008, 1996; Vijayasaradhi S., Bouchard B., Houghton A. N. The melanoma antigen gp 75 is the human homologue of the mouse b (brown) locus gene product. J. Exp. Med., 171: 1375-1380, 1990; Koning G., Morselt H., Velinova M., Donga J., Gorter A., Allen T., Zalipsky S., Kamps J., Scherphof G. Selective transfer of a lipophilic prodrug of 5-fluorodeoxyuridine from immunoliposomes to colon cancer cells. Biochim. Biophys. Acta, 1420: 153-167, 1999; Exploiting Tyrosinase Expression and Activity in Melanocytic Tumors: Quercetin and the Central Role of p53, Integr Cancer Ther Dec. 1, 2011 10:328-340; Molecular Basis of the extreme dilution mottled Mouse Mutation: A Combination Of Coding And Noncoding Genomic Alterations, J Biol Chem Feb. 11, 2005 280:4817-4824; Enzyme-Catalyzed Activation of Anticancer Prodrugs, Pharmacol. Rev. Mar. 1, 2004 56:53-102; Sendovski M, Kanteev M, Ben-Yosef V S, Adir N, Fishman A., First Structures of an Active Bacterial Tyrosinase Reveal Copper Plasticity, Journal of Molecular Biology, Volume 405, Issue 1, 7 Jan. 2011, Pages 227-237; Greta Faccioa, Kristiina Kruusb, Markku Saloheimob, Linda Thöny-Meyera, Bacterial tyrosinases and their applications, Process Biochemistry, Volume 47, Issue 12, December 2012, Pages 1749-1760; Hughes B W, Wells A H, Bebok Z, Gadi V K, Garver R I Jr, Parker W B, Sorscher E J, Bystander killing of melanoma cells using the human tyrosinase promoter to express the *Escherichia coli* purine nucleoside phosphorylase gene, Cancer Res. 1995 Aug. 1; 55(15):3339-45, each of which is expressly incorporated herein by reference in its entirety.

The present technology provides, according to various embodiments, live attenuated therapeutic bacterial strains that have improved ability compared to a parental strain in regard to the pharmacokinetic properties of enhanced circulation in the bloodstream and entry into, persistence and growth within tumors, by resisting immune elimination or lytic destruction, increased numbers of foci within tumors, increased colonization, expansion and persistence within tumors. It is the intention of these changes that the result in an overall increase in 1) the percentage of tumors targeted, 2) the number of individual locations (foci) within a tumor that are targeted, 3) the number of CFU/g that are found within the tumor, 4) the length of time that they reside within the tumor and 5) reduced immune clearance from the tumor, and, alone or collectively 6) increased antitumor activity.

One object is to select for one or more mutations that result in smaller sized bacteria with improved (increased) pharmacokinetics in blood through reduced elimination and improved penetration though the leaky tumor vasculature.

The present technology also has the objective of utilizing the enhanced permeability and retention (EPR) factor associated with tumor vasculature. To utilize the EPR effect, the bacteria should preferably be smaller than 650 nm in size, and more preferably less than 400 nm in size (Danhier et al., 2010, To exploit the tumor microenvironment: passive and active tumor targeting of nanocarriers for anticancer drug delivery. J. Control. Release 148: 135-146, expressly incorporated herein by reference in its entirety). Preferred bacteria therefore have as their width less than 650 nm, and more preferably less than 400 nm.

Another object is to generate bacteria with a protective sialic acid coat that results in improved (increased) pharmacokinetic half-life in blood, improved penetration though leaky tumor vasculature and reduced immune clearance. The non-limiting mechanisms by which sialic acid prevents immune clearance include reduced opsonization (i.e., reduced interaction with complement, ficolin, mannose binding protein, C-reactive protein, scavenger receptor, and/or antibodies) by increasing repulsive interaction with blood components and increasing surface hydrophobicty. The present invention is unlike vaccine vectors that express glycosylated antigens (Szymanski and Nothaft EP2611823, Peptide containing multiple n-linked glycosylation sequons, expressly incorporated herein by reference in its entirety) because the invention is directed toward reduced immune stimulation, detection or elimination, whereas vaccine vectors are designed to be detected and to stimulate the immune system.

Another object is to construct bacteria that alternately express external antigens such as O and H antigens under exogenous control of inducible promoters such that different antigens are controllably expressed at different times and result in bacteria with improved (increased) pharmacokinetics in blood and reduced immune clearance and reduce immune recognition upon repeated dosing.

Another object is to develop bacteria that deliver ligands against programmed cell death protein 1 (PD1) and/or its ligand (PD-L1 and PD-L2) or CTLA-4 which has the result of increased T-cells attacking tumors and increasing the habitable region of the tumor by bacteria through their killing of tumor cells and providing nutrients for the bacteria. Compositions and methods for inhibition of PD-1 or PD-L1/PD-L2 have been described by U.S. Pat. No. 6,803,192, US 20130202623 and PCT publication No. WO 10/027423 each of which is expressly incorporated by reference in its entirety Another object is to genetically modify the bacteria to express the *E. coli* tryptophanase which results in greater tumor cell killing and enhanced penetration of the bacteria within the tumor.

Another object is to genetically modify the bacteria to express and secrete mammalian or bacterial tyrosinase, as directly toxic principle or as a prodrug-converting enzyme. More broadly, other known prodrug converting enzymes secretable from the bacteria (e.g., *Salmonella*) may be employed, such as cytosine deaminase. Similarly, essential biochemical depleting enzymes may also be expressed, such as asparginase.

Another object is to increase serum resistance to components that act as opsonins which enhance elimination by phagocytic cells or directly interfere with or kill bacteria, including complement, antibodies, ficolin, scavenger receptor, C-reactive protein (CRP), the bactericidal/permeability-increasing protein (BPI) and mannose binding protein, by reducing their binding or prevention of their mode of action including resisting lytic destruction. The bacteria are selected for as previously described by Pawelek et al., WO/1996/040238, expressly incorporated herein by reference in its entirety, where the bacteria are recycled through tumors. The bacteria are further cycled one or more times through the blood (for selection of increased serum half-life and survival by selecting for their presence at extended times) and through the liver (for selection of increased survival against serum components and/or carbon dioxide ($CO_2$), bicarbonate ($HCO^{3-}$), carbonate ($CO_3^{2-}$) and/or carbonic acid ($H_2CO_3$ or $OC(OH)^2$). The vertebrates useful for cycling include mice, rats, guinea pigs, rabbits, dogs, cats, pigs, monkeys and humans. The subjects may be further exposed to carbogen (carbon dioxide and oxygen mixtures) during the selection. The selection may also take place ex vivo (i.e., blood drawn from a patient, or blood fed into a chemostat).

A further object provides a genetically engineered bacterium, optionally being genetically selected or mutated to have a reduced size compared to its parental strain, comprising at least one gene which causes or induces carbohydrate decoration of external components of the genetically engineered bacterium, being adapted for efficacious treatment of a neoplastic disease in the human or animal under non-lethal conditions.

The at least one gene may comprise at least one heterologous gene that produces sialic acids on an external surface of the bacterium.

The genetically engineered bacterium may further comprise inducible gene promoters adapted to control the genetically engineered bacterium to display heterologous surface antigens. The inducible surface antigens may be O-oligosaccharide antigens and/or flagellar (H) antigens.

The genetically engineered bacterium may comprise genetic modifications for producing a plurality of heterologous surface antigens on the genetically engineered bacterium, which are produced by the genetically engineered bacterium under control of multiple different inducible promoters.

The genetically engineered bacterium may comprise genetic modifications for producing a plurality of different heterologous surface antigens on a surface of the genetically engineered bacterium, which are all under control of an acetylsalicylic acid inducible promoter.

The parental strain comprises a bacterium of genus *Salmonella*, e.g., VNP 20009/YS1646.

The genetically engineered bacterium may be selected or mutated to grow to a maximum size of about 650 nm.

The neoplastic disease comprises may be disease associated with formation of a solid tumor in a host animal, e.g., having necrotic regions.

Administration of the genetically engineered bacterium to the human or animal may result in at least one of: increased numbers of colony forming units within the solid tumor compared to its parental strain; increased serum half-life compared to its parental strain; increased numbers of colony forming units within the solid tumor compared to its parental strain; and reduced immune elimination following repeated dosing compared to its parental strain.

The live genetically engineered bacterium may be provided in a pharmaceutically acceptable formulation suitable for administration to a human or animal, and the carbohydrate decoration of external components of the genetically engineered bacterium is effective for increasing a serum half-life of the live genetically engineered bacterium after administration to the human or animal in the pharmaceutically acceptable formulation.

It is also an object to provide a bacterium genetically engineered to provide an acetylsalicylic acid inducible promoter, which promotes expression of at least one antitumor protein by the bacterium. The bacterium may also have at least one gene which is heterologous, selected or mutated, optionally responsive to an acetyl salicylic acid inducible promoter or the same promoter as the at least one antitumor protein, which causes the bacterium to be decorated with carbohydrates in a heterologous decoration pattern. The at least one gene may comprise a plurality of genes, each responsive to an acetyl salicylic acid inducible promoter, effective for causing the bacterium to selectively display a different heterologous antigen in response to presence of acetyl salicylic acid.

The bacterium may comprise at least one gene which is heterologous, selected or mutated, which causes the bacterium to be decorated with carbohydrates in a heterologous decoration pattern.

A still further object provides a method for treating a neoplastic disease in a living human or animal, comprising: administering a pharmaceutically acceptable formulation containing a genetically engineered bacterium to the living human or animal having the neoplastic disease, the genetically engineered bacterium may optionally be genetically engineered or selected to have a reduced size compared to its parental strain and which grows to a maximum size of about 650 nm, having at least one gene which causes or induces carbohydrate decoration of external components of the genetically engineered bacterium in a pattern different from the parental strain; permitting the genetically engineered bacterium to grow within and then be cleared from the living human or animal to cause antitumor effects, which are non-lethal to the living human or animal.

Administration of the pharmaceutically acceptable formulation containing a genetically engineered bacterium to the human or animal may result in at least one of: increased numbers of colony forming units within the solid tumor compared to its parental strain; increased serum half-life compared to its parental strain; increased numbers of colony forming units within the solid tumor compared to its parental strain; and reduced immune elimination following repeated dosing compared to its parental strain.

The at least one gene may comprise at least one heterologous gene that produces sialic acids on an external surface of the bacterium.

The genetically engineered bacterium may further comprise inducible gene promoters adapted to control the genetically engineered bacterium to display at least one of heterologous O-oligosaccharide surface antigens and flagellar (H) antigens, further comprising inducing the inducible gene promoters.

Another object provides a live genetically engineered bacterium, comprising: at least one heterologous inducible gene which causes or induces carbohydrate decoration of external components of the live genetically engineered bacterium, at least one gene producing a functional gene product under control of an inducible promoter distinct from the at least one heterologous inducible gene, the live genetically engineered bacterium being adapted for administration to a human or animal and colonization of at least one tissue under non-lethal conditions.

The carbohydrate decoration may comprise sialic acid, O-oligosaccharide antigens, and/or H flagellar antigens, for example.

The gene product may comprise an enzyme which is secreted from the live genetically engineered bacterium in active form, such as an amino-acid degrading enzyme (e.g., tryptophanase, asparaginase) which is secreted from the live genetically engineered bacterium in active form and has anti-tumor activity against human or animal tumors colonized by the live genetically engineered bacterium.

The inducible promoter may comprise MarA, which is induced by presence of acetyl salicylic acid. The inducible promoter may also be responsive to at least one of tet, arabinose, hypoxia, a cellular SOS response promoter, X-rays, and mitomycin.

The at least one heterologous inducible gene which causes or induces carbohydrate decoration of external components of the genetically engineered bacterium may comprise a plurality of inducible genes having respectively different inducers. At least one of the plurality of inducible genes having respectively different inducers may be responsive to a pharmacological inducer which is not naturally found in human tissue. The at least one heterologous inducible gene and the at least one gene producing a gene product under control of an inducible promoter may each induced by a common inducer. The at least one heterologous inducible gene may comprise a plurality of inducible genes, having respectively different inducible promoters induced by different pharmacological agents not naturally found in humans, to thereby provide the live genetically engineered bacterium having a plurality of different surface antigen patterns under control of a selective presence of the different pharmacological agents.

The live genetically engineered bacterium may have a selective tropism for at least one type of tumor in a human or animal, and the functional gene product is effective for treating the at least one type of tumor, the live genetically engineered bacterium being provided within a pharmaceutically acceptable formulation for administration to the human or animal.

The genetically engineered bacterium may further comprise a heterologous acetyl salicylic acid inducible gene promoter adapted to control the genetically engineered bacterium to produce a gene product, further comprising administering acetylsalicylic acid to the human or animal to induce the gene product.

When administering self-replicating organisms, the minimum dose approximates a single in vivo replication competent organism or minimum infectious dose, which itself is approximated by an in vitro determined colony forming unit (CFU). Suitable dosage ranges are generally from about 1.0 c.f.u./kg to about $1\times10^{10}$ c.f.u./kg; optionally from about 1.0 c.f.u./kg to about $1\times10^{8}$ c.f.u./kg; optionally from about $1\times10^{2}$ c.f.u./kg to about $1\times10^{8}$ c.f.u./kg; optionally from about $1\times10^{4}$ c.f.u./kg to about $1\times10^{8}$ c.f.u./kg; and optionally from about $1\times10^{4}$ c.f.u./kg to about $1\times10^{10}$ c.f.u./kg. Effective doses may be extrapolated from dose-response curves derived from in vitro or animal model test systems. However, higher doses are preferred, in order to permit prompt initiation of therapeutic effect and avoid host immune response suppression of the organisms before they reach full therapeutic potential. In some cases, replication incompetent organisms may be used, e.g., where the organisms remain competent to produce biologically active products as discussed herein while not being able to replicate, in which case a dose may be, for example, in the range $10^{8}$ to $10^{10}$ organisms and determined by non-culture based methods (e.g., hemocytometer). The maximum dose of preferred organisms which display low toxicity and pathogenicity is in excess of $10^{10}$, and for orally or dermally administered probiotic species, gram scale doses may be administered.

The bacterial delivery vector may be attenuated, non-pathogenic, low pathogenic (including wild type), or a probiotic bacterium. The bacteria are introduced either systemically (e.g., parenteral, intravenous (IV), intramuscular (IM), intralymphatic (IL), intradermal (ID), subcutaneously (sub-q), local-regionally (e.g., intralesionally, intratumorally (IT), intraperitoneally (IP), topically, intathecally (intrathecal), by inhaler or nasal spray) or to the mucosal system through oral, nasal, pulmonary intravessically, enema or suppository administration. The terms "oral", "enteral", "enterally", "orally", "non-parenteral", "non-parenterally", and the like, refer to administration of a compound or composition to an individual by a route or mode along the alimentary canal. Examples of "oral" routes of administration include, without limitation, swallowing liquid or solid forms by the mouth, administration of a composition through a nasojejunal or gastrostomy tube, intraduodenal administration of a composition, and rectal administration, e.g., using suppositories that release a live bacterial strain described herein to the lower intestinal tract of the alimentary canal. Upon administration, the bacteria are able to undergo limited or unlimited replication, express, surface display, secrete and/or release the effector molecules and/or protease inhibitors with anti-cancer thereby providing a therapeutic benefit by reducing or eliminating the malignancy and/or neoplasia.

Bacteria of the invention have recognizable attributes in regard to their serum half-life and presence within tumors. For example, Toso et al., 2002 (Phase I Study of the Intravenous Administration of Attenuated *Salmonella typhimurium* to Patients with Metastatic Melanoma, Journal of Clinical Oncology, 20: 142-152, expressly incorporated herein by reference in its entirety) showed for example that a dose of $3\times10^{8}$ of the strain VNP20009 resulted in an average (in 6 patients) of approx. 65,000 CFU per ml of blood at 25 min, but only an average of 19 CFU/ml at 60 min., and only an average of 0.1 CFU/ml at 4 hrs, and only one patient in 6 had any CFU/ml at 12 hrs. Bacteria of the invention have significantly higher numbers of colony forming units at one or more times following 25 min, or have higher numbers of patients with greater than 0 CFU/ml at 12 hrs. A single patient in that treatment group received a second dose: that patient had 19,400 CFU/ml at 25 min for the first dose, but only 38 CFU/ml for the second dose.

Bacteria of the invention have significantly greater numbers of CFU/ml at 25 min upon subsequent doses. Patients in that same treatment group were also assessed for the presence of CFU/g of tumor tissue. Only one in six patients had any CFU/g in their tumor. Bacteria of the invention have significantly greater percentages of tumors colonized by bacteria. The one tumor that was colonized by the bacteria had 11,000 CFU/g of tumor tissue, compared to $10^9$ CFU/g in tumor tissue of mice (Luo et al., 2001, Antitumor effect of VNP20009, an attenuated *Salmonella* in murine tumor models. Oncol. Res. 12: 501-508, expressly incorporated herein by reference in its entirety). Bacteria of the invention have significantly CFU/g of tumor tissue. In the study by Toso et al., 2002, no antitumor activity was observed, whereas the bacteria of the invention have improved antitumor activity.

4. BRIEF DESCRIPTION OF THE DRAWINGS

5. DETAILED DESCRIPTION OF THE INVENTION

Figure 1A:
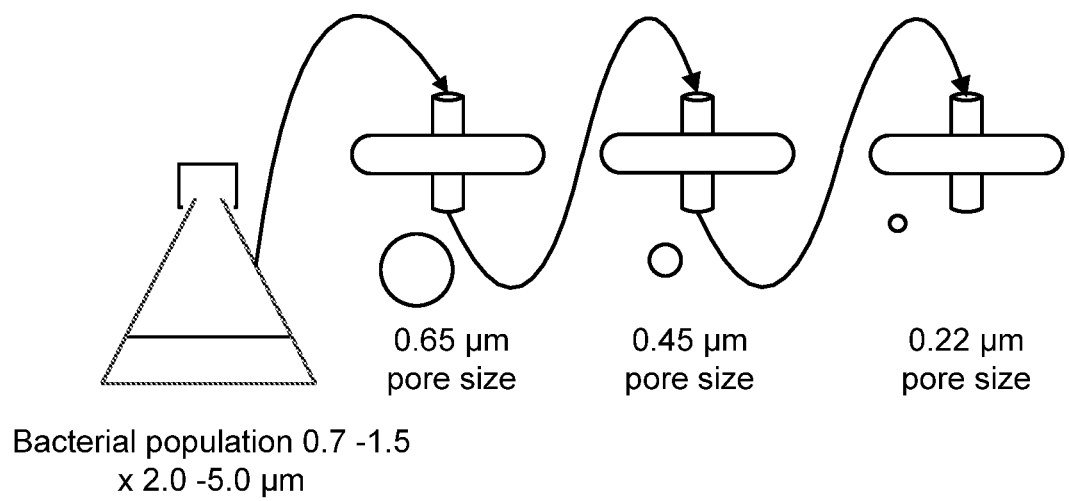
FIGS. 1A-1C show schematically a method for selection of bacteria with reduced size.
Figure 1B:
Figure 1C:
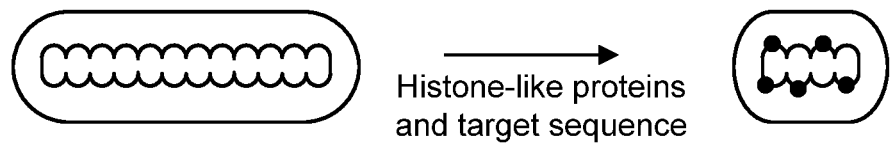

The present invention provides, according to various embodiments, bacteria with enhanced pharmacokinetics that have improved ability to distribute systemically, to persist longer within tumors, target tumors in multiple foci, targeted higher percentages of tumors, target tumors with increased numbers of bacteria, remove tumor cell immunosuppressive functions, increase the antitumor immune response and have enhanced tumor cell killing that alone or in combination, and result in increased antitumor activity.

For reasons of clarity, the detailed description is divided into the following subsections: 1) bacteria with reduced size, 2) bacteria with a protective sialic acid coat, 3) bacteria that alternately express external antigens such as O and H antigens under exogenous control of inducible promoters, 4) bacteria that deliver anti-immunosuppressive ligands against CTLA-4, programmed cell death protein 1 (PD1) and programmed cell death ligand (PD-L1) and 5) bacteria that express tryptophanase.

The present technology provides, according to various embodiments, improved live attenuated therapeutic bacterial strains that express one or more therapeutic molecules. The primary characteristic of the bacteria of certain embodiments of the invention is the improved targeting to tumors and reduced clearance from the blood (increased serum half-life) with enhanced antitumor activity. In one embodiment, the percent increase in effect is approximately 2% to approximately 95%, approximately 2% to approximately 75%, approximately 2% to approximately 50%, approximately 2% to about 40%, approximately 2% to about 30%, approximately 2% to about 25%, approximately 2% to about 20% or about 2% to approximately 10% greater than the parental strain of bacteria without expressing one or more of the modifications described herein under the same conditions.

5.1. Bacteria with Reduced Size.

Typical *Salmonella* are gram-negative rods 0.7-1.5 by 2.0-5.0 μm. *Salmonella* of the invention having smaller size are derived by several different means. Bacteria with smaller size are selected for their ability to pass thorough microporous sterilizing membranes followed by light and electron microscopic analysis. Because of their size, *Salmonella* do not typically pass through 0.65, 0.45 or 0.22 μM porous filters. The bacteria are thus selected for their ability to pass through successively smaller pore sizes. The present technology and methods may be used alone or in combination and with or without the FabH mutation known to reduce bacterial size (Wootton, 2012, Nature Rev. Microbiol. 10: 670-671, expressly incorporated herein by reference in its entirety). The bacteria may be further cycled through tumors as described by Pawelek et al. (U.S. Pat. No. 6,190,657 Vectors for the Diagnosis and Treatment of Solid Tumors Including Melanoma), expressly incorporated herein by reference in its entirety.

5.1.1. Bacterial Mutations.

Bacteria may be isolated by random mutagenesis using UV and nitrosoguanidine, or by transposon mutagenesis and selected for smaller size as described above. Alternatively, unsuppressed msbB strains (YS; Murray et al., 2001, Extragenic suppressors of msbB⁻ growth defects in *Salmonella*. J. Bacteriol. 183: 5554-5561) or partially suppressed msbB strains (Murray et al., 2007. PmrA(Con) Confers pmrHFIJKL-Dependent EGTA and Polymyxin Resistance on msbB *Salmonella* by Decorating Lipid A with Phosphoethanolamine. J. Bacteriology, 189: 5161-5169; Murray et. al., Hot spot for a large deletion in the 18-19 Cs region confers a multiple phenotype in *Salmonella enterica* serovar *typhimurium* strain ATCC 14028, J. Bacteriol, 186: 8516-8523 (2004), each of which is expressly incorporated herein by reference in its entirety) may be used to selected for spontaneous mutations or combination of selections thereof. The mutations can be identified by methods known to those skilled in the arts including genome sequencing.

5.1.2. Bacteria with Reduced Genome Size.

Bacteria with reduced genomes are generated by selecting for loss of functions that are associated with phenotypic markers. Methods are known to those skilled in the arts (Posfai et al., 2006, Emergent properties of reduced-genome *Escherichia coli*, Science 312: 1044-1046; Campbell et al., U.S. Pat. No. 8,178,339, Reduced genome *E. coli*, each of which is expressly incorporated herein by reference in its entirety) and selected for smaller size as described above.

5.1.3. Bacteria with Tighter Genome Packaging.

Bacteria with tighter genome packaging are produced by, e.g., 1) introducing the *Chlamydia* specific histone-like protein binding sequences AATAGGGTTTCTTTTAATAGAAAC SEQ ID NO: 001 and

AATAGGGATTCCAGTAACAACAAG SEQ ID NO: 002 into the chromosome using methods known to those skilled in the art (e.g., transposons, sucrose vector insertions, lambda red vector insertions) and heterologously expressing the *Chlamydia* (e.g., Genbank: CP002679.1) histone H1-I, histone-like proteins HC1 and HC2 or homologs or variants thereof (e.g., GenBank: L10193.1 Hc2 nucleoproteins hctB) using methods known to those skilled in the arts, and selecting for smaller size as described above.

5.2. Bacteria with a Protective Sialic Acid Coat.

The bacteria are engineered to be coated with sialic acid either by A) de novo synthesis or B) scavenged from the host. De novo synthesis of lipopolysaccharide with sialic acid is accomplished by heterologous expression of the genes necessary including but not limited to NeuA, NeuB, NeuC, SiaB, Lic3A, Lic3B, and SOAT (sialic acid O-acyl-transferase) as described by Severi et al., 2007 (Sialic acid utilization by bacterial pathogens, Microbiology 153: 2817-2822). De novo synthesis of a polysaccharide capsule with sialic acid is accomplished by the additional heterologous expression of NeuD, NeuS, NeuO, and Kps (capsule export system). Scavenging of sialic acid requires the additional presence of a sialidase, NanC, porins, SatABCD, SiaPQM and NanT. Heterologous expression is achieved using synthetic biology and methods known to those skilled in the art.

5.3. Bacteria that Alternately Express Surface Antigens Such as O and H Antigens Under Exogenous Control of Inducible Promoters.

The diverse range of *Salmonella* serotypes contains a variety of O-polysaccharide (O-antigen) and flagellar (H antigens) (Grimont, P. A. D & Weill, F. X. 2007. Antigenic Formulae of the *Salmonella* Serovars, WHO Collaborating Centre for Reference and Research on *Salmonella*, 9th edition). Exposure of the host to these antigens may lead to protective immunity. In the context of bacterial vectors, protective immunity may either eliminate the vector thereby reducing its antitumor effect or prevent secondary and tertiary dosing. The present technology provides a single bacterium that inducibly undergoes alternate expression of O and H antigens, alone or in simultaneous combination. Methods for deriving heterologous O-antigens have been described by Favre et al., WO/1997/014782, and Roland WO/2000/004919, each of which is expressly incorporated herein by reference in its entirety. O-antigen synthesis is directed by the rfb gene cluster which encodes enzymes involved in biosynthesis of the monomer sugar unit, and the rfc gene, which encodes the O-antigen polymerase responsible for the polymerization of the sugar unit into a high molecular weight polysaccharide chain (Sugiyama et al., 1991 Expression of the Cloned *Escherichia coli* 09 rfb Gene in Various Mutant Strains of *Salmonella typhimurium*, J. Bacteriol. 173:55-58; Collins et al. 1991, Molecular Cloning, Characterization, and Nucleotide Sequence of the rfc Gene, Which Encodes an O-Antigen Polymerase of *Salmonella typhimurium*, J. Bacteriol. 173:2521-2529, each of which is expressly incorporated herein by reference in its entirety). The antigens are chosen such that alternate expression does not have overlap. For example, the O-antigens of the *S. typhimurium* serovar are O: 1, 4, 5, 12, whereas those of *S. montevideo*, O: 6, 7, and those of $E_3$ group are O: 3, 15, 34. The genes may be part of a single synthetic operon (polycistronic), or may be separate, monocistronic constructs, with separate individual promoters of the same type used to drive the expression of their respective genes. The promoters may also be of different types, with different genes expressed by different constitutive or f promoters. Use of two separate inducible promoter for more than one antigen allows, when sufficient X-ray, tetracycline, arabinose methylalicylate or other inducer is administered following administration of the bacterial vector, their expression to occur simultaneously, sequentially, or alternating (repeated). A variety of inducible promoters are known including arabinose, (EP 1,655,370 A1, expressly incorporated by reference in its entirety), tetracycline inducible promoter (TET promoter), SOS-response promoters responsive to DNA damaging agents such as mitomycin, alkylating agents, X-rays and ultraviolet (UV) light such as the recA promoter, colicin promoters, sulA promoters and hypoxic-inducible promoters including but not limited to the PepT promoter (Bermudes et al., WO 01/25397, expressly incorporated herein by reference in its entirety), the arabinose inducible promoter ($Ara_{BAD}$) (Lossner et al., 2007, Cell Microbiol. 9: 1529-1537; WO/2006/048344) the methylsalicylate inducible promoter (Royo et al., 2007, Nature Methods 4: 937-942; WO/2005/054477, each of which is expressly incorporated herein by reference in its entirety). A single promoter may be used to drive the expression of more than one antigen gene, such multiple O-antigens O: 1, 4, 5, 12 engineered to be present on the chromosome. To achieve multiple alternating sets of antigens, coexistence of a set of alternative, non-overlapping antigens such as O: 6, 7 under control of a separate inducible promoter are constructed. Thus, a bacterial culture may be induced to have one set of antigens for a first injection, and may be induced to have a second set of antigens for a second injection, and so on. Similarly, following a first injection with induced expression of one set of antigens, the first inducer may be curtailed, and the inducer for the second set of antigens initiated, thus avoiding prolonged exposure to the immune systems and avoiding immune elimination.

A novel acetylsalicylic acid (aspirin)-inducible promoter is also encompassed based upon the *Salmonella* multiple antibiotic resistance operon (mar) promoter/operator regulon (Sulavik et al., 1997, The *Salmonella typhimurium* mar locus: molecular and genetic analyses and assessment of its role in virulence. J. Bacteriol. 179: 1857-1866; Barbosa and Levy, 2000 Differential expression of over 60 chromosomal genes in *Escherichia coli* by constitutive expression or MarA, J. Bacteriol 182: 3467-3474; Alekshun and Levy, 2004, The *Escherichia coli* mar locus-antibiotic resistance and more, ASM News 70: 451-456), Genbank accession number U54468.1 (which, by itself, does not confer antibiotic resistance), each of which is expressly incorporated herein by reference in its entirety. The regulon consists of the mar promoter/operator region, the MarR negative regulator, the MarA positive regulator, and the downstream start codon (ATG) that is used for expression of the gene(s) of interest such as the rfb cluster. Alternatively, use of the mar regulon also encompasses inducible expression of other anti-cancer proteins, protease inhibitors and targeted toxins and antitumor enzymes and/or genetically engineered phage and phagemids (Bermudes U.S. Pat. No. 8,524,220, Protease Inhibitor: Protease sensitivity expression system composition and methods improving the therapeutic activity and specificity of proteins delivered by bacteria; U.S. Pat. No. 8,241,623, Protease Sensitivity Expression System; U.S. Pat. No. 8,623,350 Protease inhibitor protease sensitivity expression system and method improving the therapeutic activity and specificity of proteins and phage and phagemids delivered by bacteria) or combinations with antivascular agents, such as platelet factor 4 and thrombospondin, alone or in combination (Bermudes et al., U.S. Pat. Nos. 6,962, 696, 7,452,531 Compositions and Methods for Tumor-Targeted Delivery of Effector Molecules) and other anticancer agents (e.g., WO2009/126189, WO03/014380, WO/2005/018332, WO/2008/073148, US 2003/0059400 U.S. Pat. Nos. 7,452,531, 7,354,592, 6,962,696, 6,923,972, 6,863, 894, 6,685,935, 6,475,482, 6,447,784, 6,190,657 and 6,080, 849, each of which is expressly incorporated herein by reference in its entirety). The DNA containing the upstream regulon promoter/operator, the MarR and MarA genes and ending with the start codon (ATG; caps) to which may be fused as the initiating codon a gene or genes of interest is encompassed by:

SEQ ID NO: 003
cagtgtgcaagttaatatcctctacaacctataacctgtaattatcaatt agttacaagttatcacagcacaataccccggacgccttttagcaaatcgt ggcatcggccaattcatttagttgacttatacttgcctgggcaatagtat ctgacgaaattaattacttgccggggcaaccattttgaaaagcaccagtg atctgttcaATGaaatcattccgctgggtcgcttgatctacatggtaaat cagaaaaaagatcgcctgttaaataactatttatccccgctggatatcac cgcaacacagtttaaagtgctttgctcgatacgctgcgcgggatgtatta ccccggttgaacttaaaaaagtgctgtctgtcgatctcggcgcattgacg cggatgctcgaccgcctgctgtgcaaaggctggatcgaaagactgccgaa tcctaatgacaaacgcggcgtactggtgaagctaacgccggacggcgcgg caatttgtgagcaatgtcatcaacgaccagggcaagacctgcatcaggaa ttaacaaaaaacttaacggcggacgaagtggcaacgcttgagtatttgct caagaaaattctgccgtagacaaaaaagaggtATGacgatgtccagacgc aacactgacgctattactattcatagcattttggactggatcgaggataa cctggagtcgccgctctcactggaaaaagtgtctgagcgttcaggatatt ccaaatggcacctgcaacggatgtttaaaaaagagaccggtcattcatta ggccaatacatccgcagccgtaaaatgacggaaatcgcgcaaaaattaaa agagagcaacgagcccattctctatctggcggaacgctatggctttgagt cacagcaaacattgacccggacgttcaaaaactattttgatgtgccgcca cacaaataccggatcaccaatatgcatggcgaatcacggtatatgctgcc gctgaaccatggcaactactagtttgtttatgcgccacgcgaagagcacc

ATG

In another embodiment, the Seq. ID NO.:003 bp 1-209, with the ATG of MarR at 210-212 is used as the start codon. In a more preferred embodiment, the Seq. ID NO.:003 bp 1-632, with the ATG of MarA at 633-635 is used as the start codon. Optionally, in any of the promoters described above, a bacterial termination sequence can be placed upstream of bp 1 (Peters et al., 2011 Bacterial transcriptional terminators: the RNA3'end chronicals, J. Mol. Biol. 412: 793-813), expressly incorporated herein by reference in its entirety.

5.4. Bacteria that Deliver Ligands Against Immunosuppressive Factors Including Programmed Cell Death Protein 1 Ligand (PD-L1), PD-L1 Receptor (PD-1) or CTLA-4.

Bacteria that reside within tumors rely upon nutrients obtained from the host. While necrotic tissue formed due to tissue hypoxia is believed to be one of the primary sources of nutrients for bacteria colonizing tumors, cell death due to immune functions such as those of cytotoxic T-cells attaching tumor cells also have the potential to contribute to the growth and expansion of intratumoral bacteria by providing nutrients. An object of one embodiment of the technology is to use the bacteria described herein alone or in combination with other aspects of the technology that increase the bacteria's ability to colonize and expand within tumors. Ligands against immuno-suppressive factors such PD-L1 and CTLA-4 include antibodies, affibodies (protein A affinity-based ligands), armadillo repeat protein-based scaffolds, adnectins, anticalins, lipocalins, Kunitz domain-based binders, avimers, knottins, fynomers, atrimers and DARPins (designed ankyrin repeat proteins) and cytotoxic T-lymphocyte associated protein-4 (CTLA4)-based binders (Weidle et al., 2013 The emerging role of new protein scaffold-based agents for treatment of cancer. Cancer Genomics Protomics 10: 155-168, expressly incorporated herein by reference in its entirety). Ligands such as those against PD-L1 such as those described by Gao et al., 2014 (Small peptides elicit anti-tumor effects in CT26 model through blocking PD-L1/ PD-1 (TUM2P.900, Journal of Immunology 192 (1 Supplement) 71.24) are expressed using secretion proteins described above, such as fusions with YebF. Anti-CLA-4 anticalin PRS-010 is also engineered as a YebF fusion, and may optionally contain a protease cleavage site for release of the anticalin within the tumor. CLA-4 anticalins may also be expressed by filamentous phage or as bacterial surface displayed (WO2012072806A1; Muteins of human liopcalin 2 with affinity for CTLA-4; 20090042785 Compound with affinity for the cytotoxic T lymphocyte-associated antigen (CTLA-4; 20100285564 Anticalins; 20100160612 Muteins Of Tear Lipocalin With Affinity For The T-Cell Coreceptor CD4, each of which is expressly incorporated herein by reference in its entirety). Affibodies are generated as described by Felwisch and Tomachev 2012, Enginnering of affibody molecules for therapy and diagnosis. Methods Molecular Biol 899: 103-126). DARPins are designed and screened for as previously described (Stumpp and Amstutz 2007, DARPins: a true alternative to antibodies, Curr Opin Drug Discov. Devel. 10: 159-153; Zahnd et al., 2010, Efficient tumor targeting with high-affinity designed ankyrin repeat proteins: Effects of Affinity and Molecular Size, Cancer Res 2010; 70:1595-1605; WO/2013022091 Therapeutic Agent For Autoimmune Diseases Comprising PD-1 Agonist), each of which is expressly incorporated herein by reference in its entirety. The localized production of the PD-L1 or CTLA-4 antagonists is distinctly different than systemic administration of antagonists such as antibodies, because systemic administration of PD-L1 or CTLA-4 antagonists has the potential to have systemic immune collateral damages, whereas the intratumoral production limits the T-cell response to the tumor environment. Combination with smaller size bacteria, alternating surface antigens and tryptophanase (see below) further enhance the overall antitumor effect.

5.5. Bacteria that Express the Tryptophanase.

Bacterial production of metabolites that are toxic to tumor cells such as indole, a product of tryptophanase, is used to enhance bacterial spread within the tumor by killing tumor cells by the production of the indole metabolite that the bacteria are not themselves affected by. The tumor cells are further starved for tryptophan by the depletion of tryptophan by tryptophanase. The combination of these effects is further enhanced by the other pharmacokinetic enhancements, tumor penetration, persistence and intra-tumoral spreading. Expression of tryptophanase may use the *Escherichia coli* genes or any homologous genes; those of the enterobacteriaceae are a preferred embodiment. In *E. coli* which are encoded by a transcribed leader region, tnaL (also known as tnaC), and two larger structural genes, where tnaA, which encodes the degradative enzyme and tnaB which together with the tnaL product are involved in tryptophan transport. In *E. coli* the genes exist as an operon and are expressed using a single promoter, such as the constitutive promoter or an inducible promoter. Alternatively, the endogenous tryptophanase or a modified tryptophanase promoter (Sitney et al., 1996, Use of a Modified Tryptophanase Promoter to Direct High-Level Expression of Foreign Proteins in *E. coli*, Ann. N.Y. Acad. Sci. 782: 297-310, expressly incorporated herein by reference in its entirety) may be used. The genes encode the 3 peptides:

TnaL(TnaC): MNILHICVTSKWFNIDNKIVDHRP
SEQ ID NO: 004

SEQ ID NO: 005
TnaA: MENFKHLPEPFRIRVIEPVKRTTRAYREEAIIKSGMN
PFLLDSEDVFIDLLTDSGTGAVTQSMQAAMMRGDEAYSGSRSY
YALAESVKNIFGYQYTIPTHQGRGAEQIYIPVLIKKREQEKGL
DRSKMVAFSNYFFDTTQGHSQINGCTVRNVYIKEAFDTGVRYD
FKGNFDLEGLERGIEEVGPNNVPYIVATITSNSAGGQPVSLAN
LKAMYSIAKKYDIPVVMDSARFAENAYFIKQREAEYKDWTIEQ
ITRETYKYADMLAMSAKKDAMVPMGGLLCMKDDSFFDVYTECR
TLCVVQEGFPTYGGLEGGAMERLAVGLYDGMNLDWLAYRIAQV
QYLVDGLEEIGVVCQQAGGHAAFVDAGKLLPHIPADQFPAQAL
ACELYKVAGIRAVEIGSFLLGRDPKTGKQLPCPAELLRLTIPR
ATYTQTHMDFIIEAFKHVKENAANIKGLTFTYEPKVLRHFTAK
LKEV

SEQ ID NO: 006
TnaB: MTDQAEKKHSAFWGVMVIAGTVIGGGMFALPVDLAGA
WFFWGAFILIIAWFSMLHSGLLLLEANLNYPVGSSFNTITKDL
IGNTWNIISGITVAFVLYILTYAYISANGAIISETISMNLGYH
ANPRIVGICTAIFVASVLWLSSLAASRITSLFLGLKIISFVIV
FGSFFFQVDYSILRDATSSTAGTSYFPYIFMALPVCLASFGFH
GNIPSLIICYGKRKDKLIKSVVFGSLLALVIYLFWLYCTMGNI
PRESFKAIISSGGNVDSLVKSFLGTKQHGIIEFCLLVFSNLAV
ASSFFGVTLGLFDYLADLFKIDNSHGGRFKTVLLTFLPPALLY
LIFPNGFIYGIGGAGLCATIWAVIIPAVLAIKARKKFPNQMFT
VWGGNLIPAIVILFGITVILCWFGNVFNVLPKFG

The complete sequence of the coding region from the start of the first peptide to the stop of the 3$^{rd}$ peptide is:

SEQ ID NO: 007
ATGaatatcttacatatatgtgtgacctcaaaatggttcaatattgacaa
caaaattgtcgatcaccgcccttgatttgccttctgtagccatcaccag
agccaaaccgattagattcaatgtgatctatttgtttgctatatcttaat
tttgccttttgcaaaggtcatctctcgtttatttacttgttttagtaaat
gatggtgcttgcatatatctggcgaattaatcggtatagcagatgtaa
tattcacagggatcactgtaattaaaataaatgaaggattatgtaatgga
aaactttaaacatctccctgaaccgttccgcattcgtgttattgagccag
taaaacgtaccactcgcgcttatcgtgaagaggcaattattaaatccggt
atgaacccgttcctgctggatagcgaagatgtttttatcgatttactgac
cgacagcggcaccggggcggtgacgcagacatgcaggctgcgatgatgc
gcggcgacgaagcctacagcggcagtcgtagctactatgcgttagccgag
tcagtgaaaaatatctttggttatcaatacaccattccgactcaccaggg ccgtggcgcagagcaaatctatattccggtactgattaaaaaaacgcgagc
aggaaaaaggcctggatcgcagcaaaatggtggcgttctctaactatttc
tttgataccacgcagggccatagccagatcaacggctgtaccgtgcgtaa
cgtctatatcaaagaagccttcgatacgggcgtgcgttacgactttaaag
gcaactttgaccttgagggattagaacgcggtattgaagaagttggtccg
aataacgtgccgtatatcgttgcaaccatcaccagtaactctgcaggtgg
tcagccggtttcactggcaaacttaaaagcgatgtacagcatcgcgaaga
aatacgatattccggtggtaatggactccgcgcgctttgctgaaaacgcc
tatttcatcaagcagcgtgaagcagaatacaaagactggaccatcgagca
gatcacccgcgaaacctacaaatatgccgatatgctggcgatgtccgcca
agaaagatgcgatggtgccgatgggcggcctgctgtgcatgaaagacgac
agcttctttgatgtgtacaccgagtcagaaccctttgcgtggtgcagga
aggcttcccgacatatggcggcctggaaggcggcgcgatggagcgtctgg
cggtaggtctgtatgacggcatgaatctcgactggctggcttatcgtatc
gcgcaggtacagtatctggtcgatggtctggaagagattggcgttgtctg
ccagcaggcgggcggtcacgcggcattcgttgatgccggtaaactgttgc
cgcatatcccggcagaccagttcccggcacaggcgctggcctgcgagctg
tataaagtcgccggtatccgtgcggtagaaattggctctttcctgttagg
ccgcgatccgaaaaccggtaaacaactgccatgcccggctgaactgctgc
gtttaaccattccgcgcgcaacatatactcaaacacatatggacttcatt
attgaagcctttaaacatgtgaaagagaacgcggcgaatattaaaggatt
aacccttacgtacgaaccgaaagtattgcgtcacttcaccgcaaaactta
aagaagtttaattaatactacagagtggctataaggatgttagccactct
cttaccctacatcctcaataacaaaaatagccttcctctaaaggtggcat
catgactgatcaagctgaaaaaaagcactctgcattttggggtgttatgg
ttatagcaggtacagtaattggtggaggtatgtttgctttacctgttgat
cttgccggtgcctggttttctggggtgcctttatccttatcattgcctg
gttttcaatgcttcattccgggttattgttattagaagcaaatttaaatt
atcccgtcggctccagttttaacaccatcaccaaagatttaatcggtaac
acctggaacattatcagcggtattaccgttgccttcgttctctatatcct
cacttatgcctatatctctgctaatggtgcgatcattagtgaaacgatat
caatgaatttgggttatcacgctaatccacgtattgtcgggatctgcaca
gccattttcgttgccagcgtattgtggttaagttcgttagccgccagtcg
tattacctcattgttcctcgggctgaagattatctcctttgtgatcgtgt
ttggttctttttcttccaggtcgattactccattctgcgcgacgccacc
agctccactgcgggaacgtcttacttcccgtatatctttatggctttgcc
ggtgtgtctggcgtcatttggtttccacggcaatattcccagcctgatta
tttgctatggaaaacgcaaagataagttaatcaaaagcgtggtatttggt
tcgctgctggcgctggtgatttatctcttctggctctattgcaccatggg
gaatattccgcgagaaagctttaaggcgattatctcctcaggcggcaacg

```
                                            -continued
ttgattcgctggtgaaatcgttcctcggcaccaaacagcacggcattatc gagttttgcctgctggtgttctctaacttagctgttgccagttcgttctt tggtgtcacgctggggttgttcgattatctggcggacctgtttaagattg ataactcccacggcgggcgtttcaaaaccgtgctgttaaccttcctgcca cctgcgttgttgtatctgatcttcccgaacggctttatttacgggatcgg cggtgccgggctgtgcgccaccatctgggcggtcattattcccgcagtgc ttgcaatcaaagctcgcaagaagtttcccaatcagatgttcacggtctgg ggcggcaatcttattccggcgattgtcattctctttggtataaccgtgat tttgtgctggttcggcaacgtctttaacgtgttacctaaatttggcTAA
```

It is understood that other enzymes, such as tyrosinase, may be genetically engineered within the Salmonella, instead of or together with the tryptophanase, in accordance with known principles and the discussion herein.

5.6. Bacteria with Enhanced Resistance to Serum.

Bacterial with enhanced resistance to serum and serum components are derived by several additional means, and can be used alone or in combination with sialic acid modifications and/or $CO_2$ resistance.

5.6.1. Selection for increased serum half-life. Mutants can be selected from spontaneous populations, or mutagenized populations as described above. Bacteria with improved serum half-life can be selected by taking blood samples and selecting the bacteria that are found at the tail end of the serum circulation, re-injecting the same bacteria after regrowth, and again selecting for bacteria at the end of the circulation in serum as previously applied to bacteriophage (Merril et al., 1996, Long-circulating bacteriophage as antibacterial agents, PNAS 93: 3188-3192), expressly incorporated herein by reference in its entirety. The selection may be performed in live animals, including mice, rats, guinea pigs, rabbits, pigs, dogs, cats, monkeys and human volunteers. The procedure may also be carried out in vitro, using blood from any of the above donors by successive passages and isolation of individual colonies resistant to complement and/or other serum components.

5.6.2. Expression of serum-resistance genes. Expression or over-expression of serum resistance genes can be accomplished by conventional heterologous expression methods known to those skilled in the arts. The serum resistome of E. coli has been described (Phan et al., 2013 The serum resistome of a globally disseminated multidrug resistant uropathogenic Escherichia coli clone, PLoS Genetics DOI: 10.1371/journal.pgen.1003834, incorporated by reference in its entirety). Serum resistance genes also include the Salmonella Rck (resistance to complement killing) and PagC proteins or its homologues from E. coli (Lom) Yersinia entercolitica (ail) and Enterobacter cloacae (OmpX) (Heffernan E J, et al., 1992. The Salmonella typhimurium virulence plasmid complement resistance gene rck is homologous to a family of virulence-related outer membrane protein genes, including pagC and ail. J. Bacteriol. 174: 84-91; Ho et al., 2011, Functional Recruitment of Human Complement Inhibitor C4b-Binding Protein to Outer Membrane Protein Rck of Salmonella PLoS ONE 6(11): e27546. doi:10.1371/journal.pone.0027546), Cirillo D M, et al., 1996. Identification of a domain in Rck, a product of the Salmonella typhimurium virulence plasmid, required for both serum resistance and cell invasion. Infect. Immun. 64: 2019-2023), each of which is expressly incorporated herein by reference in its entirety. Antibodies to Rck may also be used to select strains with increased expression. Resistance can also be obtained by expression of other genes, such as the melittin resitance gene pqaB (Baker et al., 1999, The Salmonella typhi melittin resistance gene pqaB affects intracellular growth in PMA-differentiated U937 cells, Polymyxin B resistance and lipopolysaccharide, Microbiology 145: 367-378), expressly incorporated herein by reference in its entirety. Furthermore, when the melittin resistance gene is expressed, the lytic protein melittin or melittin conjugates to targeted peptides may be used as antitumor agents (Liu et al., 2013, A novel melittin-MhIL-2 fusion protein inhibits the growth of human ovarian cancer SKOV3 cells in vitro and in vivo tumor growth, Cancer Immunol. Immunotherapy 62: 889-895), expressly incorporated herein by reference in its entirety. Other targeting peptides fused to melittin may be any of those from the references herein.

6. FIGURE LEGEND

The figures show compositions and methods to modify bacteria of the present technology.

FIGS. 1A-1C. Bacteria with reduced size. FIG. 1A. The mechanism for selecting bacteria with reduced size by passage of a population of bacteria containing spontaneous mutants, induced mutants and/or suppressor mutants through progressively smaller syringe cartridge microporous filters of 0.65, 0.45 and 0.22 μm. FIG. 1B. Facilitation of reduced size bacteria by genome reduction. Following genome reduction methods, the bacteria may be selected for reduced size as shown in FIG. 1A. FIG. 1C. Facilitation of reduced size bacteria by genome compaction through addition of histone-like proteins from Chalamydia and the appropriate target sequence. Following genome reduction methods, the bacteria may be selected for reduced size as shown in FIG. 1A. The process may be further combined with the method of FIG. 1B.

FIGS. 2A-2C. Bacteria with a protective sialic acid coat. FIG. 2A. The genes necessary for LPS sialyation are cloned into and expressed by the bacteria, resulting in the LPS O-antigen being sialylated (Severi et al., 2007, Sialic acid utilization by bacterial pathogens, Microbiology 153: 2817-2822, expressly incorporated herein by reference in its entirety). FIG. 2B. The genes necessary for PSA capsule biosynthesis and export are cloned into and expressed by the bacteria, resulting in a sialic acid capsule. FIG. 2C. The genes for sialic acid scavenging and utilization are cloned into and expressed by the bacteria, resulting in the LPS O-antigen being sialyated.

FIGS. 3A-3C Bacteria with inducible expression of alternate surface antigens. FIG. 3A. The wild type rfb gene cluster and rfc gene encoding the O: 1, 4, 5, 12 antigen, and the wild type H1 flagellar antigen, all with wild type promoters. FIG. 3B. Three different rfb gene cluster with the rfc gene encoding the O: 1, 4, 5, 12 antigens, and the H1 flagellar antigen under control of the sulA (x-ray inducible) promoter the O: 6, 7 antigens, and the H2 flagellar antigen under control of the tet (tetracycline) inducible promoter, and; the O: 3, 15, 34 antigens and the H3 flagellar antigen under control of the ara (arabinose) inducible promoter. Successive treatment with X-rays, tetracycline and arabinose respectively results in alternate expression of non-overlapping surface antigens. FIG. 3C. the mar regulon which consists of the mar promoter/operator, the MarR negative regulatory gene, the MarA positive regulatory gene, and a downstream start codon (ATG) which would normally comprise the start of the MarB coding sequence, which is used for the rfb O-antigen gene cluster. Alternatively, the MarA regulon may be used for inducible expression of other anti-cancer effector genes.

Figure 4:
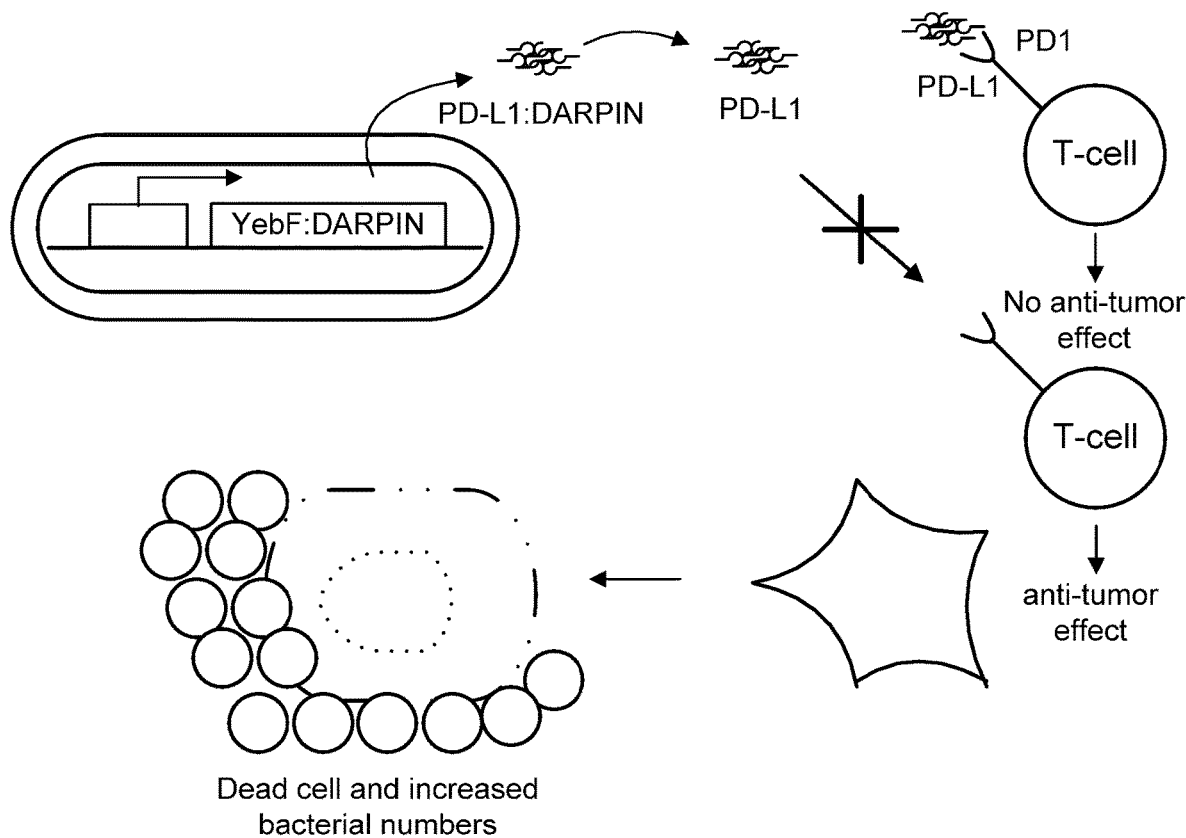
FIG. 4 shows bacteria delivering ligands against PD-1 ligand (PDL-1).

FIG. 4. Bacteria delivering ligands against PD-1 ligand (PD-L1). Bacteria expressing a PD-L1 antagonist (a YebF fusion of an anti-PD-L1 DARPin) results in blocking the PD-L1 signal, thereby activating T-cells that destroy tumor cells and increase the number of bacteria within the tumor.

Figure 5:
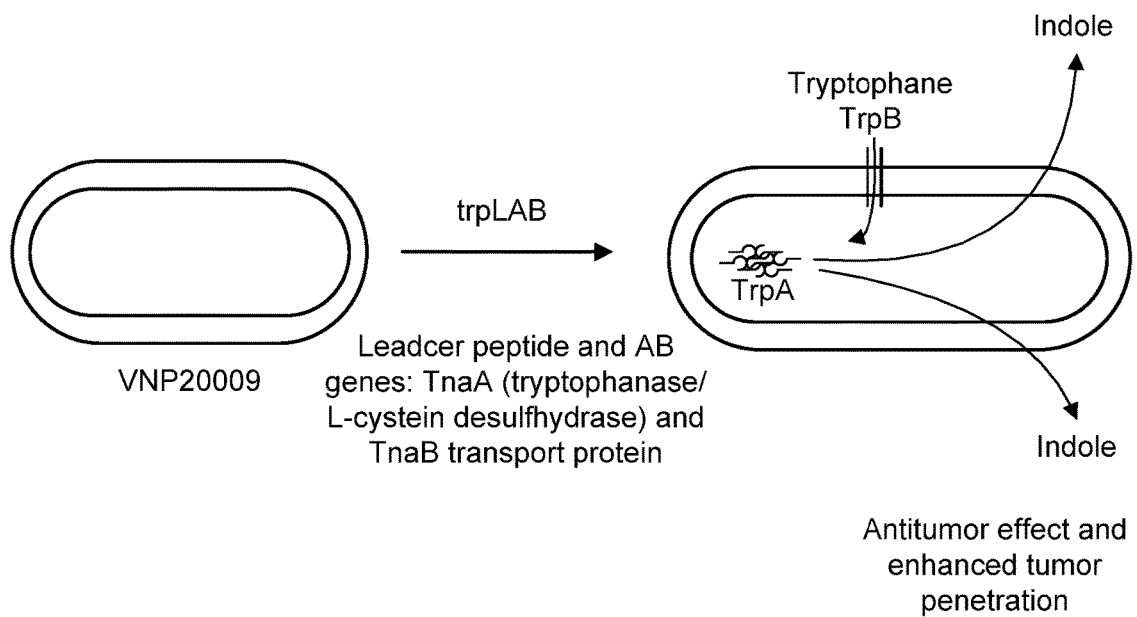
FIG. 5 shows bacteria that express the *E. coli* tryptophanase.

FIG. 5 shows bacteria that express the *E. coli* tryptophanase. The operon for tryptophanase including trypLAB are cloned and expressed in the bacteria, resulting in tumor cell toxicity, antitumor activity and increased tumor penetration of the bacteria.

7. EXAMPLES

In order to more fully illustrate the invention, the following examples are provided.

Example 1

Isolation of Bacteria with Reduced Size Based on Spontaneous Mutagenesis.

By way of example, the attenuated antineoplastic bacteria, or precursors to antineoplastic bacteria, are selected from a pool of mutants. The mutants may either be those that are spontaneous within a normal genetic background (i.e., a normal population), spontaneous mutants in a non-suppressed environmentally sensitive genetic background (e.g., msbB⁻), or spontaneous mutants within a mutator background. Bacteria of a normal genetic background and mutator backgrounds (e.g., mutL, mutS, mutH, alone or in combination) are grown from low density, e.g., a single colony inoculated into 100 ml of standard media such as Luria broth. Bacteria of an environmentally sensitive genetic background, such as strain YS1 (Murray et al., 2001, Extragenic suppressors of msbB⁻ growth defects in *Salmonella*. J. Bacteriol. 183: 5554-5561, expressly incorporated herein by reference in its entirety) are grown from low density, e.g., a single colony inoculated into 100 ml of media wherein the media contains a substance to which the bacteria are sensitive, such as 6 mM EGTA.

Bacteria with reduced size are selected for by passage through successively smaller pore sizes. Selection begins with passage through a 0.65 µM filter. Bacteria obtained this way are rechecked by repassage through the filter, with a high percentage of passage indicating bacteria with smaller size. These bacteria are then again subjected to the initial growth conditions above and then again selected for passage through a filter except that a 0.45 µM pore size is used. The process is then repeated for a 0.22 µM pore size. The mutations resulting in the bacteria passing through smaller pore sizes are determined by standard genetic means (Murray et al., 2001) or by genome sequencing.

Example 2

Isolation of Bacteria with Reduced Size Based on Random Mutagenesis.

The selection process described above is applied to bacteria that have been randomly mutagenized. Random mutagenesis can consist of either chemically/physically induced mutations such as those caused by nitrosoguanidine and ultraviolet light (Pawelek et al., 1997). The selection process described above is applied to bacteria that have been randomly mutagenized.

Example 3

Generation of Bacteria with a Protective Sialic Acid Coat.

Figure 2A:
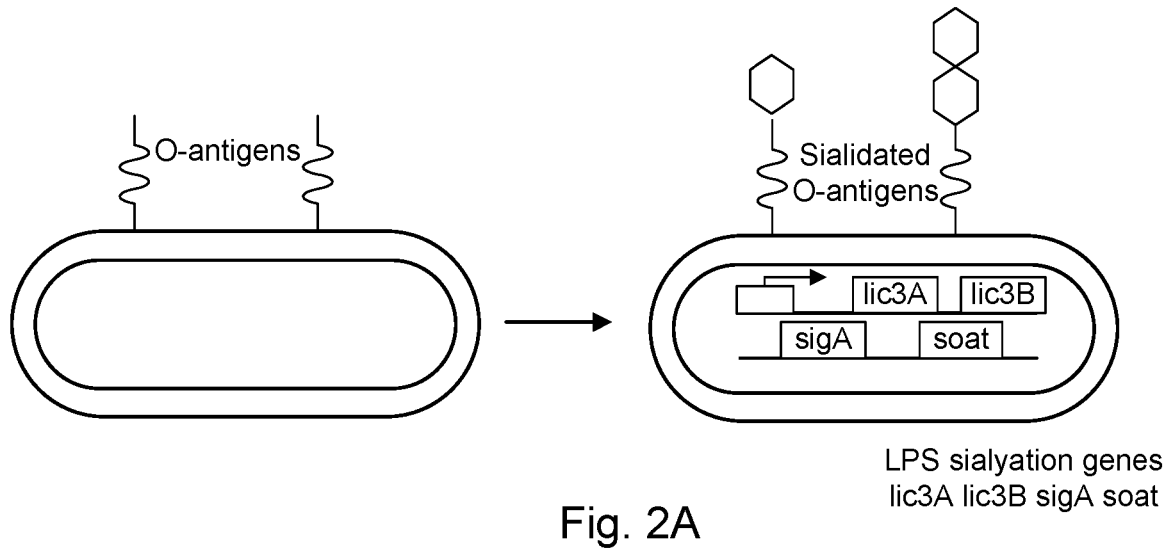
FIGS. 2A-2C show bacteria with a protective sialic acid coat.
Figure 2B:
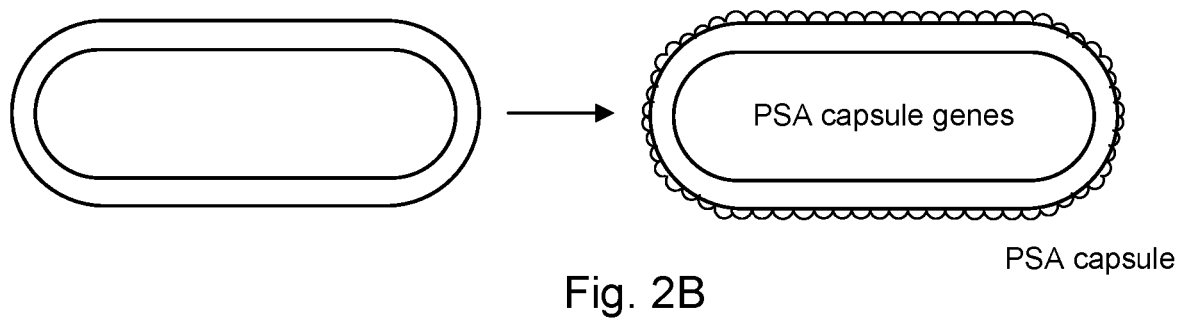
Figure 2C:
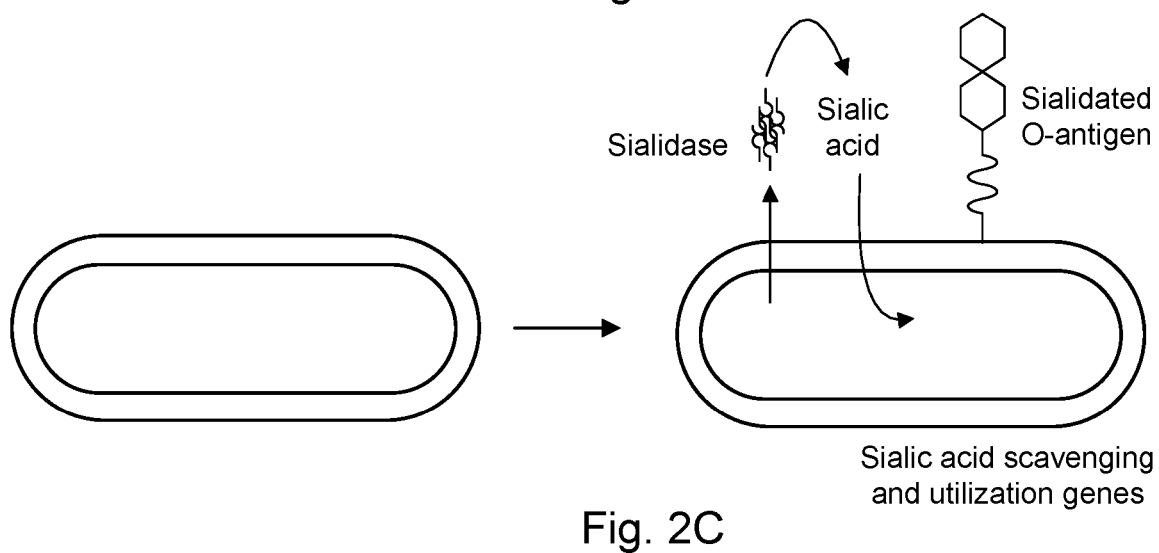

De novo synthesis of lipopolysaccharide with sialic acid is accomplished by heterologous expression of NeuA, NeuB, NeuC, SiaB, Lic3A, Lic3B, and SOAT (sialic acid O-acyltransferase) (Severi et al., 2007, Sialic acid utilization by bacterial pathogens, Microbiology 153: 2817-2822, expressly incorporated herein by reference in its entirety) as shown in FIGS. 2A-2C. Heterologous expression is achieved using synthetic biology and methods known to those skilled in the arts, including the methods described by King et al., 2009 (Tumor-targeted *Salmonella typhimurium* overexpressing cytosine deaminase: a novel, tumor-selective therapy, Meth. Mol. Biol. 542: 649-659), expressly incorporated herein by reference in its entirety. Induction of the sialic acid coat may be performed in vitro during manufacturing, or in vivo, following systemic administration.

Example 4

Generation of Bacteria with Inducible Expression of Alternate Surface Antigens.

Figure 3A:
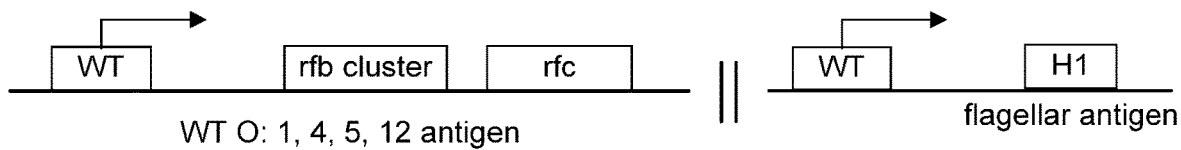
FIGS. 3A-3C show bacteria with inducible expression of alternate surface antigens, and the Mar regulon for use as an inducible promoter.
Figure 3B:
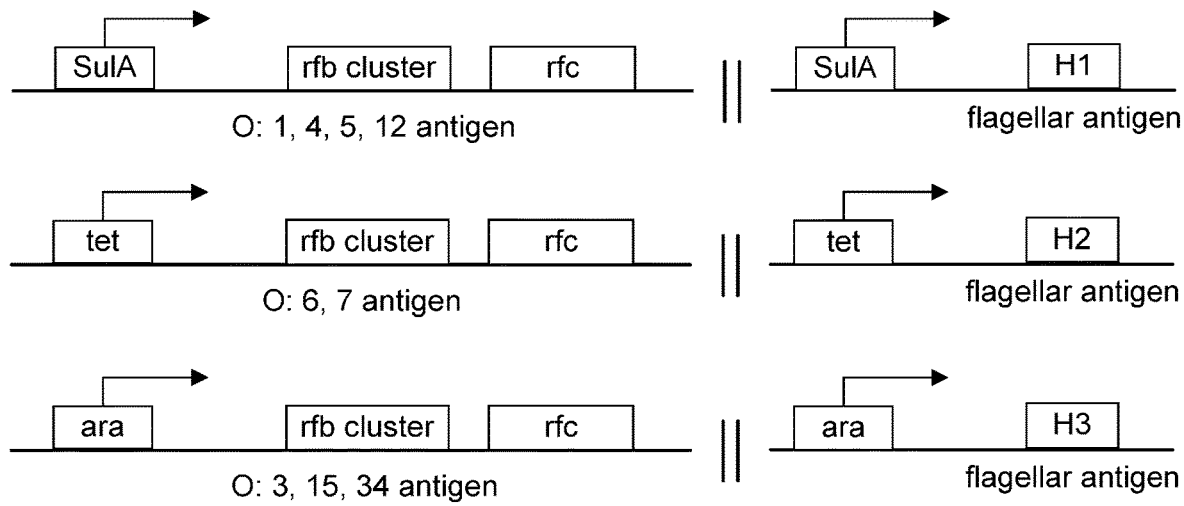
Figure 3C:
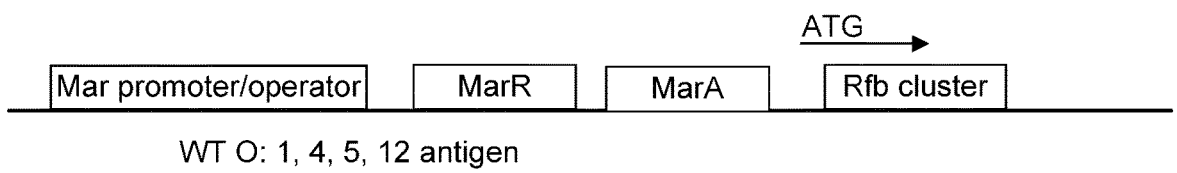

Methods for deriving heterologous O-antigens include methods known to those skilled in the arts, including those described by Favre et al., WO/1997/014782, and Roland WO/2000/004919, each of which is expressly incorporated herein by reference in its entirety. O-antigen synthesis is directed by the rfb gene cluster which encodes enzymes involved in biosynthesis of the monomer sugar unit, and the rfc gene, which encodes the O-antigen polymerase responsible for the polymerization of the sugar unit into a high molecular weight polysaccharide chain (Sugiyama et al., 1991 Expression of the Cloned *Escherichia coli* O9 rfb Gene in Various Mutant Strains of *Salmonella typhimurium*, J. Bacteriol. 173:55-58; Collins et al. 1991, Molecular Cloning, Characterization, and Nucleotide Sequence of the rfc Gene, Which Encodes an O-Antigen Polymerase of *Salmonella typhimurium*, J. Bacteriol. 173:2521-2529), each of which is expressly incorporated herein by reference in its entirety. The antigens are chosen such that alternate expression does not have overlap. For example, the O-antigens of the *S. typhimurium* serovar are O: 1, 4, 5, 12, whereas those of *S. montevideo*, O: 6, 7, and those of $E_3$ group are O: 3, 15, 34. The rfb gene cluster and rfc gene may be part of a single synthetic operon (polycistronic), or may be separate, monocistronic constructs, with separate individual promoters of the same type used to drive the expression of their respective genes. Use of separate inducible promoter for more than one antigen allows for their expression to occur simultaneously, sequentially, or alternating (repeated) depending upon which inducers are administer (FIGS. 3A-3C). Thus, to achieve multiple alternating sets of antigens, coexistence of a set of alternative, non-overlapping under control of a separate inducible promoter are constructed. Thus, a bacterial culture may be induced to have one set of antigens for a first injection, and may be induced to have a second set of antigens for a second injection, and so on. Similarly, following a first injection with induced expression of one set of antigens, the first inducer may be curtailed, and the inducer for the second set of antigens initiated, thus avoiding prolonged exposure to the immune systems and avoiding immune elimination.

Example 5

Generation of Bacteria Delivering Ligands Against PD-1 Ligand (PDL-1).

Ligands against PDL1 include antibodies, affibodies (protein A affinity-based ligands), adnectins, anticalins and DARPins (designed ankyrin repeat proteins). Ligands against PDL1 such as affibodies and DARPins are expressed using secretion proteins described above, such as fusions with YebF (FIG. 4). Affibodies are generated as described by Felwisch and Tomachev 2012, Engineering of affibody molecules for therapy and diagnosis. Methods Molecular Biol 899: 103-126). DARPins are designed and screened for as previously described (Stumpp and Amstutz 2007, DARPins: a true alternative to antibodies, Curr Opin Drug Discov. Devel. 10: 159-153; Zahnd et al., 2010, Efficient tumor targeting with high-affinity designed ankyrin repeat proteins: Effects of Affinity and Molecular Size, Cancer Res 2010; 70:1595-1605; WO/2013022091 Therapeutic Agent For Autoimmune Diseases Comprising PD-1 Agonist), each of which is expressly incorporated herein by reference in its entirety. Combination with smaller size bacteria, alternating surface antigens and tryptophanase (see below) further enhance the overall antitumor effect.

Example 6

Generation of Bacteria that Express the *E. coli* Tryptophanase.

Expression of tryptophanase and demonstration of enhanced antitumor activity may be conducted as follows. Cloning of the tryptophanase operon uses methods known to those skilled in the arts, including PCR-based cloning (Forward primer=Tryp Kpn Nsi F1 TCggtacccAGGAGGAAttcaCCATGCATaatatcttacatatatgtgtgAcctcaaaat SEQ ID NO: 008 and reverse primer=Tryp Xba R1 gatcTCTAGAgaaggatTTAgccaaatttaggtaacac SEQ ID NO: 009). Cloning into an expression vector such as a modified pTrc99a with the arabinose promoter

```
                                     SEQ ID NO: 010
GGGGGCGGCCGCAAGAAACCAATTGTCCATATTGCATCAGACATTGCCGT

CACTGCGTCTTTTACTGGCTCTTCTCGCTAACCAAACCGGTAACCCCGCT

TATTAAAAGCATTCTGTAACAAAGCGGGACCAAAGCCATGACAAAAACGC

GTAACAAAAGTGTCTATAATCACGGCAGAAAAGTCCACATTGATTATTTG

CACGGCGTCACACTTTGCTATGCCATAGCATTTTTATCCATAAGATTAGC

GGATCCTACCTGACGCTTTTTATCGCAACTCTCTACTGTTTCTCCATACC

CGTTTTTTTGGGCTAGCGAATTCGAGCTCGGTACCCAGGAGGAATTCACC

ATGGAATTCGAGCTCGGTACCCGGGGATCCTCTAGAGTCGACCTGCAGGC

ATGCAAGCTTGGCTGTTTTGGCGGATGAGAGAAGATTTTCAGCCTGATAC

AGATTAAATCAGAACGCAGAAGCGGTCTGATAAAACAGAATTTGCCTGGC

GGCAGTAGCGCGGTGGTCCCACCTGACCCCATGCCGAACTCAGAAGTGAA

ACGCCGTAGCGCCGATGGTAGTGTGGGGTCTCCCCATGCGAGAGTAGGGA

ACTGCCAGGCATCAAATAAAACGAAAGGCTCAGTCGAAAGACTGGGCCTT

TCGTTTTATCTGTTGTTTGTCGGTGAACGCTCTCCTGAGTAGGACAAATC

CGCCGGGAGCGGATTTGAACGTTGCGAAGCAACGGCCCGGAGGGTGGCGG

GCAGGACGCCCGCCATAAACTGCCAGGCATCAAATTAAGCAGAAGGCCAT

CCTGACGGATGGCCTTTTTGCGTTTCTACAAACTCTTTTTGTTTATTTTT

CTAAATACATTCAAATATGTATCCGCTCATGAGACAATAACCCTGATAAA

TGCTTCAATAATATTGAAAAAGGAAGAGTATGAGTATTCAACATTTCCGT
```

-continued

```
GTCGCCCTTATTCCCTTTTTTGCGGCATTTTGCCTTCCTGTTTTTGCTCA

CCCAGAAACGCTGGTGAAAGTAAAAGATGCTGAAGATCAGTTGGGTGCAC

GAGTGGGTTACATCGAACTGGATCTCAACAGCGGTAAGATCCTTGAGAGT

TTTCGCCCCGAAGAACGTTTTCCAATGATGAGCACTTTTAAAGTTCTGCT

ATGTGGCGCGGTATTATCCCGTGTTGACGCCGGGCAAGAGCAACTCGGTC

GCCGCATACACTATTCTCAGAATGACTTGGTTGAGTACTCACCAGTCACA

GAAAAGCATCTTACGGATGGCATGACAGTAAGAGAATTATGCAGTGCTGC

CATAACCATGAGTGATAACACTGCGGCCAACTTACTTCTGACAACGATCG

GAGGACCGAAGGAGCTAACCGCTTTTTTGCACAACATGGGGGATCATGTA

ACTCGCCTTGATCGTTGGGAACCGGAGCTGAATGAAGCCATACCAAACGA

CGAGCGTGACACCACGATGCCTACAGCAATGGCAACAACGTTGCGCAAAC

TATTAACTGGCGAACTACTTACTCTAGCTTCCCGGCAACAATTAATAGAC

TGGATGGAGGCGGATAAAGTTGCAGGACCACTTCTGCGCTCGGCCCTTCC

GGCTGGCTGGTTTATTGCTGATAAATCTGGAGCCGGTGAGCGTGGGTCTC

GCGGTATCATTGCAGCACTGGGGCCAGATGGTAAGCCCTCCCGTATCGTA

GTTATCTACACGACGGGGAGTCAGGCAACTATGGATGAACGAAATAGACA

GATCGCTGAGATAGGTGCCTCACTGATTAAGCATTGGTAACTGTCAGACC

AAGTTTACTCATATATACTTTAGATTGATTTAAAACTTCATTTTTAATTT

AAAAGGATCTAGGTGAAGATCCTTTTTGATAATCTCATGACCAAAATCCC

TTAACGTGAGTTTTCGTTCCACTGAGCGTCAGACCCCGTAGAAAAGATCA

AAGGATCTTCTTGAGATCCTTTTTTTCTGCGCGTAATCTGCTGCTTGCAA

ACAAAAAAACCACCGCTACCAGCGGTGGTTTGTTTGCCGGATCAAGAGCT

ACCAACTCTTTTTCCGAAGGTAACTGGCTTCAGCAGAGCGCAGATACCAA

ATACTGTCCTTCTAGTGTAGCCGTAGTTAGGCCACCACTTCAAGAACTCT

GTAGCACCGCCTACATACCTCGCTCTGCTAATCCTGTTACCAGTGGCTGC

TGCCAGTGGCGATAAGTCGTGTCTTACCGGGTTGGACTCAAGACGATAGT

TACCGGATAAGGCGCAGCGGTCGGGCTGAACGGGGGGTTCGTGCACACAG

CCCAGCTTGGAGCGAACGACCTACACCGAACTGAGATACCTACAGCGTGA

GCTATGAGAAAGCGCCACGCTTCCCGAAGGGAGAAAGGCGGACAGGTATC

CGGTAAGCGGCAGGGTCGGAACAGGAGAGCGCACGAGGGAGCTTCCAGGG

GGAAACGCCTGGTATCTTTATAGTCCTGTCGGGTTTCGCCACCTCTGACT

TGAGCGTCGATTTTTGTGATGCTCGTCAGGGGGCGGAGCCTATGGAAAA

ACGCCAGCAACGCGGCCTTTTTACGGTTCCTGGCCTTTTGCTGGCCTTTT

GCTCACATGTTCTTTCCTGCGTTATCCCCTGATTCTGTGGATAACCGTAT

TACCGCCTTTGAGTGAGCTGATACCGCTCGCCGCAGCCGAACGACCGAGC

GCAGCGAGTCAGTGAGCGAGGAAGCGGAAGAGCGCCTGATGCGGTATTTT

CTCCTTACGCATCTGTGCGGTATTTCACACCGCATATG
``` using KpnI and XbaI restriction endonucleases operably links the inducible ara promoter to a start codon (ATG) and results in a polycistronic message that produces all three peptides.

Successful expression of tryptophanase is determined by the addition of Kovac's reagent, which consists of isoamyl alcohol and par-dimethylaminobenzaldhyde in concentrated hydrochloric acid; a positive reaction is indicated by a red color. Determination of antitumor activity is performed according to the methods of Pawelek et al. (1997, Tumor-targeted *Salmonella* as a novel anticancer vector, Cancer Research 57: 4537-4544), expressly incorporated herein by reference in its entirety, with one control being mice bearing melanoma tumors without any treatment, a second control being the parental *Salmonella* VNP20009 without the tryptophanase, and a test group consisting of the VNP20009 expressing the tryptophanase. The expression plasmid is transformed to a suitable *Salmonella* strain, such as VNP20009 (Low, et al., 2004, Construction of VNP20009, a novel, genetically stable antibiotic sensitive strain of tumor-targeting *Salmonella* for parenteral administration in humans, Methods Mol Med 90: 47-60) and used to treat mice for preclinical studies (Pawelek et al., 1997, Tumor-targeted *Salmonella* as a novel anticancer agent, Cancer Research 57: 4537-4544; Low et al., 1999, Lipid A mutant *Salmonella* with suppressed virulence and TNF-alpha induction retain tumor-targeting in vivo, Nature Biotechnol. 17: 37-41; Lossner et al., 2007, Cell Microbiol. 9: 1529-1537; WO/2006/048344; Swofford et al., 2014 Biotechnology and Bioengineering 111: 1233-1245), and humans for clinical studies (Toso et al., 2002, Phase I study of the intravenous administration of attenuated *Salmonella typhimurium* to patients with metastatic melanoma, J. Clin. Oncol 20: 142-152), each of which is expressly incorporated herein by reference in its entirety.

Example 7

Selection of Bacteria with Increased Serum Survival and Increased Circulation Time.

Bacteria with increased serum circulation time are selected from natural populations, mutagenized populations, suppressed strains, partially suppressed strains, as described above. By way of specific example, strains with improved serum half-life may be selected for starting with the clinical strain VNP20009.

VNP20009 are injected into a 20 g mouse at $1 \times 10^6$ CFU/mouse. Bacteria are periodically sampled from blood, at 15 min, 30 min, 60 min, 120 min, 240 min, 480 min, 960 min, 1920 min and plated by serial dilutions of $10^0$-$10^{-6}$ and incubated overnight at 37 C. The next day, bacteria are selected from 1) the longest time point with viable bacteria and 2) from the longest time point at the highest dilution. All the bacteria on the plate from the longest time point and the highest dilution are pooled, grown overnight (approx. $10^9$ CFU/ml) and reinjected at the original concentration, and reisolated using the times and plating as above. The process may then be repeated. Individual bacteria from the plate from the longest time point and the highest dilution are then individually tested and compared to other bacteria from the same plate, and to the original VNP20009. Bacteria with at least a 30% increase, more preferably a 50% increase, and more preferably a 100% increase, and more preferably a greater than 100% increase are useful for antitumor studies (Pawelek et al., 1997). The above process may be repeated with a weight-adjusted dose, for rats, guinea pigs, rabbits, dogs, cats, pigs, monkeys or human volunteers. The process may also be scaled for the blood volume of a mouse (approx. 3 ml) to use of ex vivo human blood in vivo using sizes dependent upon availability and convenience. Ex vivo blood studies may also be performed, for example, in vacutainers, or in a chemostat using continuous fresh venous blood.

Example 8

Selection of Bacteria with Increased Survival in Blood with High CO2

Bacteria with increased survival in blood with high $CO_2$ are selected from natural populations, mutagenized populations, suppressed strains, partially suppressed strains, as described above. By way of specific example, strains with improved serum half-life may be selected for starting with the clinical strain VNP20009.

VNP20009 are injected into a 20 g mouse at $1 \times 10^6$ CFU/mouse, and the mice are exposed to carbogen (oxygen; 70% CO2 30%, or variations thereof). Bacteria are periodically sampled from blood, at 15 min, 30 min, 60 min, 120 min, 240 min, 480 min, 960 min, 1920 min and plated by serial dilutions of $10^0$-$10^{-6}$ and incubated overnight at 37 C. The next day, bacteria are selected from 1) the longest time point with viable bacteria and 2) from the longest time point at the highest dilution. All the bacteria on the plate from the longest time point and the highest dilution are pooled, grown overnight (approx. $10^9$ CFU/ml) and reinjected at the original concentration, and reisolated using the times and plating as above. The process may then be repeated. Individual bacteria from the plate from the longest time point and the highest dilution are then individually tested and compared to other bacteria from the same plate, and to the original VNP20009. Bacteria with at least a 30% increase, more preferably a 50% increase, and more preferably a 100% increase, and more preferably a greater than 100% increase are useful for antitumor studies (Pawelek et al., 1997). The above process may be repeated with a weight-adjusted dose, for rats, guinea pigs, rabbits, dogs, cats, pigs, monkeys or human volunteers. The process may also be scaled for the blood volume of a mouse (approx. 3 ml) to use of ex vivo human blood in vivo using sizes dependent upon availability and convenience. Ex vivo blood studies may also be performed, for example, in vacutainers, or in a chemostat using continuous fresh venous blood, and blood exposed to carbogen.

Example 9

Pharmaceutically Acceptable Formulations

Pharmaceutically acceptable formulations may be provided for delivery by other various routes e.g. by intramuscular injection, subcutaneous delivery, by intranasal delivery (e.g. WO 00/47222, U.S. Pat. No. 6,635,246), intradermal delivery (e.g. WO02/074336, WO02/067983, WO02/087494, WO02/0832149 WO04/016281, each of which is expressly incorporated herein by reference it its entirety) by transdermal delivery, by transcutaneous delivery, by topical routes, etc. Injection may involve a needle (including a microneedle), or may be needle-free. See, e.g., U.S. Pat. Nos. 7,452,531, 7,354,592, 6,962,696, 6,923,972, 6,863,894, 6,685,935, 6,475,482, 6,447,784, 6,190,657, 6,080,849 and US Pub. 2003/0059400, each of which is expressly incorporated herein by reference.

Bacterial vector vaccines are known, and similar techniques may be used for the present bacteria as for bacterial vaccine vectors (U.S. Pat. No. 6,500,419, Curtiss, In: New Generation Vaccines: The Molecular Approach, Ed., Marcel Dekker, Inc., New York, N.Y., pages 161-188 and 269-288 (1989); and Mims et al, In: Medical Microbiology, Eds., Mosby-Year Book Europe Ltd., London (1993)). These known vaccines can enter the host, either orally, intranasally or parenterally. Once gaining access to the host, the bacterial vector vaccines express an engineered prokaryotic expression cassette contained therein that encodes a foreign antigen(s). Foreign antigens can be any protein (or part of a protein) or combination thereof from a bacterial, viral, or parasitic pathogen that has vaccine properties (New Generation Vaccines: The Molecular Approach, supra; Vaccines and Immunotherapy, supra; Hilleman, Dev. Biol. Stand., 82:3-20 (1994); Formal et al, Infect. Immun. 34:746-751 (1981); Gonzalez et al, J. Infect. Dis., 169:927-931 (1994); Stevenson et al, FEMS Lett., 28:317-320 (1985); Aggarwal et al, J. Exp. Med., 172:1083-1090 (1990); Hone et al, Microbial. Path., 5:407-418 (1988); Flynn et al, Mol. Microbiol., 4:2111-2118 (1990); Walker et al, Infect. Immun., 60:4260-4268 (1992); Cardenas et al, Vacc., 11:126-135 (1993); Curtiss et al, Dev. Biol. Stand., 82:23-33 (1994); Simonet et al, Infect. Immun., 62:863-867 (1994); Charbit et al, Vacc., 11:1221-1228 (1993); Turner et al, Infect. Immun., 61:5374-5380 (1993); Schodel et al, Infect. Immun., 62:1669-1676 (1994); Schodel et al, J. Immunol., 145:4317-4321 (1990); Stabel et al, Infect. Immun., 59:2941-2947 (1991); Brown, J. Infect. Dis., 155:86-92 (1987); Doggett et al, Infect. Immun., 61:1859-1866 (1993); Brett et al, Immunol., 80:306-312 (1993); Yang et al, J. Immunol., 145:2281-2285 (1990); Gao et al, Infect. Immun., 60:3780-3789 (1992); and Chatfield et al, Bio/Technology, 10:888-892 (1992)). Delivery of the foreign antigen to the host tissue using bacterial vector vaccines results in host immune responses against the foreign antigen, which provide protection against the pathogen from which the foreign antigen originates (Mims, The Pathogenesis of Infectious Disease, Academic Press, London (1987); and New Generation Vaccines: The Molecular Approach, supra). See also: Formal et al, Infect. Immun., 34:746-751 (1981); Wick et al, Infect. Immun., 62:4542-4548 (1994)); Hone et al, Vaccine, 9:810-816 (1991); Tacket et al, Infect. Immun., 60:536-541 (1992); Hone et al, J. Clin. Invest., 90:412-420 (1992); Chatfield et al, Vaccine, 10:8-11 (1992); Tacket et al, Vaccine, 10:443-446 (1992); van Damme et al, Gastroenterol., 103:520-531 (1992) (*Yersinia pestis*), Noriega et al, Infect. Immun., 62:5168-5172 (1994) (*Shigella* spp), Levine et al, In: *Vibrio cholerae*, Molecular to Global Perspectives, Wachsmuth et al, Eds, ASM Press, Washington, D.C., pages 395-414 (1994)(*Vibrio cholerae*), Lagranderie et al, Vaccine, 11:1283-1290 (1993); Flynn, Cell. Molec. Biol., 40(Suppl.1):31-36 (1994)(*Mycobacterium* strain BCG), Schafer et al, J. Immunol., 149:53-59 (1992)(*Listeria monocytogenes*), each of which is expressly incorporated herein by reference.

The bacteria are generally administered along with a pharmaceutically acceptable carrier and/or diluent. The particular pharmaceutically acceptable carrier an/or diluent employed is not critical to the present invention unless otherwise specific herein (or in a respective incorporated referenced relevant to the issue). Examples of diluents include a phosphate buffered saline, buffer for buffering against gastric acid in the stomach, such as citrate buffer (pH 7.0) containing sucrose, bicarbonate buffer (pH 7.0) alone (Levine et al, J. Clin. Invest., 79:888-902 (1987); and Black et al J. Infect. Dis., 155:1260-1265 (1987), expressly incorporated herein by reference), or bicarbonate buffer (pH 7.0) containing ascorbic acid, lactose, and optionally aspartame (Levine et al, Lancet, 11:467-470 (1988), expressly incorporated herein by reference). Examples of carriers include proteins, e.g., as found in skim milk, sugars, e.g., sucrose, or polyvinylpyrrolidone. Typically, these carriers would be used at a concentration of about 0.1-30% (w/v) but preferably at a range of 1-10% (w/v).

Set forth below are other pharmaceutically acceptable carriers or diluents which may be used for delivery specific routes. Any such carrier or diluent can be used for administration of the bacteria of the invention, so long as the bacteria are still capable of invading a target cell. In vitro or in vivo tests for invasiveness can be performed to determine appropriate diluents and carriers. The compositions of the invention can be formulated for a variety of types of administration, including systemic and topical or localized administration. Lyophilized forms are also included, so long as the bacteria are invasive upon contact with a target cell or upon administration to the subject. Techniques and formulations generally may be found in Remington's Pharmaceutical Sciences, Meade Publishing Co., Easton, Pa., expressly incorporated herein by reference in its entirety. For systemic administration, injection is preferred, including intramuscular, intravenous, intraperitoneal, and subcutaneous. For injection, the composition, e.g., bacteria, of the invention can be formulated in liquid solutions, preferably in physiologically compatible buffers such as Hank's solution or Ringer's solution.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound. For buccal administration the compositions may take the form of tablets or lozenges formulated in conventional manner.

For administration by inhalation, the pharmaceutical compositions for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the composition, e.g., bacteria, and a suitable powder base such as lactose or starch.

The pharmaceutical compositions may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The pharmaceutical compositions may also be formulated in rectal, intravaginal or intraurethral compositions such as suppositories or retention enemas, e.g., containing conventional suppository bases such as cocoa butter or other glycerides.

See also U.S. Pat. No. 6,962,696, expressly incorporated herein by reference in its entirety.

The present invention provides a pharmaceutical composition comprising a pharmaceutically acceptable carrier and an attenuated tumor-targeted bacteria comprising one or more nucleic acid molecules encoding one or more primary effector molecules operably linked to one or more appropriate promoters. The present invention provides a pharmaceutical composition comprising a pharmaceutically acceptable carrier and an attenuated tumor-targeted bacteria comprising one or more nucleic acid molecules encoding one or more primary effector molecules and one or more secondary effector molecules operably linked to one or more appropriate promoters.

The present invention provides a pharmaceutical composition comprising a pharmaceutically acceptable carrier and a bacterium.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil, olive oil, and the like. Saline is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the therapeutic attenuated tumor-targeted bacteria, in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a suspending agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The amount of the pharmaceutical composition of the invention which will be effective in the treatment or prevention of a solid tumor cancer will depend on the nature of the cancer, and can be determined by standard clinical techniques. In addition, in vitro assays may optionally be employed to help identify optimal dosage ranges. The precise dose to be employed in the formulation will also depend on the route of administration, and the seriousness of the cancer, and should be decided according to the judgment of the practitioner and each patient's circumstances. However, suitable dosage ranges are generally from about 1.0 c.f.u./kg to about $1\times10^{10}$ c.f.u./kg; optionally from about 1.0 c.f.u./kg to about $1\times10^{8}$ c.f.u./kg; optionally from about $1\times10^{2}$ c.f.u./kg to about $1\times10^{8}$ c.f.u./kg; optionally from about 1 $10^{4}$ c.f.u./kg to about $1\times10^{8}$ c.f.u./kg; and optionally from about $1\times10^{4}$ c.f.u./kg to about $1\times10^{10}$ c.f.u./kg. Effective doses may be extrapolated from dose-response curves derived from in vitro or animal model test systems.

Various delivery systems are known and can be used to administer a pharmaceutical composition of the present invention. Methods of introduction include but are not limited to intradermal, intramuscular, intraperitoneal, intravenous, subcutaneous, intrathecal, intranasal, epidural, and oral routes. Methods of introduction may also be intratumoral (e.g., by direct administration into the area of the tumor).

The compositions may be administered by any convenient route, for example by infusion or bolus injection, by absorption through epithelial or mucocutaneous linings (e.g., oral mucosa, rectal and intestinal-mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved by, for example, and not by way of limitation, local infusion during surgery, by injection, by means of a catheter, or by means of an implant, said implant being of a porous, non-porous, or gelatinous material, including membranes, such as Silastic® membranes, or fibers. In one embodiment, administration can be by direct injection at the site (or former site) of a malignant tumor or neoplastic or pre-neoplastic tissue.

The attenuated tumor-targeted bacteria comprising one or more primary effector molecules and optionally, one or more secondary effector molecules may be delivered in a controlled release system. The attenuated tumor-targeted bacteria comprising one or more fusion proteins of the invention and optionally, one or more effector molecules may also be delivered in a controlled release system. In one embodiment, a pump may be used (see Langer, supra; Sefton, CRC Crit. Ref. Biomed. Eng. 14:201 (1987); Buchwald et al., 1980, Surgery 88:507; and Saudek et al., 1989, N. Engl. J. Med. 321:574), expressly incorporated herein by reference in their entirety. In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J. Macromol. Sci. Rev. Macromol. Chem: 23:61 (1983); see also Levy et al., 1985, Science 228:190; During et al., 1989, Ann. Neurol. 25:351; and Howard et al., 1989, J. Neurosurg. 71:105, expressly incorporated herein by reference in their entirety). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984), expressly incorporated by reference in its entirety).

Other controlled release systems are discussed in the review by Langer (1990, Science 249:1527-1533, expressly incorporated herein by reference in its entirety) and may be used in connection with the administration of the attenuated tumor-targeted bacteria comprising one or more primary effector molecule(s) and optionally, one or more secondary effector molecule(s).

The invention also provides a pharmaceutical pack or kit comprising one or more containers filled with one or more of the ingredients of the pharmaceutical compositions of the invention. Optionally associated with such container(s) can be a notice in the form prescribed by governmental agency regulating the manufacture, use or sale of pharmaceuticals or biological products, which notice reflects approval by the agency of manufacture, use or sale for human administration.

The present invention also provides methods for treating a solid tumor comprising administering to a human or animal in need thereof, a pharmaceutical composition of the invention and at least one other known cancer therapy. In a specific embodiment, a human or animal with a solid tumor cancer is administered a pharmaceutical composition of the invention and at least one chemotherapeutic agent. Examples of chemotherapeutic agents include, but are not limited to, cisplatin, ifosfamide, taxanes such as taxol and paclitaxol, topoisomerase I inhibitors (e.g., CPT-11, topotecan, 9-AC, and GG-211), gemcitabine, vinorelbine, oxaliplatin, 5-fluorouracil (5-FU), leucovorin, vinorelbine, temodal, cytochalasin B, gramicidin D, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin homologs, and cytoxan.

The present invention includes the sequential or concomitant administration of pharmaceutical composition of the invention and an anti-cancer agent such as a chemotherapeutic agent. In a specific embodiment, the pharmaceutical composition of the invention is administered prior to (e.g., 2 hours, 6 hours, 12 hours, 1 day, 4 days, 6 days, 12 days, 14 days, 1 month or several months before) the administration of the anti-cancer agent. In another specific embodiment, the pharmaceutical composition of the invention is administered subsequent to (e.g., 2 hours, 6 hours, 12 hours, 1 day, 4 days, 6 days, 12 days, 14 days, 1 month or several months after) the administration of an anti-cancer agent. In a specific embodiment, the pharmaceutical composition of the invention is administered concomitantly with an anti-cancer agent. The invention encompasses combinations of anti-cancer agents and attenuated tumor-targeted bacteria engineered to express one or more nucleic acid molecules encoding one or more effector molecules and/or fusion proteins that are additive or synergistic.

The invention also encompasses combinations of anti-cancer agents and attenuated tumor-targeted bacteria engineered to express one or more nucleic acid molecules encoding one or more effector molecules and/or fusion proteins that have different sites of action. Such a combination provides an improved therapy based on the dual action of these therapeutics whether the combination is synergistic or additive. Thus, the novel combinational therapy of the present invention yields improved efficacy over either agent used as a single-agent therapy.

In one embodiment, an animal with a solid tumor cancer is administered a pharmaceutical composition of the invention and treated with radiation therapy (e.g., gamma radiation or x-ray radiation). In a specific embodiment, the invention provides a method to treat or prevent cancer that has shown to be refractory to radiation therapy. The pharmaceutical composition may be administered concurrently with radiation therapy. Alternatively, radiation therapy may be administered subsequent to administration of a pharmaceutical composition of the invention, preferably at least an hour, five hours, 12 hours, a day, a week, a month, more preferably several months (e.g., up to three months), subsequent to administration of a pharmaceutical composition.

The radiation therapy administered prior to, concurrently with, or subsequent to the administration of the pharmaceutical composition of the invention can be administered by any method known in the art. Any radiation therapy protocol can be used depending upon the type of cancer to be treated. For example, but not by way of limitation, x-ray radiation can be administered; in particular, high-energy megavoltage (radiation of greater than 1 MeV energy) can be used for deep tumors, and electron beam and orthovoltage X-ray radiation can be used for skin cancers. Gamma ray emitting radioisotopes, such as radioactive isotopes of radium, cobalt and other elements may also be administered to expose tissues to radiation.

Additionally, the invention also provides methods of treatment of cancer with a Pharmaceutical composition as an alternative to radiation therapy where the radiation therapy has proven or may prove too toxic, i.e., results in unacceptable or unbearable side effects, for the subject being treated.

The pharmaceutical compositions of the invention are preferably tested in vitro, and then in vivo for the desired therapeutic or prophylactic activity, prior to use in humans. For example, in vitro assays which can be used to determine whether administration of a specific pharmaceutical composition is indicated, include in vitro cell culture assays in which a patient tissue sample is grown in culture, and exposed to or otherwise administered a pharmaceutical composition, and the effect of such composition upon the tissue sample is observed.

Pharmaceutical compositions of the invention can be tested for their ability to augment activated immune cells by contacting immune cells with a test pharmaceutical composition or a control and determining the ability of the test pharmaceutical composition to modulate (e.g., increase) the biological activity of the immune cells. The ability of a test composition to modulate the biological activity of immune cells can be assessed by detecting the expression of cytokines or antigens, detecting the proliferation of immune cells, detecting the activation of signaling molecules, detecting the effector function of immune cells, or detecting the differentiation of immune cells. Techniques known to those of skill in the art can be used for measuring these activities. For example, cellular proliferation can be assayed by 3H-thymidine incorporation assays and trypan blue cell counts. Cytokine and antigen expression can be assayed, for example, by immunoassays including, but are not limited to, competitive and non-competitive assay systems using techniques such as western blots, immunohisto-chemistry radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A, immunoassays and FACS analysis. The activation of signaling molecules can be assayed, for example, by kinase assays and electromobility shift assays (EMSAs). The effector function of T-cells can be measured, for example, by a 51Cr-release assay (see, e.g., Palladino et al., 1987, Cancer Res. 47:5074-5079 and Blachere et al., 1993, J. Immunotherapy 14:352-356, expressly incorporated herein by reference).

Pharmaceutical compositions of the invention can be tested for their ability to reduce tumor formation in animals suffering from cancer. Pharmaceutical compositions of the invention can also be tested for their ability to alleviate of one or more symptoms associated with a solid tumor cancer. Further, pharmaceutical compositions of the invention can be tested for their ability to increase the survival period of patients suffering from a solid tumor cancer. Techniques known to those of skill in the art can be used to analyze the function of the pharmaceutical compositions of the invention in animals.

In various specific embodiments, in vitro assays can be carried out with representative cells of cell types involved in a solid tumor cancer, to determine if a pharmaceutical composition of the invention has a desired effect upon such cell types.

Pharmaceutical compositions of the invention for use in therapy can be tested in suitable animal model systems prior to testing in humans, including but not limited to rats, mice, chicken, cows, monkeys, pigs, dogs, rabbits, etc. For in vivo testing, prior to administration to humans, any animal model system known in the art may be used.

Each reference cited herein is expressly incorporated herein in its entirety. Such references provide examples representing aspects of the invention, uses of the invention, disclosure of the context of the invention and its use and application. The various aspects disclosed herein, including subject matter incorporated herein by reference, may be employed, in combination or subcombination and in various permutations, consistent with the claims.

The invention may be embodied in other specific forms without departing from its spirit or essential characteristics. The described embodiment is to be considered in all respects only illustrative and not restrictive. The scope of the invention is, therefore, indicated by the appended claims rather by the foregoing description. All changes that fall within the meaning and range of equivalency of the claims are to be embraced within their scope.

The invention claimed is:

1. An anti-tumor method, comprising:
providing a live genetically engineered *Salmonella typhimurium* tumor targeting bacterium to a living human or animal having a solid tumor, the tumor targeting bacterium being derived from a wild type *Salmonella typhimurium* bacterium extracted from a human or animal tumor, the live genetically engineered *Salmonella typhimurium* bacterium being genetically engineered to secrete at least one anti-immunosuppressive agent gene product selected from the group consisting of an anti-PD-1 agent, an anti-PD-L1 agent, an anti-PD-L2 agent, and an anti-CTLA-4 agent, in a pharmaceutically acceptable formulation adapted for human systemic administration; and
permitting the live genetically engineered *Salmonella typhimurium* bacterium to grow within the tumor and to secrete the at least one anti-immunosuppressive agent gene product within the tumor, to produce a non-lethal anti-tumor effect, wherein the live genetically engineered *Salmonella typhimurium* bacterium has a selective tropism for at least one type of solid tumor in the living human or animal.

2. An anti-neoplastic method, comprising:
administering a live genetically engineered 22 to a subject having a solid neoplasm, the live genetically engineered *Salmonella typhimurium* being genetically engineered to secrete at least one heterologous anti-immunosuppressive antibody that antagonizes at least one of PD-1, PD-L1, PD-L2, and CTLA-4, in a pharmaceutically acceptable formulation adapted for systemic administration to the subject; and
permitting the live genetically engineered *Salmonella typhimurium* to grow within the solid tumor and to secrete the at least one anti-immunosuppressive agent gene product within the solid tumor without lethality to the subject, to produce an anti-solid tumor effect, wherein the live genetically engineered *Salmonella typhimurium* has a selective tropism for at least one type of solid tumor in the subject.

3. The antineoplastic method according to claim 2, wherein the at least one heterologous anti-immunosuppressive antibody antagonizes PD-1.

4. The antineoplastic method according to claim 2, wherein the at least one heterologous anti-immunosuppressive antibody antagonizes PD-1.

5. The antineoplastic method according to claim 2, wherein the at least one heterologous anti-immunosuppressive antibody antagonizes PD-L2.

6. The antineoplastic method according to claim 3, wherein the at least one heterologous anti-immunosuppressive antibody antagonizes CTLA-4.

7. The antineoplastic method according to claim 1, wherein the at least one heterologous anti-immunosuppressive gene product antagonizes at least one of PD-1, PD-1, and PD-L2.

8. The antineoplastic method according to claim 1, wherein the at least one heterologous anti-immunosuppressive gene product antagonizes CTLA-4.

9. An anti-neoplasm method, comprising:
providing a live genetically engineered *Salmonella typhimurium* bacterium to a living genetically engineered to selectively secrete at least one anti-immunosuppressive agent gene product within the neoplasm, the anti-immunosuppressive agent gene product being selected from the group consisting of an anti-PD-1 agent, an anti-PD-L1 agent, an anti-PD-L2 agent, and an anti-CTLA-4 agent, in a pharmaceutically acceptable formulation adapted for systemic administration to the living subject; and
permitting the live genetically engineered *Salmonella typhimurium* bacterium to grow and to selectively secrete the at least one anti-immunosuppressive agent gene product within the neoplasm, to produce a non-lethal anti-neoplastic effect.

10. The anti-neoplastic method according to claim 9, wherein the at least one anti-immunosuppressive agent gene product is an anti-PD-1 agent.

11. The method according to claim 9,
wherein the live genetically engineered *Salmonella typhimurium* bacterium is a tumor targeting bacterium,
further comprising:
administering a first pharmaceutically acceptable formulation containing the tumor targeting bacterium to the living subject having the neoplastic disease, the tumor targeting bacterium being genetically engineered to have at least one gene which causes the tumor targeting bacterium to produce at least one anti-immunosuppressive agent;
permitting the tumor targeting bacterium to grow within the living human subject; and
clearing the tumor targeting bacterium from the living subject after growing by administration of a second pharmaceutically acceptable formulation containing an antibiotic agent,
wherein the growth of the tumor targeting bacterium is effective during a period between said administering and said clearing to cause antineoplastic effects which are non-lethal to the living subject.

12. The method according to claim 9, wherein the live genetically engineered *Salmonella typhimurium* bacterium is genetically engineered to provide at least one of a sialic acid, an O-oligosaccharide antigen, and an H flagellar antigens, to display a heterologous carbohydrate decoration pattern.

13. The method according to claim 9, wherein the live genetically engineered *Salmonella typhimurium* bacterium comprises at least one first gene, producing at least one secreted heterologous gene product comprising a sialic acid O-acyl transferase.

14. The method according to claim 9, wherein the live genetically engineered *Salmonella typhimurium* bacterium comprises an inducible promoter responsive to at least one of tet, arabinose, hypoxia, a cellular SOS response promoter, X-rays, and mitomycin to promote production of the at least one anti-immunosuppressive agent.

15. The method according to claim 9, wherein the at least one anti-immunosuppressive agent gene product is an affibody.

16. The method according to claim 9, wherein the anti-immunosuppressive agent gene product comprises an anti-PD-1 agent.

17. The method according to claim 9, wherein the anti-immunosuppressive agent gene product comprises an anti-PD-L1 agent.

18. The method according to claim 9, wherein the anti-immunosuppressive agent gene product comprises an anti-PD-L2 agent.

19. The method according to claim 9, wherein the anti-immunosuppressive agent gene product comprises an anti-CTLA-4 agent.

20. The method according to claim 9, wherein the live genetically engineered *Salmonella typhimurium* bacterium is further genetically engineered to have at least one gene which causes the live genetically engineered *Salmonella typhimurium* bacterium to produce at least one protease inhibitor peptide adapted to inhibit a protease of the living subject that degrades the at least one anti-immunosuppressive agent gene product.

21. The method according to claim 9, wherein the live genetically engineered *Salmonella typhimurium* bacterium is a tumor targeting bacterium.

* * * * *

```
                          SEQUENCE LISTING

<160> NUMBER OF SEQ ID NOS: 10

<210> SEQ ID NO 1
<211> LENGTH: 24
<212> TYPE: DNA
<213> ORGANISM: Artificial Sequence
<220> FEATURE:
<223> OTHER INFORMATION: Chlamydia specific histone-like protein binding
      sequence 1

<400> SEQUENCE: 1
aatagggttt cttttaatag aaac                                            24

<210> SEQ ID NO 2
<211> LENGTH: 24
<212> TYPE: DNA
<213> ORGANISM: Artificial Sequence
<220> FEATURE:
<223> OTHER INFORMATION: Chlamydia specific histone-like protein binding
      sequence 2

<400> SEQUENCE: 2
aatagggatt ccagtaacaa caag                                            24

<210> SEQ ID NO 3
<211> LENGTH: 1053
<212> TYPE: DNA
<213> ORGANISM: Artificial Sequence
<220> FEATURE:
<223> OTHER INFORMATION: upstream regulon promoter/operator, MarR and
      MarA genes, start codon (ATG) fusion
```

<400> SEQUENCE: 3

```
cagtgtgcaa gttaatatcc tctacaacct ataacctgta attatcaatt agttacaagt      60
tatcacagca caatacccccg gacgcctttt agcaaatcgt ggcatcggcc aattcattta    120
gttgacttat acttgcctgg gcaatagtat ctgacgaaat taattacttg ccggggcaac    180
cattttgaaa agcaccagtg atctgttcaa tgaaatcatt ccgctgggtc gcttgatcta    240
catggtaaat cagaaaaaag atcgcctgtt aaataactat ttatcccccgc tggatatcac    300
cgcaacacag tttaaagtgc tttgctcgat acgctgcgcg ggatgtatta ccccggttga    360
acttaaaaaa gtgctgtctg tcgatctcgg cgcattgacg cggatgctcg accgcctgct    420
gtgcaaaggc tggatcgaaa gactgccgaa tcctaatgac aaacgcggcg tactggtgaa    480
gctaacgccg gacggcgcgg caatttgtga gcaatgtcat caacgaccag ggcaagacct    540
gcatcaggaa ttaacaaaaa acttaacggc ggacgaagtg gcaacgcttg agtatttgct    600
caagaaaatt ctgccgtaga caaaaaagag gtatgacgat gtccagacgc aacactgacg    660
ctattactat tcatagcatt ttggactgga tcgaggataa cctggagtcg ccgctctcac    720
tggaaaaagt gtctgagcgt tcaggatatt ccaaatggca cctgcaacgg atgtttaaaa    780
aagagaccgg tcattcatta ggccaataca tccgcagccg taaaatgacg gaaatcgcgc    840
aaaaattaaa agagagcaac gagcccattc tctatctggc ggaacgctat ggctttgagt    900
cacagcaaac attgacccgg acgttcaaaa actatttttga tgtgccgcca cacaaatacc    960
ggatcaccaa tatgcatggc gaatcacggt atatgctgcc gctgaaccat ggcaactact   1020
agtttgttta tgcgccacgc gaagagcacc atg                                  1053
```

<210> SEQ ID NO 4
<211> LENGTH: 24
<212> TYPE: PRT
<213> ORGANISM: Escherichia coli

<400> SEQUENCE: 4

```
Met Asn Ile Leu His Ile Cys Val Thr Ser Lys Trp Phe Asn Ile Asp
1               5                   10                  15

Asn Lys Ile Val Asp His Arg Pro
            20
```

<210> SEQ ID NO 5
<211> LENGTH: 471
<212> TYPE: PRT
<213> ORGANISM: Escherichia coli

<400> SEQUENCE: 5

```
Met Glu Asn Phe Lys His Leu Pro Glu Pro Phe Arg Ile Arg Val Ile
1               5                   10                  15

Glu Pro Val Lys Arg Thr Thr Arg Ala Tyr Arg Glu Glu Ala Ile Ile
            20                  25                  30

Lys Ser Gly Met Asn Pro Phe Leu Leu Asp Ser Glu Asp Val Phe Ile
        35                  40                  45

Asp Leu Leu Thr Asp Ser Gly Thr Gly Ala Val Thr Gln Ser Met Gln
    50                  55                  60

Ala Ala Met Met Arg Gly Asp Glu Ala Tyr Ser Gly Ser Arg Ser Tyr
65                  70                  75                  80

Tyr Ala Leu Ala Glu Ser Val Lys Asn Ile Phe Gly Tyr Gln Tyr Thr
                85                  90                  95
```

Ile Pro Thr His Gln Gly Arg Gly Ala Glu Gln Ile Tyr Ile Pro Val
            100                 105                 110

Leu Ile Lys Lys Arg Glu Gln Glu Lys Gly Leu Asp Arg Ser Lys Met
        115                 120                 125

Val Ala Phe Ser Asn Tyr Phe Phe Asp Thr Thr Gln Gly His Ser Gln
    130                 135                 140

Ile Asn Gly Cys Thr Val Arg Asn Val Tyr Ile Lys Glu Ala Phe Asp
145                 150                 155                 160

Thr Gly Val Arg Tyr Asp Phe Lys Gly Asn Phe Asp Leu Glu Gly Leu
                165                 170                 175

Glu Arg Gly Ile Glu Glu Val Gly Pro Asn Asn Val Pro Tyr Ile Val
            180                 185                 190

Ala Thr Ile Thr Ser Asn Ser Ala Gly Gly Gln Pro Val Ser Leu Ala
        195                 200                 205

Asn Leu Lys Ala Met Tyr Ser Ile Ala Lys Lys Tyr Asp Ile Pro Val
    210                 215                 220

Val Met Asp Ser Ala Arg Phe Ala Glu Asn Ala Tyr Phe Ile Lys Gln
225                 230                 235                 240

Arg Glu Ala Glu Tyr Lys Asp Trp Thr Ile Glu Gln Ile Thr Arg Glu
                245                 250                 255

Thr Tyr Lys Tyr Ala Asp Met Leu Ala Met Ser Ala Lys Lys Asp Ala
            260                 265                 270

Met Val Pro Met Gly Gly Leu Leu Cys Met Lys Asp Asp Ser Phe Phe
        275                 280                 285

Asp Val Tyr Thr Glu Cys Arg Thr Leu Cys Val Val Gln Glu Gly Phe
    290                 295                 300

Pro Thr Tyr Gly Gly Leu Glu Gly Gly Ala Met Glu Arg Leu Ala Val
305                 310                 315                 320

Gly Leu Tyr Asp Gly Met Asn Leu Asp Trp Leu Ala Tyr Arg Ile Ala
                325                 330                 335

Gln Val Gln Tyr Leu Val Asp Gly Leu Glu Glu Ile Gly Val Val Cys
            340                 345                 350

Gln Gln Ala Gly Gly His Ala Ala Phe Val Asp Ala Gly Lys Leu Leu
        355                 360                 365

Pro His Ile Pro Ala Asp Gln Phe Pro Ala Gln Ala Leu Ala Cys Glu
    370                 375                 380

Leu Tyr Lys Val Ala Gly Ile Arg Ala Val Glu Ile Gly Ser Phe Leu
385                 390                 395                 400

Leu Gly Arg Asp Pro Lys Thr Gly Lys Gln Leu Pro Cys Pro Ala Glu
                405                 410                 415

Leu Leu Arg Leu Thr Ile Pro Arg Ala Thr Tyr Thr Gln Thr His Met
            420                 425                 430

Asp Phe Ile Ile Glu Ala Phe Lys His Val Lys Glu Asn Ala Ala Asn
        435                 440                 445

Ile Lys Gly Leu Thr Phe Thr Tyr Glu Pro Lys Val Leu Arg His Phe
    450                 455                 460

Thr Ala Lys Leu Lys Glu Val
465                 470

<210> SEQ ID NO 6
<211> LENGTH: 415
<212> TYPE: PRT
<213> ORGANISM: Escherichia coli

<400> SEQUENCE: 6

Met Thr Asp Gln Ala Glu Lys Lys His Ser Ala Phe Trp Gly Val Met
1               5                   10                  15
Val Ile Ala Gly Thr Val Ile Gly Gly Met Phe Ala Leu Pro Val
            20                  25                  30
Asp Leu Ala Gly Ala Trp Phe Phe Trp Gly Ala Phe Ile Leu Ile Ile
                35                  40                  45
Ala Trp Phe Ser Met Leu His Ser Gly Leu Leu Leu Glu Ala Asn
50                      55                  60
Leu Asn Tyr Pro Val Gly Ser Ser Phe Asn Thr Ile Thr Lys Asp Leu
65                  70                  75                  80
Ile Gly Asn Thr Trp Asn Ile Ile Ser Gly Ile Thr Val Ala Phe Val
                85                  90                  95
Leu Tyr Ile Leu Thr Tyr Ala Tyr Ile Ser Ala Asn Gly Ala Ile Ile
                100                 105                 110
Ser Glu Thr Ile Ser Met Asn Leu Gly Tyr His Ala Asn Pro Arg Ile
                115                 120                 125
Val Gly Ile Cys Thr Ala Ile Phe Val Ala Ser Val Leu Trp Leu Ser
130                 135                 140
Ser Leu Ala Ala Ser Arg Ile Thr Ser Leu Phe Leu Gly Leu Lys Ile
145                 150                 155                 160
Ile Ser Phe Val Ile Val Phe Gly Ser Phe Phe Gln Val Asp Tyr
                165                 170                 175
Ser Ile Leu Arg Asp Ala Thr Ser Ser Thr Ala Gly Thr Ser Tyr Phe
                180                 185                 190
Pro Tyr Ile Phe Met Ala Leu Pro Val Cys Leu Ala Ser Phe Gly Phe
                195                 200                 205
His Gly Asn Ile Pro Ser Leu Ile Ile Cys Tyr Gly Lys Arg Lys Asp
                210                 215                 220
Lys Leu Ile Lys Ser Val Val Phe Gly Ser Leu Leu Ala Leu Val Ile
225                 230                 235                 240
Tyr Leu Phe Trp Leu Tyr Cys Thr Met Gly Asn Ile Pro Arg Glu Ser
                245                 250                 255
Phe Lys Ala Ile Ile Ser Ser Gly Gly Asn Val Asp Ser Leu Val Lys
                260                 265                 270
Ser Phe Leu Gly Thr Lys Gln His Gly Ile Ile Glu Phe Cys Leu Leu
                275                 280                 285
Val Phe Ser Asn Leu Ala Val Ala Ser Ser Phe Phe Gly Val Thr Leu
                290                 295                 300
Gly Leu Phe Asp Tyr Leu Ala Asp Leu Phe Lys Ile Asp Asn Ser His
305                 310                 315                 320
Gly Gly Arg Phe Lys Thr Val Leu Leu Thr Phe Leu Pro Pro Ala Leu
                325                 330                 335
Leu Tyr Leu Ile Phe Pro Asn Gly Phe Ile Tyr Gly Ile Gly Gly Ala
                340                 345                 350
Gly Leu Cys Ala Thr Ile Trp Ala Val Ile Ile Pro Ala Val Leu Ala
                355                 360                 365
Ile Lys Ala Arg Lys Lys Phe Pro Asn Gln Met Phe Thr Val Trp Gly
                370                 375                 380
Gly Asn Leu Ile Pro Ala Ile Val Ile Leu Phe Gly Ile Thr Val Ile
385                 390                 395                 400
Leu Cys Trp Phe Gly Asn Val Phe Asn Val Leu Pro Lys Phe Gly
                405                 410                 415

<210> SEQ ID NO 7
<211> LENGTH: 3049
<212> TYPE: DNA
<213> ORGANISM: Escherichia coli

<400> SEQUENCE: 7

| | | | | | |
|---|---|---|---|---|---|
| atgaatatct | tacatatatg | tgtgacctca | aatggttca | atattgacaa | caaaattgtc | 60 |
| gatcaccgcc | cttgatttgc | ccttctgtag | ccatcaccag | agccaaaccg | attagattca | 120 |
| atgtgatcta | tttgtttgct | atatcttaat | tttgccttt | gcaaaggtca | tctctcgttt | 180 |
| atttacttgt | tttagtaaat | gatggtgctt | gcatatatat | ctggcgaatt | aatcggtata | 240 |
| gcagatgtaa | tattcacagg | gatcactgta | attaaaataa | atgaaggatt | atgtaatgga | 300 |
| aaactttaaa | catctccctg | aaccgttccg | cattcgtgtt | attgagccag | taaaacgtac | 360 |
| cactcgcgct | tatcgtgaag | aggcaattat | taaatccggt | atgaacccgt | tcctgctgga | 420 |
| tagcgaagat | gttttatcg | atttactgac | cgacagcggc | accggggcgg | tgacgcagag | 480 |
| catgcaggct | gcgatgatgc | gcggcgacga | agcctacagc | ggcagtcgta | gctactatgc | 540 |
| gttagccgag | tcagtgaaaa | atatctttgg | ttatcaatac | accattccga | ctcaccaggg | 600 |
| ccgtggcgca | gagcaaatct | atattccggt | actgattaaa | aaacgcgagc | aggaaaaagg | 660 |
| cctggatcgc | agcaaaatgg | tggcgttctc | taactatttc | tttgatacca | cgcagggcca | 720 |
| tagccagatc | aacggctgta | ccgtgcgtaa | cgtctatatc | aaagaagcct | tcgatacggg | 780 |
| cgtgcgttac | gactttaaag | gcaactttga | ccttgaggga | ttagaacgcg | gtattgaaga | 840 |
| agttggtccg | aataacgtgc | cgtatatcgt | tgcaaccatc | accagtaact | ctgcaggtgg | 900 |
| tcagccggtt | tcactggcaa | acttaaaagc | gatgtacagc | atcgcgaaga | aatacgatat | 960 |
| tccggtggta | atggactccg | cgcgctttgc | tgaaaacgcc | tatttcatca | agcagcgtga | 1020 |
| agcagaatac | aaagactgga | ccatcgagca | gatcacccgc | gaaacctaca | aatatgccga | 1080 |
| tatgctggcg | atgtccgcca | agaaagatgc | gatggtgccg | atgggcggcc | tgctgtgcat | 1140 |
| gaaagacgac | agcttctttg | atgtgtacac | cgagtgcaga | acccttgcg | tggtgcagga | 1200 |
| aggcttcccg | acatatggcg | gcctggaagg | cggcgcgatg | gagcgtctgg | cggtaggtct | 1260 |
| gtatgacggc | atgaatctcg | actggctggc | ttatcgtatc | gcgcaggtac | agtatctggt | 1320 |
| cgatggtctg | aagagattg | gcgttgtctg | ccagcaggcg | ggcggtcacg | cggcattcgt | 1380 |
| tgatgccggt | aaactgttgc | cgcatatccc | ggcagaccag | ttcccggcac | aggcgctggc | 1440 |
| ctgcgagctg | tataaagtcg | ccggtatccg | tgcggtagaa | attggctctt | tcctgttagg | 1500 |
| ccgcgatccg | aaaaccggta | acaactgcc | atgcccggct | gaactgctgc | gtttaaccat | 1560 |
| tccgcgcgca | acatatactc | aaacacatat | ggacttcatt | attgaagcct | ttaaacatgt | 1620 |
| gaaagagaac | gcggcgaata | ttaaaggatt | aacctttacg | tacgaaccga | agtattgcg | 1680 |
| tcacttcacc | gcaaaactta | agaagttta | attaatacta | cagagtggct | ataaggatgt | 1740 |
| tagccactct | cttaccctac | atcctcaata | acaaaaatag | ccttcctcta | aaggtggcat | 1800 |
| catgactgat | caagctgaaa | aaagcactc | tgcattttgg | ggtgttatgg | ttatagcagg | 1860 |
| tacagtaatt | ggtggaggta | tgtttgcttt | acctgttgat | cttgccggtg | cctggttttt | 1920 |
| ctggggtgcc | tttatcctta | tcattgcctg | gttttcaatg | cttcattccg | ggttattgtt | 1980 |
| attagaagca | aatttaaatt | atcccgtcgg | ctccagtttt | aacaccatca | ccaaagattt | 2040 |
| aatcggtaac | acctgaaca | ttatcagcgg | tattaccgtt | gccttcgttc | tctatatcct | 2100 |
| cacttatgcc | tatatctctg | ctaatggtgc | gatcattagt | gaaacgatat | caatgaattt | 2160 |

```
gggttatcac gctaatccac gtattgtcgg gatctgcaca gccattttcg ttgccagcgt    2220
attgtggtta agttcgttag ccgccagtcg tattacctca ttgttcctcg ggctgaagat    2280
tatctccttt gtgatcgtgt ttggttcttt tttcttccag gtcgattact ccattctgcg    2340
cgacgccacc agctccactg cgggaacgtc ttacttcccg tatatcttta tggctttgcc    2400
ggtgtgtctg gcgtcatttg gtttccacgg caatattccc agcctgatta tttgctatgg    2460
aaaacgcaaa gataagttaa tcaaaagcgt ggtatttggt tcgctgctgg cgctggtgat    2520
ttatctcttc tggctctatt gcaccatggg gaatattccg cgagaaagct taaggcgat    2580 tatctcctca ggcggcaacg ttgattcgct ggtgaaatcg ttcctcggca ccaaacagca    2640
cggcattatc gagttttgcc tgctggtgtt ctctaactta gctgttgcca gttcgttctt    2700
tggtgtcacg ctggggttgt tcgattatct ggcggacctg tttaagattg ataactccca    2760
cggcgggcgt ttcaaaaccg tgctgttaac cttcctgcca cctgcgttgt tgtatctgat    2820
cttcccgaac ggctttattt acgggatcgg cggtgccggg ctgtgcgcca ccatctgggc    2880
ggtcattatt cccgcagtgc ttgcaatcaa agctcgcaag aagtttccca atcagatgtt    2940
cacggtctgg ggcggcaatc ttattccggc gattgtcatt ctctttggta taaccgtgat    3000
tttgtgctgg ttcggcaacg tctttaacgt gttacctaaa tttggctaa                3049

<210> SEQ ID NO 8
<211> LENGTH: 60
<212> TYPE: DNA
<213> ORGANISM: Artificial Sequence
<220> FEATURE:
<223> OTHER INFORMATION: Forward primer =Tryp Kpn Nsi F1

<400> SEQUENCE: 8
tcggtaccca ggaggaattc accatgcata atatcttaca tatatgtgtg acctcaaaat    60

<210> SEQ ID NO 9
<211> LENGTH: 38
<212> TYPE: DNA
<213> ORGANISM: Artificial Sequence
<220> FEATURE:
<223> OTHER INFORMATION: reverse primer = Tryp Xba R1

<400> SEQUENCE: 9
gatctctaga gaaggattta gccaaattta ggtaacac                            38

<210> SEQ ID NO 10
<211> LENGTH: 2788
<212> TYPE: DNA
<213> ORGANISM: Artificial Sequence
<220> FEATURE:
<223> OTHER INFORMATION: modified pTrc99a with the arabinose promoter

<400> SEQUENCE: 10
gggggcggcc gcaagaaacc aattgtccat attgcatcag acattgccgt cactgcgtct    60
tttactggct cttctcgcta accaaaccgg taaccccgct tattaaaagc attctgtaac    120
aaagcgggac caaagccatg acaaaaacgc gtaacaaaag tgtctataat cacggcagaa    180
aagtccacat tgattatttg cacggcgtca cactttgcta tgccatagca ttttttatcca   240 taagattagc ggatcctacc tgacgctttt tatcgcaact ctctactgtt tctccatacc    300
cgtttttttg ggctagcgaa ttcgagctcg gtacccagga ggaattcacc atggaattcg    360
agctcggtac ccggggatcc tctagagtcg acctgcaggc atgcaagctt ggctgttttg    420
```

-continued

```
gcggatgaga gaagattttc agcctgatac agattaaatc agaacgcaga agcggtctga    480
taaaacagaa tttgcctggc ggcagtagcg cggtggtccc acctgacccc atgccgaact    540
cagaagtgaa acgccgtagc gccgatggta gtgtggggtc tccccatgcg agagtaggga    600
actgccaggc atcaaataaa acgaaaggct cagtcgaaag actgggcctt tcgttttatc    660
tgttgtttgt cggtgaacgc tctcctgagt aggacaaatc cgccgggagc ggatttgaac    720
gttgcgaagc aacggcccgg agggtggcgg gcaggacgcc cgccataaac tgccaggcat    780
caaattaagc agaaggccat cctgacggat ggcctttttg cgtttctaca aactctttttg    840 gtttattttt ctaaatacat tcaaatatgt atccgctcat gagacaataa ccctgataaa    900
tgcttcaata atattgaaaa aggaagagta tgagtattca catttccgt gtcgcccttag    960 ttccctttttg tgcggcattt tgccttcctg ttttgctca cccagaaacg ctggtgaaag   1020
taaaagatgc tgaagatcag ttgggtgcac gagtgggtta catcgaactg gatctcaaca   1080
gcggtaagat ccttgagagt tttcgccccg aagaacgttt tccaatgatg agcacttttta  1140 aagttctgct atgtggcgcg gtattatccc gtgttgacgc cgggcaagag caactcggtc   1200
gccgcataca ctattctcag aatgacttgg ttgagtactc accagtcaca gaaaagcatc   1260
ttacggatgg catgacagta agagaattat gcagtgctgc cataaccatg agtgataaca   1320
ctgcggccaa cttacttctg acaacgatcg gaggaccgaa ggagctaacc gcttttttgc   1380
acaacatggg ggatcatgta actcgccttg atcgttggga accggagctg aatgaagcca   1440
taccaaacga cgagcgtgac accacgatgc ctacagcaat ggcaacaacg ttgcgcaaac   1500
tattaactgg cgaactactt actctagctt cccggcaaca attaatagac tggatggagg   1560
cggataaagt tgcaggacca cttctgcgct cggcccttcc ggctggctgg tttattgctg   1620
ataaatctgg agccggtgag cgtgggtctc gcggtatcat tgcagcactg gggccagatg   1680
gtaagccctc ccgtatcgta gttatctaca cgacggggag tcaggcaact atggatgaac   1740
gaaatagaca gatcgctgag ataggtgcct cactgattaa gcattggtaa ctgtcagacc   1800
aagtttactc atatatactt tagattgatt taaaacttca ttttaattt aaaaggatct   1860 aggtgaagat cctttttgat aatctcatga ccaaaatccc ttaacgtgag ttttcgttcc   1920
actgagcgtc agaccccgta gaaaagatca aaggatcttc ttgagatcct ttttttctgc   1980
gcgtaatctg ctgcttgcaa acaaaaaaac caccgctacc agcggtggtt tgtttgccgg   2040
atcaagagct accaactctt tttccgaagg taactggctt cagcagagcg cagataccaa   2100
atactgtcct tctagtgtag ccgtagttag gccaccactt caagaactct gtagcaccgc   2160
ctacatacct cgctctgcta atcctgttac cagtggctgc tgccagtggc gataagtcgt   2220
gtcttaccgg gttggactca agacgatagt taccggataa ggcgcagcgg tcgggctgaa   2280
cggggggttc gtgcacacag cccagcttgg agcgaacgac ctacaccgaa ctgagatacc   2340
tacagcgtga gctatgagaa agcgccacgc ttcccgaagg gagaaaggcg gacaggtatc   2400
cggtaagcgg cagggtcgga acaggagagc gcacgaggga gcttccaggg ggaaacgcct   2460
ggtatcttta tagtcctgtc gggtttcgcc acctctgact tgagcgtcga ttttttgtgat  2520 gctcgtcagg ggggcggagc ctatggaaaa acgccagcaa cgcggccttt ttacggttcc   2580
tggccttttg ctggcctttt gctcacatgt tctttcctgc gttatcccct gattctgtgg   2640
ataaccgtat taccgccttt gagtgagctg ataccgctcg ccgcagccga acgaccgagc   2700
```

```
gcagcgagtc agtgagcgag gaagcggaag agcgcctgat gcggtatttt ctccttacgc    2760
atctgtgcgg tatttcacac cgcatatg                                      2788
```